(12) United States Patent
Paspaliaris

(10) Patent No.: US 11,103,537 B2
(45) Date of Patent: Aug. 31, 2021

(54) CELLS EXPRESSING PARATHYROID HORMONE 1 RECEPTOR AND USES THEREOF

(71) Applicant: Tithon Biotech Inc., San Diego, CA (US)

(72) Inventor: Vasilis Paspaliaris, Malvern East (AU)

(73) Assignee: Tithon Biotech Inc., San Diego, CA (US)

( * ) Notice: Subject to any disclaimer, the term of this patent is extended or adjusted under 35 U.S.C. 154(b) by 695 days.

(21) Appl. No.: 15/683,016

(22) Filed: Aug. 22, 2017

(65) Prior Publication Data

US 2017/0368107 A1 Dec. 28, 2017

Related U.S. Application Data

(63) Continuation-in-part of application No. PCT/US2017/038598, filed on Jun. 21, 2017.

(60) Provisional application No. 62/445,636, filed on Jan. 12, 2017, provisional application No. 62/353,993, filed on Jun. 23, 2016.

(51) Int. Cl.
| | |
|---|---|
| *A61K 35/12* | (2015.01) |
| *A61K 35/28* | (2015.01) |
| *A61K 35/545* | (2015.01) |
| *A61K 38/29* | (2006.01) |
| *C07K 14/72* | (2006.01) |
| *C12N 5/071* | (2010.01) |
| *C12N 5/0797* | (2010.01) |
| *C12Q 1/6809* | (2018.01) |
| *C12N 5/0775* | (2010.01) |
| *C12N 5/074* | (2010.01) |
| *G01N 33/74* | (2006.01) |
| *A61K 38/17* | (2006.01) |
| *C12N 5/0789* | (2010.01) |
| *A61K 38/00* | (2006.01) |

(52) U.S. Cl.
CPC ............ *A61K 35/545* (2013.01); *A61K 35/28* (2013.01); *A61K 38/29* (2013.01); *C07K 14/72* (2013.01); *C12N 5/0602* (2013.01); *C12N 5/0607* (2013.01); *C12N 5/0623* (2013.01); *C12N 5/0665* (2013.01); *C12Q 1/6809* (2013.01); *A61K 38/00* (2013.01); *A61K 38/17* (2013.01); *A61K 2035/122* (2013.01); *C12N 5/0647* (2013.01); *C12N 2501/37* (2013.01); *C12N 2510/00* (2013.01); *G01N 33/74* (2013.01)

(58) Field of Classification Search
None
See application file for complete search history.

(56) References Cited

U.S. PATENT DOCUMENTS

| | | | | |
|---|---|---|---|---|
| 8,747,905 | B2 * | 6/2014 | Yoon | C12N 5/0647 424/577 |
| 9,155,762 | B2 * | 10/2015 | Ratajczak | A61K 35/12 |
| 2003/0153041 | A1 | 8/2003 | Segre et al. | |
| 2004/0067231 | A1 | 4/2004 | Yoshikawa | |
| 2006/0216277 | A1 * | 9/2006 | Efrat | C12N 5/0676 424/93.21 |
| 2009/0191159 | A1 | 7/2009 | Sakurada et al. | |
| 2012/0094380 | A1 | 4/2012 | Tzu-Bi Shih et al. | |
| 2012/0308535 | A1 | 12/2012 | Gambacurta et al. | |
| 2014/0220682 | A1 | 8/2014 | Perkins et al. | |
| 2015/0353887 | A1 | 12/2015 | Tilly et al. | |

FOREIGN PATENT DOCUMENTS

WO    WO 2009/010885    1/2009

OTHER PUBLICATIONS

Watson et al Enhanced Osteoblast Development After Continuous Infusion of hPTH(1-84) in the Rat Bone vol. 24, No. 2 Feb. 1999:89-94.*
J. Davies "Parathyroid hormone activates adhesion in bone marrow stromal precursor cells," Journal of Endocrinology, vol. 180, No. 3, pp. 505-513, 2004.*
Akimov et al., Bypass of Senescence, Immortalization, and Transformation of Human Hematopoietic Progenitor Cells Stem Cells 2005 1423-1433.*
Williams et al., Cell Therapy for Age-Related Disorders:Myocardial Infarction and Stroke—A Mini-Review Gerontology 2008;54:300-311.*
Zhao et al International Journal of Molecular Medicine 36: 857-864, 2015 ; Expression of human telomerase reverse transcriptase mediates the senescence of mesenchymal stem cells through the PI3K/AKT signaling pathway.*
Podlevsky et al., 2007 Nucleic Acids Research, 2008, vol. 36, Database issue D339-D343; The Telomerase Database.*
Menuki et al Bone 43 (2008) 613-620 Climbing exercise enhances osteoblast differentiation and inhibits adipogenic differentiation with high expression of PTH/PTHrP receptor in bone marrow cells.*
International Search Report for PCT/US2017/038598, dated Sep. 15, 2017.

* cited by examiner

*Primary Examiner* — Maria G Leavitt
(74) *Attorney, Agent, or Firm* — Knobbe Martens Olson & Bear LLP

(57) ABSTRACT

Disclosed herein are pluripotent stem cells cultured with one or more peptide and methods of isolating said stem cells. Also disclosed are methods of targeting the stem cells to a desired region or area within an organism. Also disclosed are methods of using the isolated stem cells for the improvement of fertility, for the promotion of hair growth, for the treatment or prevention of skin conditions, for the treatment or improvement of bone disorders, for the treatment of malignancies, and for the treatment of neurological disorders.

10 Claims, 40 Drawing Sheets

Equine

Canine

Camel

Before Treatment  10 Weeks after Treatment

Pre-treatment

Post-treatment

CELLS EXPRESSING PARATHYROID HORMONE 1 RECEPTOR AND USES THEREOF

CROSS-REFERENCE TO RELATED APPLICATIONS

This application is a continuation-in-part application of PCT Application No. PCT/US2017/038598, which designated the U.S. and was published in English and, which claims the benefit of priority to U.S. Provisional Application Nos. 62/353,993 filed Jun. 23, 2016 and 62/445,636 filed Jan. 12, 2017, the disclosures of which are hereby expressly incorporated by reference in their entirety.

FIELD OF THE INVENTION

The present disclosure relates generally to the field of stem cells, including the isolation of stem cells and the culturing of stem cells. In particular, the disclosure relates to the use of pluripotent stem cells expressing parathyroid hormone type 1 receptor for the use in improving fertility, promoting hair growth, improving or preventing skin conditions, improving or preventing bone disorders, improving or preventing macular degeneration, improving or preventing autoimmune disorders, or improving an age-related disorder. These stem cells are referred to as peripheral blood derived pluripotent stem cells (PBD-PSCs).

BACKGROUND

Human stem cells are primitive, immature, unspecialized pluripotent precursor cells with the ability to divide for indefinite periods and to produce new or specialized cells, and are capable of generating a variety of mature human cell lineages. Stem cells are found in nearly all tissues of the body, including bone marrow, bone, muscle, liver, brain, adipose tissue, blood, and skin.

Stem cells are essential to the body because they act as a repair system that enables regrowth and renewal of cells during injury, disease, or cellular damage. For example, fibroblasts, which are skin stem cells, repair skin damage, including skin lacerations. Osteoblasts, which are bone stem cells, repair bone damage, including bone fractures.

Stem cells are capable of use in a variety of medical applications by repopulating many types of tissues and restoring physiological and anatomical functionality. Such uses include allogenic regenerative cell therapy, autologous regenerative cell therapy, tissue engineering, and regenerative drug therapy.

SUMMARY

The present disclosure is directed to a pluripotent stem cell population, which expresses the parathyroid hormone type 1 receptor (PTH1R) and is capable of differentiating into ectoderm, mesoderm, and endoderm when cultured, and is referred to herein as peripheral blood derived pluripotent stem cells (PBD-PSCs).

Some embodiments relate to a population of cells comprising PBD-PSC and such a cell population is identified, characterized, and/or isolated by the presence of the PTH1R. In some embodiments, the stem cell population comprising PBD-PSC is isolated from adipose tissue, bone marrow, peripheral blood, female ovarian follicular fluid, or male seminal plasma, or combinations thereof. In some embodiments, the stem cell population comprising PBD-PSCs are isolated from mammals, including humans, domestic animals, or farm animals, such as dogs, cats, camels, horses, cattle, pigs, sheep, or goats.

In some embodiments, the PBD-PSCs within the cell population that are expressive of PTH1R are 2.5-4.5 µm in diameter, such as 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 µm in diameter, or an amount within a range defined by any two of the aforementioned values. In some embodiments, the stem cell population comprising PBD-PSCs form embryoid-like bodies when cultured. In some embodiments, the stem cell population comprising PBD-PSCs differentiate into ectoderm, mesoderm, and/or endoderm germ layers when cultured in the appropriate induction media.

In some embodiments, the isolated cell population comprising PBD-PSCs is expressive of classical CD markers. In some embodiments, the PBD-PSCs that are expressive of PTH1R are positive for CD90 and/or CD133; positive/negative for CD29, CD34, CD105, and/or CD106; and/or negative for SSEA-3, CD200, and/or CD45. In some embodiments, the stem cell population comprising PBD-PSCs are expressive of Sox2 and Oct4.

In some embodiments, the PBD-PSCs are cultured with one or more peptides. In some embodiments, the peptide is an extracellular matrix (ECM) protein, a cytokine, a growth factor, or an antigen. In some embodiments, the ECM protein includes, for example, proteoglycans, non-proteoglycan polysaccharides, or fibers, and can include, for example, chondroitin sulfate, heparin sulfate, keratan sulfate, hyaluronic acid, agrin nidogen, collagen, elastin, entactin, fibronectin, laminin, perlecan, total protein, and/or protein fragments. In some embodiments, the cytokine(s) is/are, for example, lymphokines, interleukins, and chemokines, which can include, for example, an interleukin cytokine (IL-1α, IL-1β, IL-2, IL-3, IL-4, IL-5, IL-6, IL-7, IL-8, IL-9, IL-10, IL-11, IL-12, IL-13), an interferon (IFN-α, IFN-β, and IFN-γ), a tumor necrosis factor (TNFα and TNF-β), a colony stimulating factor (GM-CSF and M-CSF), or a combination thereof. In some embodiments, the growth factor includes, for example, an epidermal growth factor (EGF), a platelet derived growth factor (PDGF), a fibroblast growth factor (FGF and bFGF), a transforming growth factor (TGF-α and TGF-β 1, 2, & 3), a vascular endothelial growth factor (VEGF), a hepatocyte growth factor (HGF), a keratinocyte growth factor (KGF), a nerve growth factor (NGF), erythropoietin (EPO), or an insulin-like growth factors (IGF-I and IGF-II), or a combination thereof. In some embodiments, the PBD-PSCs are cultured with retinoic acid and/or with one or more of a derivative of retinoic acid.

In some embodiments, the PBD-PSCs are transfected with one or more heterologous genes encoding a peptide. In some embodiments, the peptide is an extracellular matrix (ECM) protein, a cytokine, a growth factor, or an antigen. In some embodiments, the ECM protein includes, for example, proteoglycans, non-proteoglycan polysaccharides, or fibers, and can include, for example, chondroitin sulfate, heparin sulfate, keratan sulfate, hyaluronic acid, agrin nidogen, collagen, elastin, entactin, fibronectin, laminin, perlecan, total protein, and/or protein fragments. In some embodiments, the cytokine includes, for example, lymphokines, interleukins, and chemokines, which can include, for example, an interleukin cytokine (IL-1α, IL-1β, IL-2, IL-3, IL-4, IL-5, IL-6, IL-7, IL-8, IL-9, IL-10, IL-11, IL-12, IL-13), an interferon (IFN-α, IFN-β, and IFN-γ), a tumor necrosis factor (TNFα and TNF-β), or a colony stimulating factor (GM-CSF and M-CSF), or a combination thereof. In some embodiments, the growth factor includes, for example, an epidermal growth factor (EGF), a platelet derived growth factor (PDGF), a fibroblast growth factor (FGF and bFGF), a transforming growth factor (TGF-α and TGF-β 1, 2, & 3), a vascular endothelial growth factor (VEGF), a hepatocyte growth factor (HGF), a keratinocyte growth factor (KGF), a nerve growth factor (NGF), erythropoietin (EPO), or an insulin-like growth factors (IGF-I and IGF-II), or a combination thereof.

In some embodiments, PBD-PSCs are targeted to a specific region or area within an organism, tissue, or organ. In some embodiments, the PBD-PSCs are attracted to a target region through the overexpression of parathyroid hormone (PTH) and/or the overexpression of parathyroid hormone-related protein (PTHrP) in the area. PTH and PTHrP act as chemoattractants to PBD-PSCs. In some embodiments, the PBD-PSCs are attracted to a region or area having a high concentration of PTH and/or PTHrP. In some embodiments, the high concentration or influx of PTH and/or PTHrP is a result of overexpression, native expression, and/or artificial placement.

Embodiments also include an antibody or binding domain thereof specific for a PTH1R on PBD-PSCs. In some embodiments, the antibody or binding domain is a monoclonal antibody or binding fragment thereof or a poly clonal antibody or binding fragments thereof. In some embodiments, the antibody or binding fragment thereof is a humanized antibody or a humanized binding fragment thereof.

Embodiments also include methods of isolating a pluripotent stem cell population, wherein the stem cell population comprises PBD-PSCs that express PTH1R. In some embodiments, the method comprises contacting a sample comprising a cell population that comprises PBD-PSCs with an antibody or binding fragment thereof specific to PTH1R (preferably bound to a support or surface such as a bead, membrane, filter, container), so as to form a bound cell population (e.g., stem cell population). In some embodiments, the method further comprises isolating the antibody-bound cell population (e.g., stem cell population). In some embodiments, the method comprises releasing the bound cell population (e.g., stem cell population) from the antibody or binding fragment thereof. In some embodiments, the method further comprises contacting a sample comprising the antibody/binding fragment thereof-bound cell population (e.g., stem cell population) with magnetic beads, a surface, or support (e.g., the magnetic beads, surface, support, membrane, or filter can include immobilized or bound antibodies or binding fragments thereof specific for PTH1R). In some embodiments, the method comprises applying a magnetic field and/or centrifugation to the sample, thereby isolating the antibody/binding fragment thereof-bound cell population (e.g., stem cell population).

More embodiments include methods of using PBD-PSCs for the treatment or amelioration or inhibition of a disorder, disease or disease state, wherein the disorder, disease or disease state is infertility, a skin or hair disorder, such as hair loss, hair thinning, a bone disorder, a cancer, a neurological disorder, autoimmune disorders, or a combination thereof. In some embodiments, the subject suffering from one or more disorders is identified by clinical or diagnostic evaluation for one or more of the aforementioned disorders, diseases or disease states and said individual is administered stem cell population comprising PBD-PSCs, wherein the stem cell population comprising PBD-PSCs is administered intravenously, intra-arterially, subcutaneously, transdermally, intra-vitreally, intraocularly, subconjunctivally, retrobulbarly, sub-orbitally or topically, or by a combination thereof. In some embodiments, the treatment or amelioration of the disorder, disease or disease state results in the amelioration, improvement, reversal, or regression of the disorder. In some embodiments, intra-arterial injections include injection into the uterine, pancreatic, or ovarian artery, or combinations thereof.

Some embodiments provided herein relate to a method of improving, ameliorating, reversing, inhibiting or treating diabetes. In some embodiments, the method includes administering an effective amount of a composition. In some embodiments, the composition includes an isolated population of pluripotent stem cells isolated as described herein. In some embodiments, the composition includes the isolated population of pluripotent stem cells as described herein to a subject in need. In some embodiments, diabetes is Type 1 diabetes. In some embodiments, the composition is administered intra-arterially into the pancreatic artery. In some embodiments, the composition is administered once every 12 weeks. In some embodiments, administration of the composition reduces an amount of daily average insulin usage by the subject. In some embodiments, the daily average insulin usage is reduced by 2-10%, 5-20%, 10-30%, 20-40%, 30-50%, 40-60%, 50-70%, 60-80%, 70-90%, or 80-100% or within a range defined by any two of the aforementioned percentages.

Some embodiments provided herein relate to a method of reducing the average daily insulin dose in a subject suffering from diabetes. In some embodiments, the method includes administering an effective amount of a composition. In some embodiments, the composition includes an isolated population of pluripotent stem cells isolated by the method as described herein. In some embodiments, the composition includes the isolated population of pluripotent stem cells as described herein to a subject in need. In some embodiments, diabetes is Type 1 diabetes. In some embodiments, the composition is administered intra-arterially into the pancreatic artery. In some embodiments, the composition is administered once every 12 weeks. In some embodiments, administration of the composition reduces an amount of daily average insulin usage by the subject by 2-10%, 5-20%, 10-30%, 20-40%, 30-50%, 40-60%, 50-70%, 60-80%, 70-90%, or 80-100% or within a range defined by any two of the aforementioned percentages.

Some embodiments provided herein relate to a method for growing an isolated population of pluripotent stem cells on a matrix. In some embodiments, the method includes isolating a population of pluripotent stem cells from a sample by the method of as described herein, contacting a nanofiber matrix with the isolated pluripotent stem cells, and growing the isolated pluripotent stem cells on the nanofiber matrix. In some embodiments, a matrix including pluripotent stem cells is produced. In some embodiments, the nanofiber matrix includes polymer fibers, including, for example, polydimethylsiloxane, polyglycerol sebacate, polycaprolactone, polylactic acid, polyglycolic acid, cellulose, alginate, agar, agarose, collagen I, collagen IV, hyaluronic acid, fibrin, poly-L-lactide, or poly(lactic-co-glycolic acid). In some embodiments, the polymer fibers are electrospun. In some embodiments, the polymer fibers range in thickness from 200 to 700 μm (e.g., 200, 300, 400, 500, 600, or 700 μm or within a range defined by any two of the aforementioned thicknesses). In some embodiments, the pluripotent stem cells bind to and lay down in the matrix within 2-40 minutes (e.g., 2, 3, 4, 5, 6, 7, 8, 9, 10, 15, 20, 25, 30, 35, or 40 minutes or an amount within a range defined by any two of the aforementioned values). In some embodiments, the matrix comprising pluripotent stem cells is used for injecting into joints or bones. In some embodiments, the matrix comprising pluripotent stem cells is used for covering a wound with or without a dressing, which may include a gel.

Some embodiments provided herein relate to a method of treating, reversing, inhibiting, or improving an age-related disorder in a subject. In some embodiments, the method comprises optionally, isolating a population of parathyroid hormone (PTH) receptor-positive pluripotent stem cells from the subject, and/or transfecting said isolated population of PTH receptor-positive pluripotent stem cells with a human telomerase reverse transcriptase (hTERT) gene to generate hTERT transfected PTH receptor-positive pluripotent stem cells, and administering a therapeutically effective amount of the hTERT transfected PTH receptor-positive pluripotent stem cells to said subject. In some embodiments, said therapeutically effective amount is an amount sufficient to reduce telomere shortening, increase cellular self-renewal, increase lifespan, reduce fine lines or wrinkles, and/or reduce aging in said subject. In some embodiments, said age-related disorder is osteoporosis, arthrosis, glucose intolerance, insulin resistance, reduced heart, circulatory, or lung function, cardiovascular disease, a neurodegenerative disease, loss of memory, loss of neuromuscular coordination, and/or decrease of longevity. In some embodiments, telomerase activity is recovered in cells of said subject. In some embodiments, said population of PTH receptor-positive pluripotent stem cells are isolated from peripheral blood, seminal fluid, or ovarian follicular fluid. In some embodiments, transfecting said population of PTH receptor-positive stem cells comprises non-viral transfection. In some embodiments, transfecting said population of PTH receptor-positive stem cells comprises chemical-based transfection, particle-based transfection, viral transfection, or electroporation. In some embodiments, the hTERT transfected PTH receptor-positive pluripotent stem cells are administered to the subject once weekly, once monthly, or once annually.

Some embodiments provided herein relate to a composition comprising an isolated population of parathyroid hormone (PTH) receptor-positive pluripotent stem cells transfected with human telomerase reverse transcriptase (hTERT). In some embodiments, said composition is formulated for topical administration to a subject. In some embodiments, said composition is formulated as a cream, lotion, gel, or serum. In some embodiments, said composition is formulated for parenteral administration to a subject. In some embodiments, the composition comprises the isolated population of PTH receptor-positive pluripotent stem cells transfected with hTERT in quantities of 10,000 to 10,000,000 cells/mL, such as 10,000, 50,000, 100,000, 500,000, 1,000,000, 5,000,000, or 10,000,000 cells/mL, or an amount within a range defined by any two of the aforementioned values. In some embodiments, said composition reduces telomere shortening, increases cellular self-renewal, increases lifespan, reduces fine lines in the face, reduces wrinkles in the face, or reduces skin aging. In some embodiments, said composition increases telomere activity. In some embodiments, said isolated population of PTH receptor-positive pluripotent stem cells are viable. In some embodiments, said isolated population of PTH receptor-positive pluripotent stem cells are not viable. In some embodiments, said isolated population of PTH receptor-positive pluripotent stem cells are dried, desiccated, or lyophilized. In some embodiments, said composition is a pharmaceutical. In some embodiments, said composition is a cosmetic.

Accordingly, some aspects described herein relate to the following alternatives:

1. A pluripotent stem cell characterized in that it expresses parathyroid hormone type 1 receptor (PTH1R), is 2.5 to 4.5 µm in diameter, such as 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 µm in diameter, or an amount within a range defined by any two of the aforementioned values, forms embryoid-like bodies when cultured, and is capable of differentiation into ectoderm, mesoderm, and endoderm upon culture.

2. The pluripotent stem cell of alternative 1, wherein the cell population is cultured with one or more peptide.

3. The pluripotent stem cell of alternative 2, wherein the peptide is an extracellular matrix (ECM) protein, a cytokine, a growth factor, or an antigen.

4. The pluripotent stem cell of any of alternatives 1-3, wherein the pluripotent stem cell is cultured with retinoic acid and/or with one or more derivative of retinoic acid.

5. The pluripotent stem cell of any of alternatives 1-4, wherein the pluripotent stem cell is transfected with a heterologous gene encoding a peptide.

6. The pluripotent stem cell of alternative 5, wherein the peptide is an extracellular matrix (ECM) protein, a cytokine, a growth factor, or an antigen.

7. The pluripotent stem cell of any one of alternatives 1-6, wherein the pluripotent stem cell is isolated from peripheral blood, seminal fluid, and/or ovarian follicular fluid.

8. An isolated pluripotent stem cell population present in peripheral blood, seminal fluid, and ovarian follicular fluid, which:
   expresses parathyroid hormone type 1 receptor (PTH1R);
   is 2.5 to 4.5 µm in diameter, such as 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 µm in diameter, or an amount within a range defined by any two of the aforementioned values;
   forms embryoid-like bodies when cultured; and
   is capable of differentiation into ectoderm, mesoderm, and endoderm upon culture.

9. The isolated pluripotent stem cell population of alternative 8, wherein the cell population is:
   positive for CD90 and CD133;
   positive/negative for CD29, CD34, CD105, and CD106; and
   negative for SSEA-3, CD200, and CD45.

10. The isolated pluripotent stem cell population of alternatives 8-9, wherein the cell population expresses Sox2 and Oct4.

11. The isolated pluripotent stem cell population of any of alternatives 8-10, wherein the isolated pluripotent stem cell population originates from human, equine, canine, or camel sources.

12. The isolated pluripotent stem cell population of any of alternatives 8-11, wherein the cell population is cultured with a peptide.

13. The isolated pluripotent stem cell population of alternative 12, wherein the peptide is an extracellular matrix (ECM) protein, a cytokine, a growth factor, or an antigen.

14. The isolated pluripotent stem cell population of any of alternatives 8-13, wherein the cell population is cultured with retinoic acid and/or with one or more derivative of retinoic acid.

15. The isolated pluripotent stem cell population of any of alternatives 8-14, wherein the pluripotent stem cell is transfected with a heterologous gene encoding a peptide.

16. The isolated pluripotent stem cell population of alternative 15, wherein the peptide is an extracellular matrix (ECM) protein, a cytokine, a growth factor, or an antigen.

17. An antibody specific for parathyroid hormone type 1 receptor (PTH1R) on a stem cell.

18. The antibody of alternative 17, wherein the antibody is a monoclonal antibody.

19. The antibody of any of alternatives 17-18, wherein the antibody is a humanized antibody.

20. A method for isolating a stem cell population as described in any one of alternatives 1-16, the method comprising:
contacting a sample comprising the stem cell population with an antibody specific for PTH1R, to form an antibody-bound stem cell;
isolating the antibody-bound stem cell; and
releasing the stem cell from the antibody.

21. The method of alternative 20, further comprising:
contacting a sample comprising the antibody-bound stem cell with magnetic beads; and
applying a magnetic field, thereby isolating the antibody-bound stem cell.

22. The method of any one of alternatives 20-21, wherein the sample is obtained from a sample selected from the group consisting of adipose tissue, bone marrow, peripheral blood, seminal fluid, ovarian follicular fluid, and combinations thereof.

23. The method of any one of alternatives 20-22, wherein the isolated stem cell population comprises stem cells that are 2.5 µm in diameter and expressive of stem cell CD markers.

24. The method of any one of alternatives 20-23, wherein the isolated stem cell population comprises stem cells that are isolated in quantities of at least or equal to 10,000, 50,000, 100,000, 500,000, 1,000,000, 5,000,000, or 10,000,000 cells/mL tissue sample, or an amount within a range defined by any two of the aforementioned values.

25. A method for isolating a pluripotent stem cell population as described in any one of alternatives 1-16, the method comprising:
obtaining peripheral blood from an individual;
contacting the peripheral blood with an extracorporeal porous membrane configured to capture the pluripotent stem cell population as described in any one of alternatives 1-16;
applying centrifugal or gravity force or pressure to peripheral blood and the membrane;
capturing the pluripotent stem cell population;
collecting pass-through blood; and
reinfusing the pass-through blood into the individual.

26. The method of alternative 25, wherein the captured pluripotent stem cell population is prepared for subsequent reinfusion into the individual.

27. A method for isolating a stem cell population as described in any one of alternatives 1-16, the method comprising:
contacting a sample comprising the stem cell population with anti-CD45 antibody; and
removing cells unbound by anti-CD45 antibody.

28. The method of alternative 27, wherein the sample is peripheral blood, plasma, or platelet lysate.

29. The method of any one of alternatives 27-28, wherein the isolated stem cell population comprises stem cells that are isolated in quantities of 10,000, 50,000, 100,000, 500,000, 1,000,000, 5,000,000, or 10,000,000 cells/mL tissue sample, or an amount within a range defined by any two of the aforementioned values.

30. A method of improving fertility in a subject comprising:
selecting a subject in need of improved fertility; and
administering a therapeutically effective amount of an isolated population of pluripotent stem cells isolated by the method of any one of alternatives 20-29 or the isolated population of pluripotent stem cells of any one of alternatives 1-16 to said subject.

31. The method of alternative 30, wherein the pluripotent stem cells are autologous.

32. The method of any one of alternatives 30-31, wherein the therapeutically effective amount is an amount sufficient to cause a detectable improvement in ovarian function, oocyte quality, endometrial thickness, endometrial receptivity, or combinations thereof.

33. The method of any one of alternatives 30-32, wherein the therapeutically effective amount of isolated population of pluripotent stem cells is administered by injection into the testicles or uterus.

34. The method of any one of alternatives 30-32, wherein the therapeutically effective amount of isolated population of pluripotent stem cells is administered intravenously to the subject into a uterine artery to promote thickening and receptivity of an endometrial wall.

35. The method of alternative 34, wherein thickening of the endometrial wall is increased by at least 10%, 20%, 30%, 40%, 50%, 60%, 70%, or 80%, or greater or within a range defined by any two of the aforementioned percentages.

36. The method of any one of alternatives 30-32, wherein the therapeutically effective amount of isolated population of pluripotent stem cells is administered intravenously to the subject into an ovarian artery to increase the number and quality of eggs.

37. The method of any one of alternatives 30-36, wherein the pluripotent stem cells are isolated from a sample selected from the group consisting of adipose tissue, bone marrow, peripheral blood, seminal plasma, and ovarian follicular fluid, and/or combinations thereof.

38. A method of targeting a population of pluripotent stem cells isolated by the method of any one of alternatives 20-29 or the isolated population of pluripotent stem cells of any one of alternatives 1-16 to an area of interest comprising expressing parathyroid hormone-related protein in said area.

39. A method of increasing the production of dermal collagen and/or elastin in an area of skin in a subject comprising administering a therapeutically effective amount of a composition comprising an isolated population of pluripotent stem cells isolated by the method of any one of alternatives 20-29 or comprising the isolated population of pluripotent stem cells of any one of alternatives 1-16.

40. The method of alternative 39, wherein the composition is administered by one or more subcutaneous injections.

41. The method of any one of alternatives 39-40, wherein the increased production of dermal collagen and/or elastin reduces fine lines, reduces wrinkles, increases radiance, or increases dermal tightness, and/or combinations thereof.

42. A method for inhibiting hair loss or promoting hair growth comprising administering an effective amount of a composition comprising an isolated population of pluripotent stem cells isolated by the method of any one of alternatives 20-26 or comprising the isolated population of pluripotent stem cells of any one of alternatives 1-16 to a subject in need.

43. The method of alternative 42, wherein the composition is transdermally administered to the subject.

44. The method of alternative 42, wherein the composition is subcutaneously injected to the subject.

45. A method of improving, ameliorating, reversing, or treating a bone disorder comprising administering an effective amount of a composition comprising an isolated population of pluripotent stem cells isolated by the method of any one of alternatives 20-29 or comprising the isolated population of pluripotent stem cells of any one of alternatives 1-16 to a subject in need.

46. The method of alternative 45, wherein the bone disorder is a bone injury.

47. The method of alternative 46, wherein the bone injury is a bone fracture.

48. The method of alternative 47, wherein the bone fracture is a spinous fracture.

49. The method of alternative 45, wherein the bone disorder is osteoporosis.

50. The method of alternative 45, wherein the bone disorder is osteopenia.

51. The method of any one of alternatives 45-50, wherein the composition is subcutaneously injected to the subject.

52. The method of any one of alternatives 45-50, wherein the composition is administered intravenously to the subject.

53. The method of any one of alternatives 45-50, wherein the composition is administered intra-arterially to the subject.

54. The method of alternative 53, wherein the composition is administered into one or more of the uterine, pancreatic, or ovarian artery.

55. A method of improving, ameliorating, inhibiting, reversing, or treating a neurological disorder comprising administering an effective amount of a composition comprising an isolated population of pluripotent stem cells isolated by the method of any one of alternatives 20-29 or comprising the isolated population of pluripotent stem cells of any one of alternatives 1-16 to a subject in need.

56. A method of improving, ameliorating, inhibiting, reversing, or treating metastatic carcinoma comprising administering an effective amount of a composition comprising an isolated population of pluripotent stem cells isolated by the method of any one of alternatives 20-29 or comprising the isolated population of pluripotent stem cells of any one of alternatives 1-16 to a subject in need.

57. A method of preventing, treating, inhibiting, preventing, or ameliorating an autoimmune disorder comprising identifying a subject in need and administering to said subject an effective amount of a composition comprising an isolated population of pluripotent stem cells isolated by the method of any one of alternatives 20-29 or comprising the isolated population of cells comprising stem cells of any one of alternatives 1-16.

58. Peripheral blood derived pluripotent stem cells (PBD-PSCs) for use as a medicament.

59. A method of improving, inhibiting, ameliorating, reversing, or treating diabetes comprising administering an effective amount of a composition comprising an isolated population of pluripotent stem cells isolated by the method of any one of alternatives 20-29 or comprising the isolated population of pluripotent stem cells of any one of alternatives 1-16 to a subject in need.

60. The method of alternative 59, wherein diabetes is Type 1 diabetes.

61. The method of any one of alternatives 59-60, wherein the composition is administered intra-arterially into the pancreatic artery.

62. The method of any one of alternatives 59-61 wherein the composition is administered once every 12 weeks.

63. The method of any one of alternatives 59-62, wherein administration of the composition reduces an amount of daily average insulin usage by the subject.

64. The method of alternative 63, wherein the daily average insulin usage is reduced by 2-10%, 5-20%, 10-30%, 20-40%, 30-50%, 40-60%, 50-70%, 60-80%, 70-90%, or 80-100% or within a range defined by any two of the aforementioned percentages.

65. A method of reducing the average daily insulin dose in a subject suffering from diabetes, comprising administering an effective amount of a composition comprising an isolated population of pluripotent stem cells isolated by the method of any one of alternatives 20-29 or comprising the isolated population of pluripotent stem cells of any one of alternatives 1-16 to a subject in need.

66. The method of alternative 65, wherein diabetes is Type 1 diabetes.

67. The method of any one of alternatives 65-66, wherein the composition is administered intra-arterially into the pancreatic artery.

68. The method of any one of alternatives 65-67 wherein the composition is administered once every 12 weeks.

69. The method of any one of alternatives 65-68, wherein administration of the composition reduces an amount of daily average insulin usage by the subject by 2-10%, 5-20%, 10-30%, 20-40%, 30-50%, 40-60%, 50-70%, 60-80%, 70-90%, or 80-100% or within a range defined by any two of the aforementioned percentages.

70. A method for growing an isolated population of pluripotent stem cells on a matrix, comprising:
    isolating a population of pluripotent stem cells from a sample by the method of any one of alternatives 20-29;
    contacting a nanofiber matrix with the isolated pluripotent stem cells; and
    growing the isolated pluripotent stem cells on the nanofiber matrix;
    wherein a matrix comprising pluripotent stem cells is produced.

71. The method of alternative 70, wherein the nanofiber matrix comprises polymer fibers, including, for example, polydimethylsiloxane, polyglycerol sebacate, polycaprolactone, polylactic acid, polyglycolic acid, cellulose, alginate, agar, agarose, collagen I, collagen IV, hyaluronic acid, fibrin, poly-L-lactide, and/or poly(lactic-co-glycolic acid).

72. The method of alternative 71, wherein the polymer fibers are electrospun.

73. The method of any one of alternatives 71-72, wherein the polymer fibers are of a thickness that is at least or equal to 200, 300, 400, 500, 600, or 700 μm or within a range defined by any two of the aforementioned thicknesses.

74. The method of any one of alternatives 70-73, wherein the pluripotent stem cells bind to and lay down in the matrix within 2-40 minutes.

75. The method of any one of alternatives 70-74, wherein the matrix comprising pluripotent stem cells is used for injecting into joints or bones.

76. The method of any one of alternatives 70-74, wherein the matrix comprising pluripotent stem cells is used for covering a wound.

77. A method of improving, ameliorating, reversing, inhibiting, or treating macular degeneration comprising administering an effective amount of a composition comprising an isolated population of pluripotent stem cells isolated by the method of any one of alternatives 20-29 or comprising the isolated population of pluripotent stem cells of any one of alternatives 1-16 to a subject in need.

78. The method of alternative 77, wherein macular degeneration is dry or wet macular degeneration.

79. The method of any one of alternatives 77-78, wherein the composition is administered by intravenous, intravitreal, intraocular, subconjunctival, retrobulbar, or sub-orbital injection.

80. The method of any one of alternatives 77-79 wherein the composition is administered once every 12 weeks.

81. The method of any one of alternatives 77-80, wherein administration of the composition improves visual acuity in the subject.

82. The method of alternative 81, wherein the visual acuity is improved to 20/20, 20/30, 20/40, 20/50, 20/60, 20/70, 20/80, 20/90, or 20/100 or within a range defined by any two of the aforementioned amounts.

83. A method of treating, reversing, inhibiting, or improving an age-related disorder in a subject comprising:
   optionally, isolating a population of parathyroid hormone (PTH) receptor-positive pluripotent stem cells from the subject;
   transfecting an isolated population of PTH receptor-positive pluripotent stem cells, preferably isolated from said subject, with a human telomerase reverse transcriptase (hTERT) gene to generate hTERT transfected PTH receptor-positive pluripotent stem cells; and
   administering a therapeutically effective amount of the hTERT transfected PTH receptor-positive pluripotent stem cells to said subject.

84. The method of alternative 83, wherein said therapeutically effective amount is an amount sufficient to reduce telomere shortening, increase cellular self-renewal, increase lifespan, reduce fine lines or wrinkles, and/or reduce aging in said subject.

85. The method of alternative 83, wherein said age-related disorder is osteoporosis, arthrosis, glucose intolerance, insulin resistance, reduced heart, circulatory, or lung function, cardiovascular disease, a neurodegenerative disease, loss of memory, loss of neuromuscular coordination, and/or decrease of longevity.

86. The method of alternative 83, wherein telomerase activity is recovered in cells of said subject.

87. The method of alternative 83, wherein said population of PTH receptor-positive pluripotent stem cells are isolated from peripheral blood, seminal fluid, or ovarian follicular fluid.

88. The method of alternative 83, wherein transfecting said population of PTH receptor-positive stem cells comprises non-viral transfection.

89. The method of alternative 83, wherein transfecting said population of PTH receptor-positive stem cells comprises chemical-based transfection, viral transfection, particle-based transfection, or electroporation.

90. The method of alternative 83, wherein the hTERT transfected PTH receptor-positive pluripotent stem cells are administered to the subject once weekly, once monthly, or once annually.

91. A composition comprising an isolated population of parathyroid hormone (PTH) receptor-positive pluripotent stem cells transfected with human telomerase reverse transcriptase (hTERT).

92. The composition of alternative 91, wherein said composition is formulated for topical administration to a subject.

93. The composition of alternative 92, wherein said composition is formulated as a cream, lotion, gel, or serum.

94. The composition of alternative 91, wherein said composition is formulated for parenteral administration to a subject.

95. The composition of alternative 91, wherein the composition comprises the isolated population of PTH receptor-positive pluripotent stem cells transfected with hTERT in quantities of 10,000 to 10,000,000 cells/mL, such as 10,000, 50,000, 100,000, 500,000, 1,000,000, 5,000,000, or 10,000,000 cells/mL, or an amount within a range defined by any two of the aforementioned values.

96. The composition of alternative 91, wherein said composition reduces telomere shortening, increases cellular self-renewal, increases lifespan, reduces fine lines in the face, reduces wrinkles in the face, and/or reduces skin aging.

97. The composition of alternative 91, wherein said composition increases telomere activity.

98. The composition of alternative 91, wherein said isolated population of PTH receptor-positive pluripotent stem cells are viable.

99. The composition of alternative 91, wherein said isolated population of PTH receptor-positive pluripotent stem cells are not viable.

100. The composition of alternative 91, wherein said isolated population of PTH receptor-positive pluripotent stem cells are dried, desiccated, or lyophilize.

101. The composition of alternative 91, wherein said composition is a pharmaceutical.

102. The composition of alternative 91, wherein said composition is a cosmetic.

These features, together with other features herein further explained, will become obvious through a reading of the following description of the drawings and detailed description.

BRIEF DESCRIPTION OF THE DRAWINGS

In addition to the features described above, additional features and variations will be readily apparent from the following descriptions of the drawings and exemplary embodiments. It is to be understood that these drawings depict typical embodiments, and are not intended to be limiting in scope.

FIG. 4A depicts PTHR positive cells, FIG. 4B depicts CD133 positive cells, and FIG. 4C depicts PTHR/CD90 positive cells.

FIG. 23A shows the fracture prior to treatment. FIG. 23B shows treatment of a coronal cervical fracture using a PBD-PSC treatment. The left image shows the fracture prior to treatment, and the right image shows the fracture 4 months after PBD-PSC treatment. FIG. 23C shows treatment of a sagittal cervical fracture using a PBD-PSC treatment. The left image shows the fracture prior to treatment, and the right image shows the fracture 4 months after PBD-PSC treatment.

DETAILED DESCRIPTION

Figure 1:
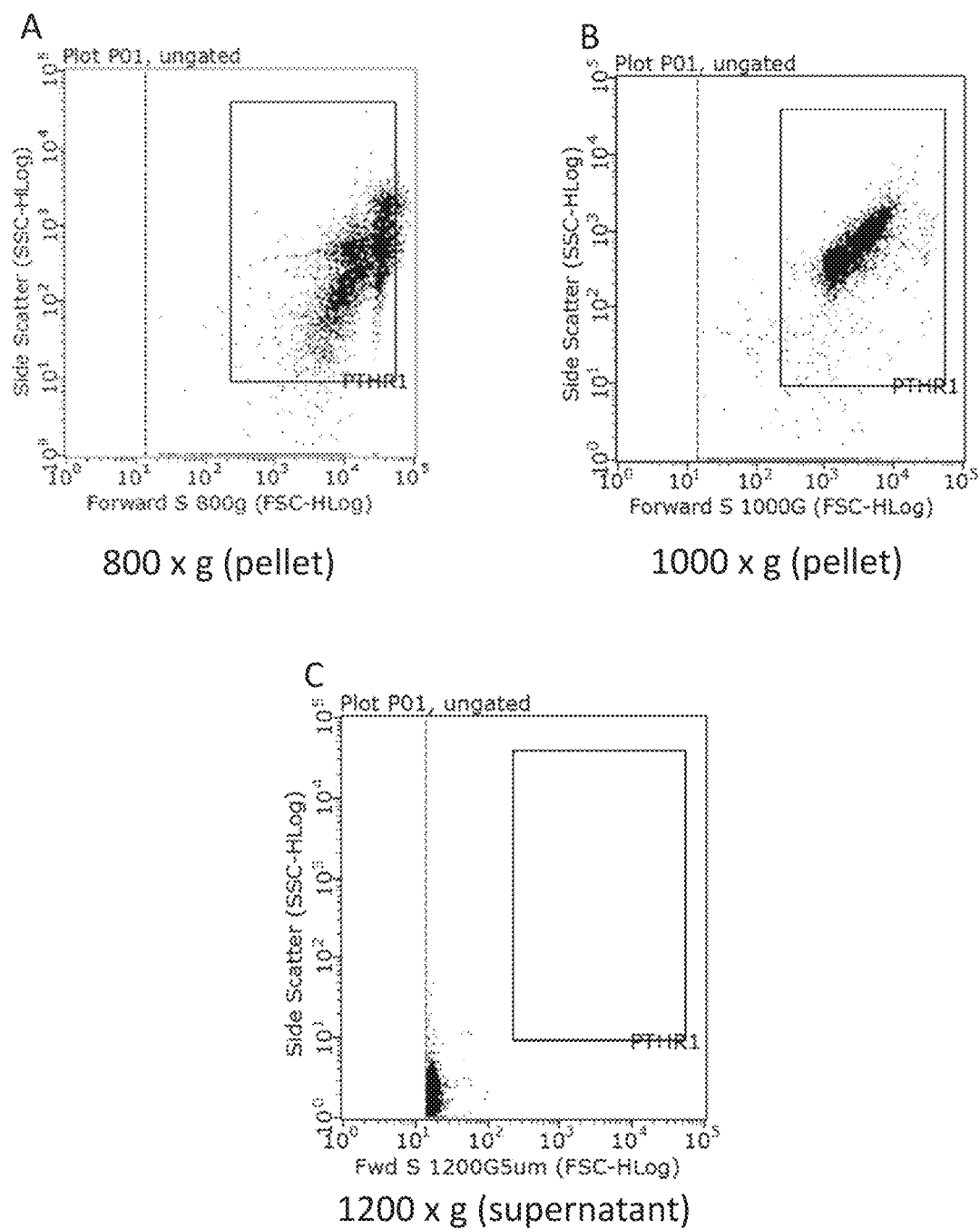
FIG. 1 depicts the characterization of PBD-PSCs described herein. The flow cytometric results of parathyroid hormone 1 receptor (PTH1R) positive cells after centrifugation and filtration at 800×g (Panel A), 1000×g (Panel B), and 1200×g (Panel C).
Figure 2:
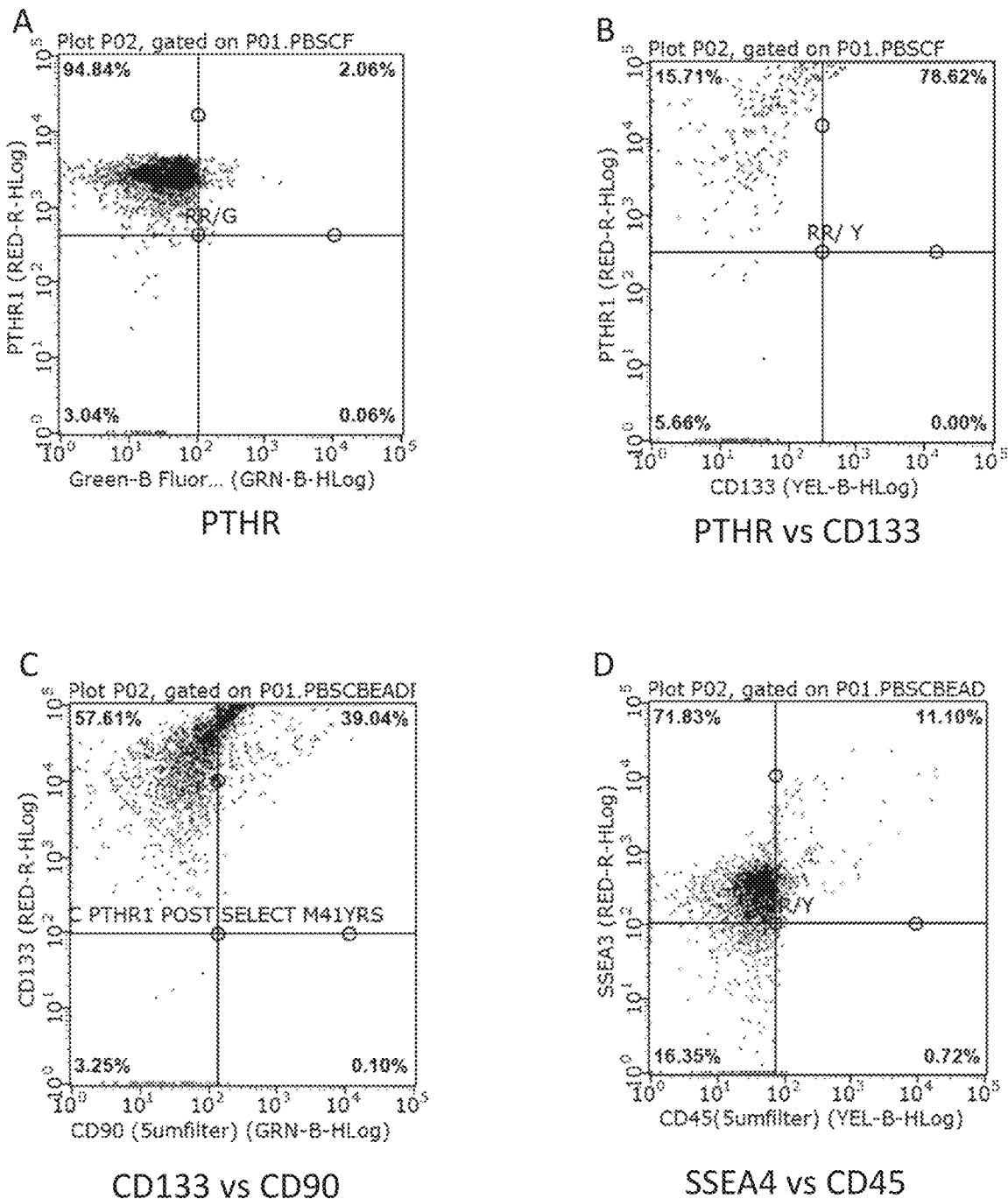
FIG. 2 depicts the characterization of PBD-PSCs described herein by flow cytometry. PTH1R positive cells from peripheral blood are shown in Panel A. Panel B compares PTH1R positive cells and CD133 positive cells. Panel C compares CD133 positive cells and CD90 positive cells. Panel D compares SSEA4 positive cells and CD45 positive cells.
Figure 3:
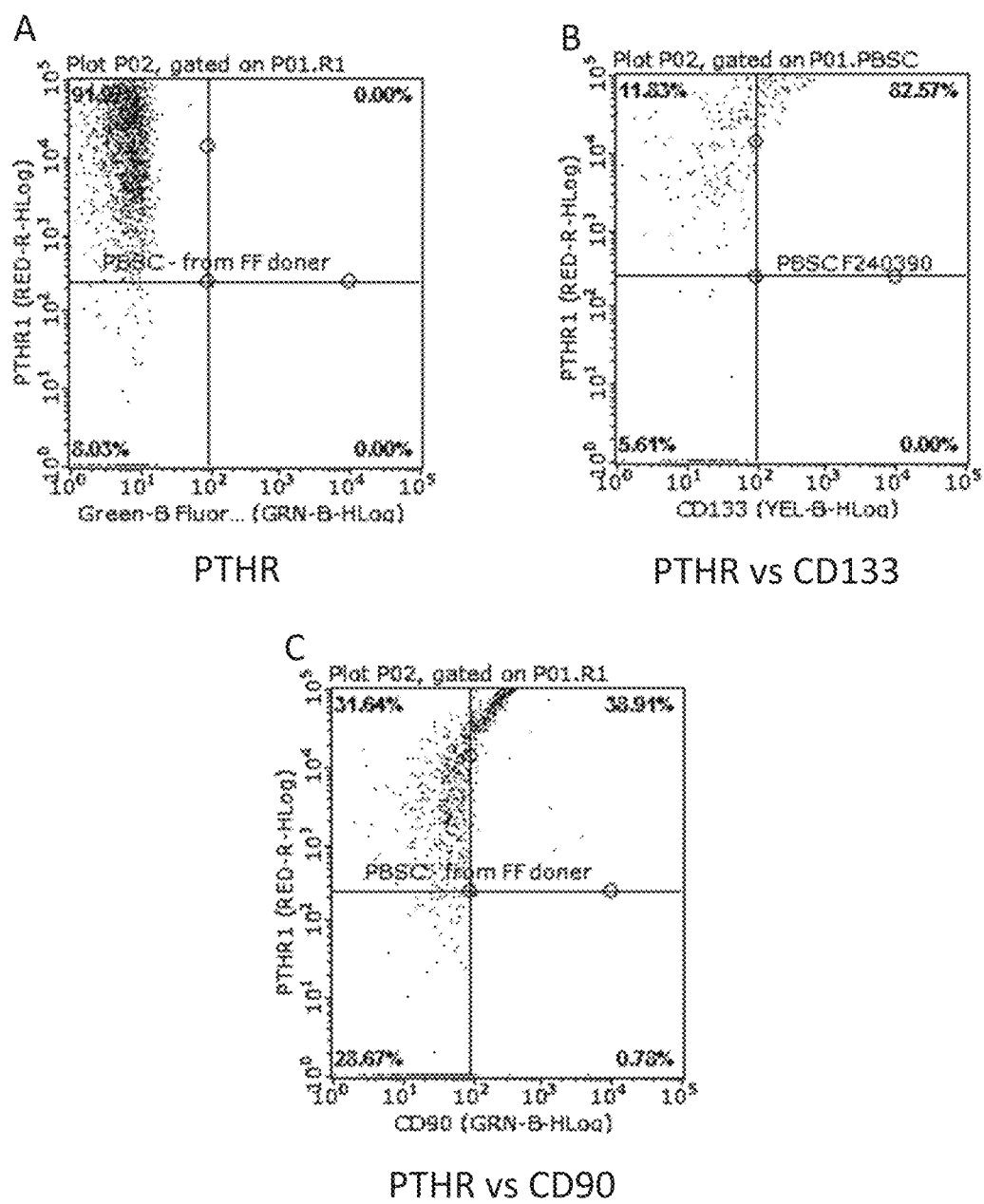
FIG. 3 shows the characterization of PTH1R positive cells from ovarian follicular fluid after centrifugation and filtration. Panel A shows the PTH1R positive cells. Panel B compares PTH1R positive cells and CD133 positive cells. Panel C compares PTH1R positive cells and CD90 positive cells.
Figure 4A:
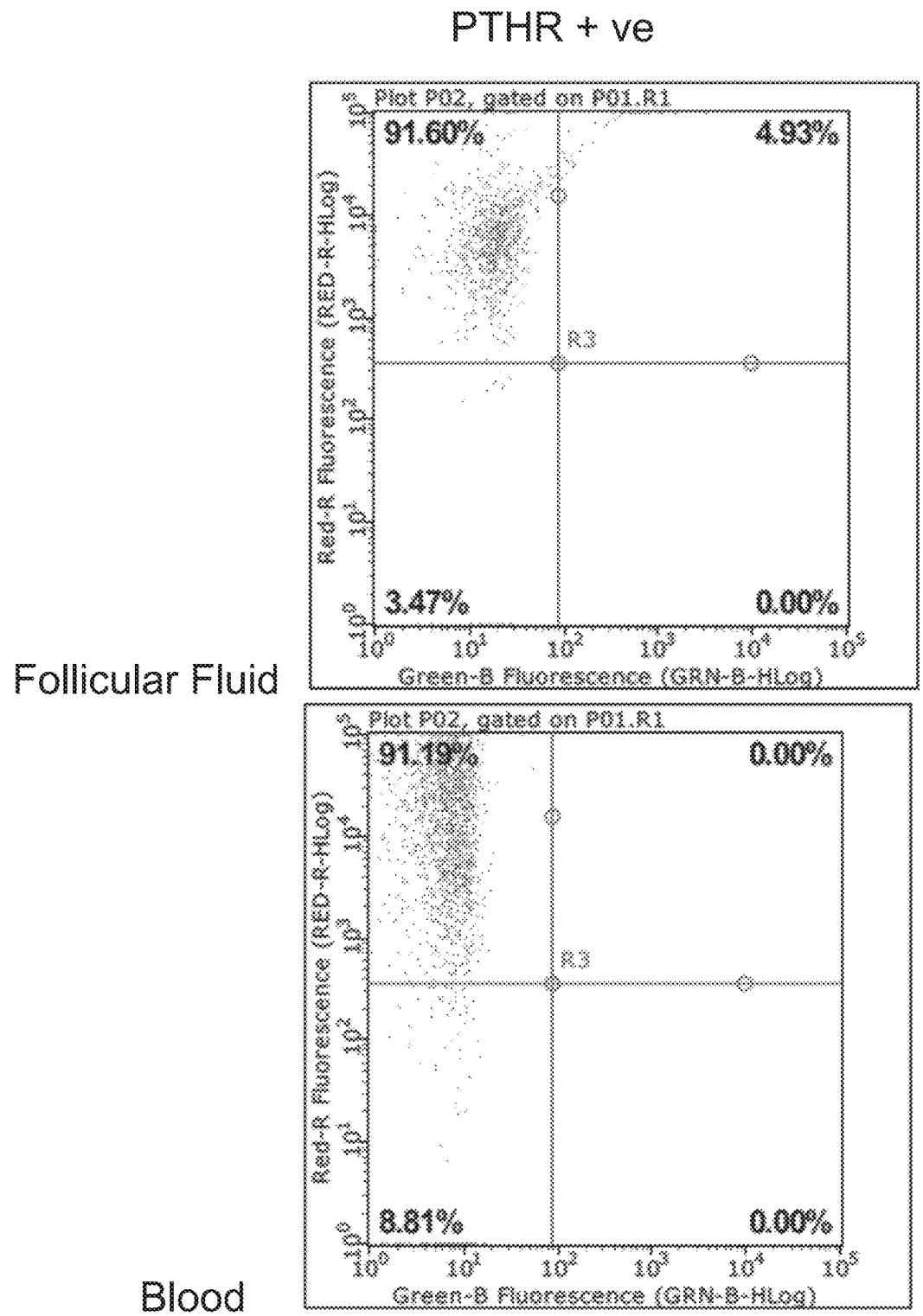
FIGS. 4A-4C depict the characterization of PTH1R positive cells from ovarian follicular fluid and from peripheral blood.
Figure 4B:
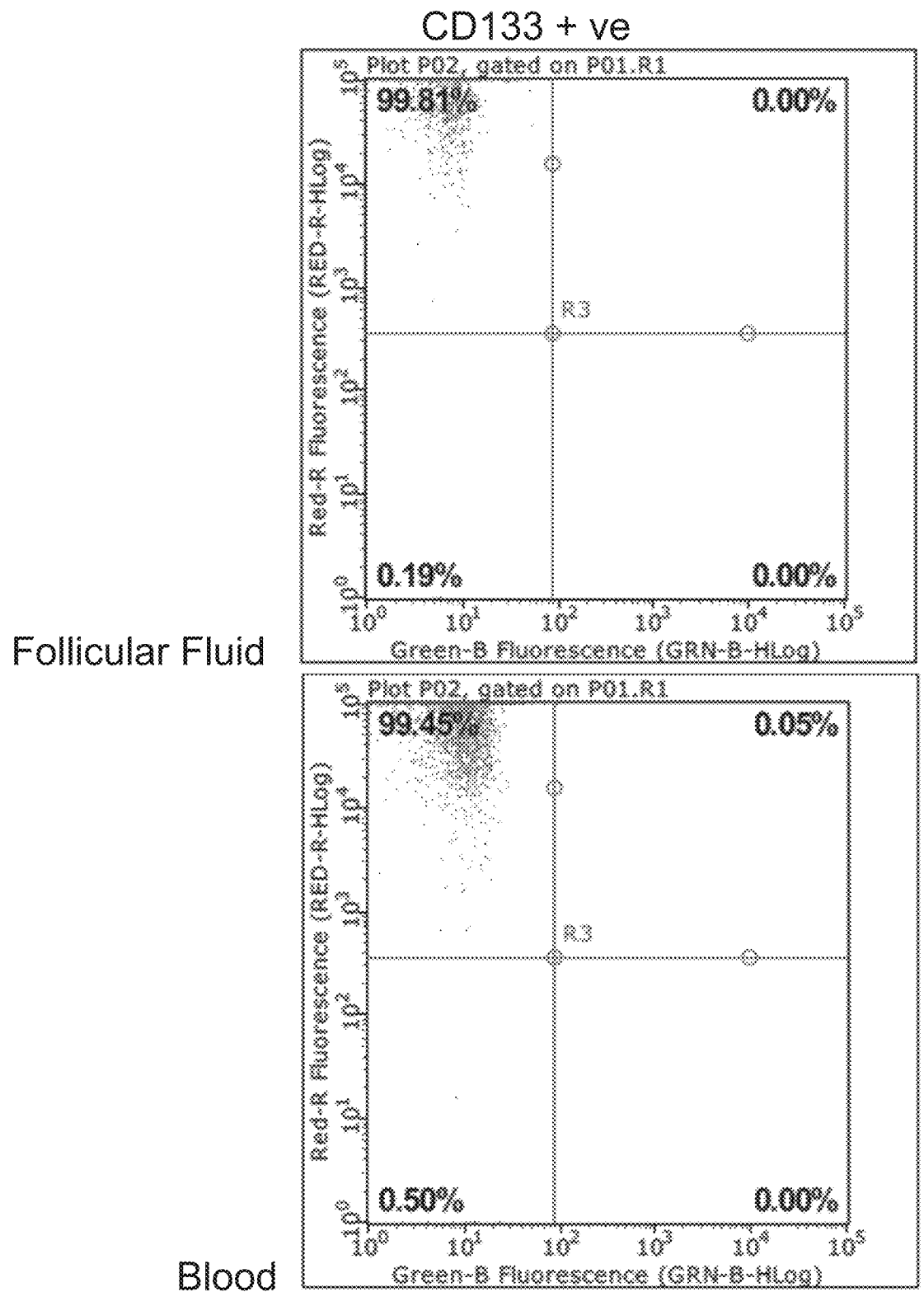
Figure 4C:
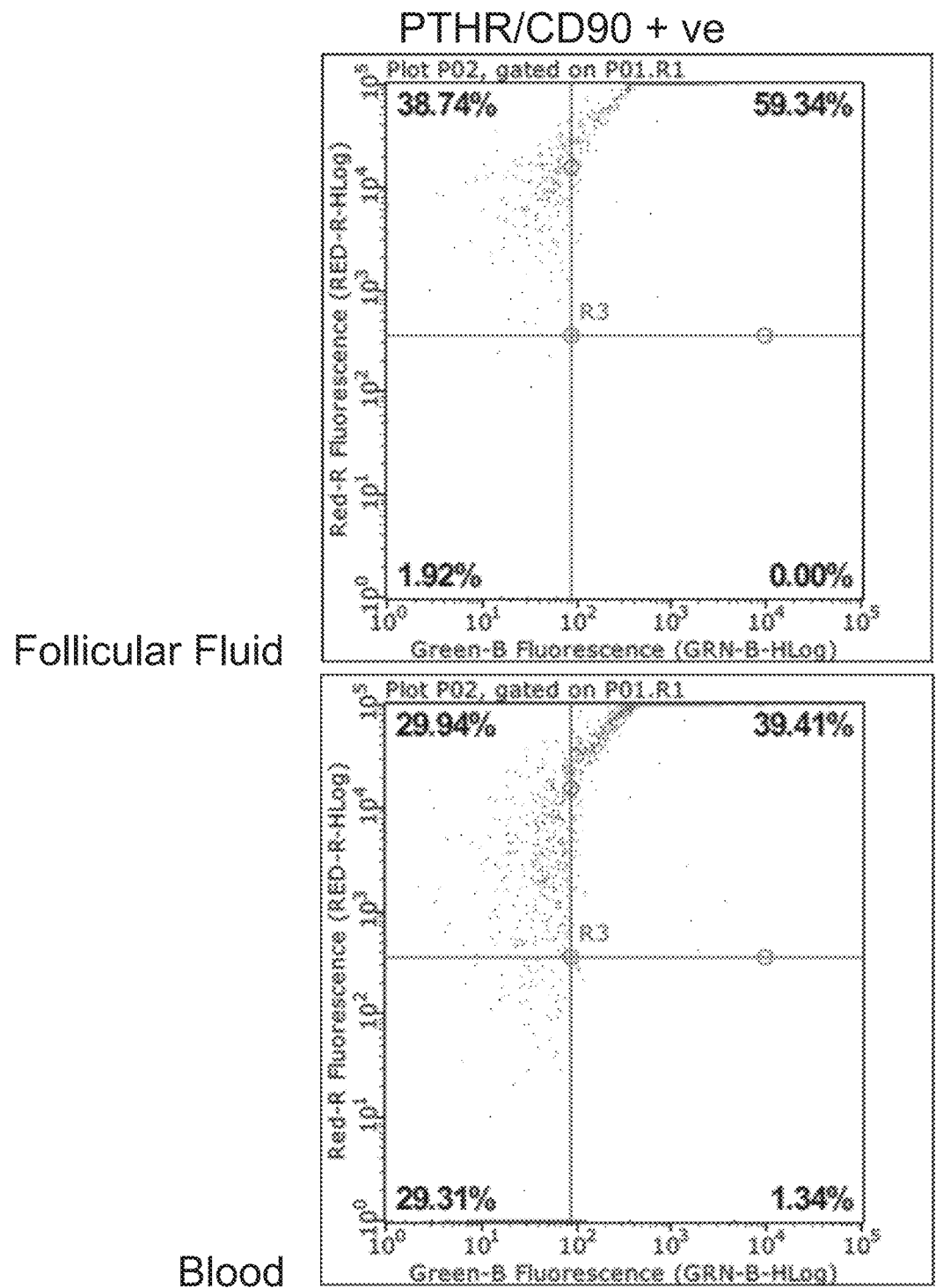
Figure 5A:
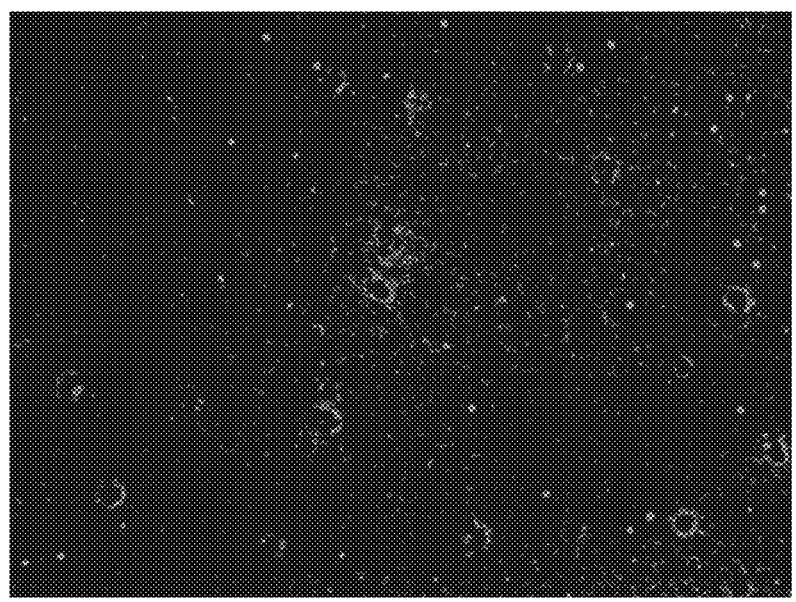
FIGS. 5A-5E depict a micrograph of PBD-PSCs as described herein, with antibody staining against PTH Receptor (FIG. 5A), CD90 (FIG. 5B), CD133 (FIG. 5C), SSEA-4 (FIG. 5D), and CD45 (FIG. 5E).
Figure 5B:
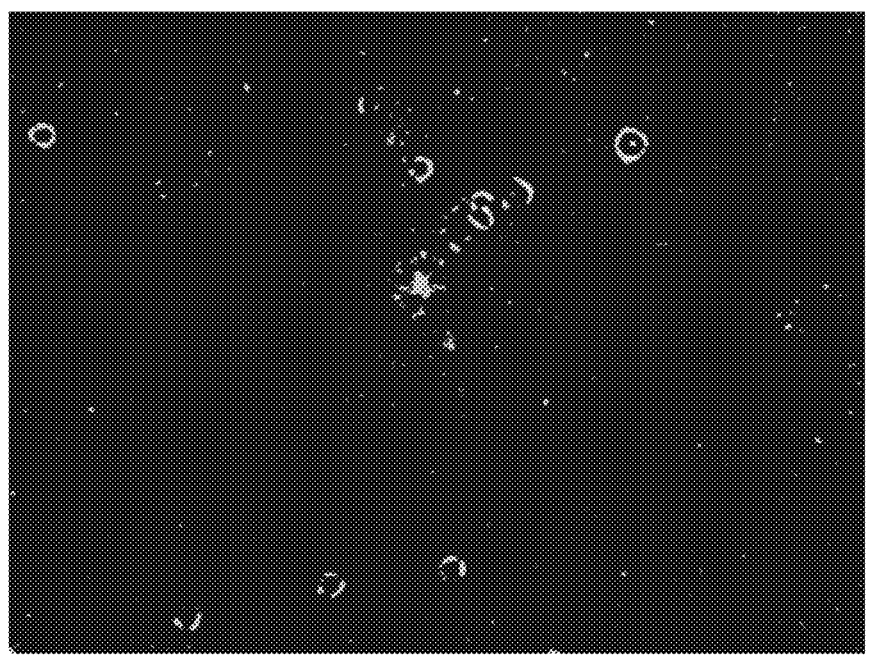
Figure 5C:
Figure 5D:
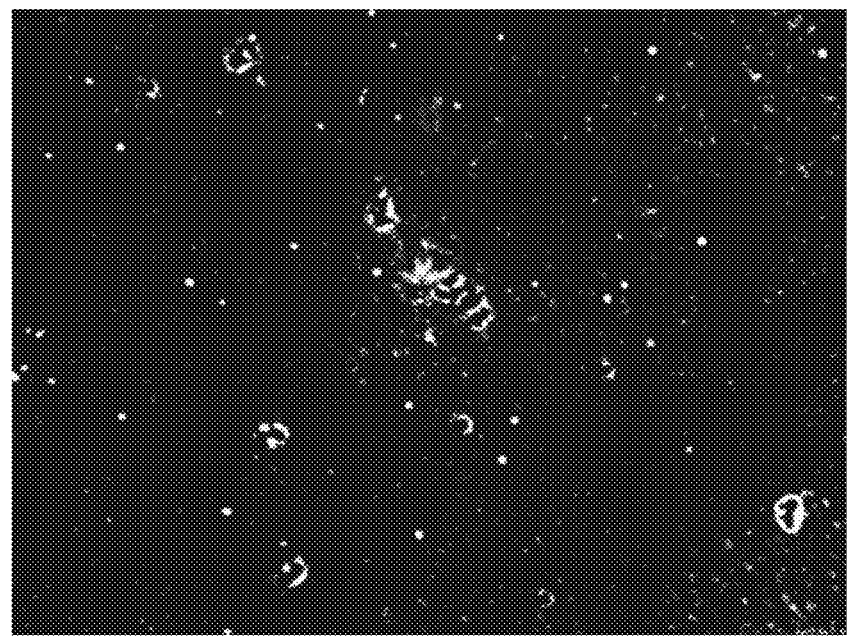
Figure 5E:
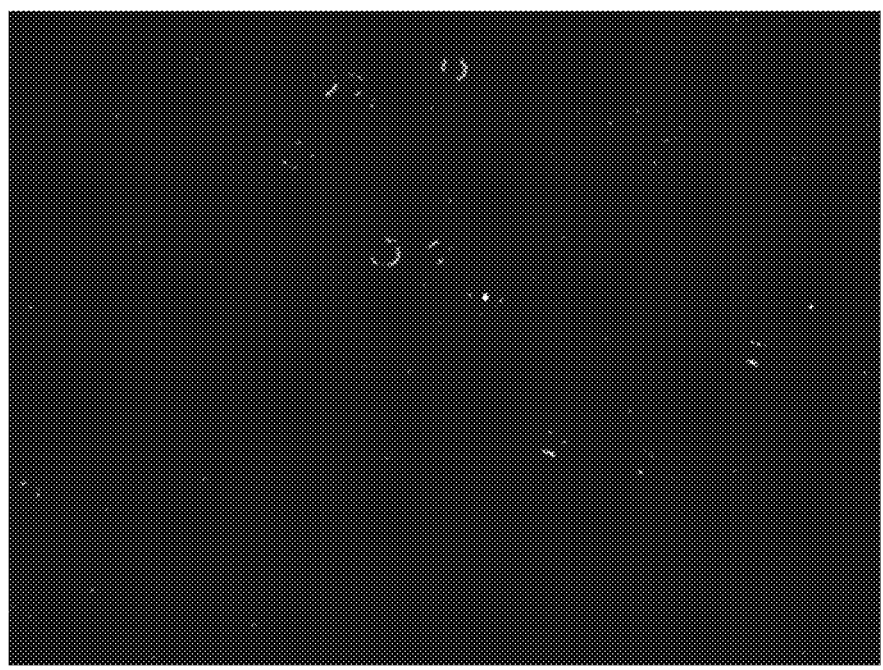

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Peripheral blood derived pluripotent stem cells (PBD-PSCs) are very small stem cells from 2.5-4.5 μm in diameter, such as 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 μm in diameter, or an amount within a range defined by any two of the aforementioned values. PBD-PSCs are very primitive stem cells that have a high potency for differentiating into a variety of specialized lineages. Accordingly, PBD-PSCs have a high propensity for applications in the areas of regenerative medicine and in particular, for anti-aging therapeutics. In particular, PBD-PSCs are a powerful tool for a number of applications, including, for example: allogenic regenerative cell therapy, wherein donor cells are used for differentiation and are capable of releasing growth factors for the repair of damaged tissue; autologous regenerative cell therapy, wherein the patient's own cells are used for reprogramming, expansion, and/or differentiation for the treatment of damaged tissue by permanently integrating into the tissue; and tissue engineering, wherein a patient's own cells are placed upon a scaffold to create a neo-tissue, which is then engrafted onto damaged tissue to repair the tissue. PBD-PSCs are characterized in that they are highly expressive of PTH1R. Accordingly, in some aspects, PBD-PSCs are also referred to herein as PTH1R-positive stem cells.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

The articles "a" and "an" are used herein to refer to one or to more than one (for example, to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In some embodiments, the "purity" of any given agent (e.g., antibody, polypeptide binding agent) in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

As used herein, the terms "function" and "functional" and the like refer to a biological, enzymatic, or therapeutic function.

The term "isolated" is meant material that is substantially or essentially free from components that normally accompany it in its native state. For example, an "isolated stem cell" or "isolated population of stem cells" as used herein, includes a stem cell or population of stem cells that has been purified from sample material, including other cells, debris, or extraneous sample material from its naturally-occurring state, Alternatively, an "isolated stem cell" or "isolated population of stem cells" and the like, as used herein, includes the in vitro, extracorporeal, or other isolation and/or purification of a cell or population of cells from its natural environment, and from association with other components of the sample or material in which it occurs. In some embodiments, isolated means that the component is not significantly associated with in vivo substances.

The practice of the present disclosure will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, el al, Molecular Cloning: A Laboratory Manual ($3^{rd}$ Edition, 2000); DNA Cloning: A Practical Approach, vol. 1 & II (D. Glover, ed.); Oligonucleotide Synthesis (N. Gait, ed., 1984); Oligonucleotide Synthesis: Methods and Applications (P. Herdewijn, ed., 2004); Nucleic Acid Hybridization (B. Hames & S. Higgins, eds., 1985); Nucleic Acid Hybridization: Modern Applications (Buzdin and Lukyanov, eds., 2009); Transcription and Translation (B. Hames & S. Higgins, eds., 1984); Animal Cell Culture (R. Freshney, ed., 1986); Freshney, R. I. (2005) Culture of Animal Cells, a Manual of Basic Technique, $5^{th}$ Ed. Hoboken N.J., John Wiley & Sons; B. Perbal, A Practical Guide to Molecular Cloning ($3^{rd}$ Edition 2010); Farrell, R., RNA Methodologies: A Laboratory Guide for Isolation and Characterization ($3^{rd}$ Edition 2005).

As used herein, the term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain molecules, and antibody fragments (e.g., Fab or F(ab')$_2$, and Fv). For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, Conn., 1994, page 71 and Chapter 6.

In some embodiments, an antibody against PBD-PSCs is provided. In some embodiments, the antibody is a monoclonal or polyclonal antibody. In some embodiments, the antibody is a humanized antibody. An "isolated antibody" is an antibody that is not associated with naturally-associated components, including other naturally-associated antibodies, that accompany it in its native state and is free of other proteins from the same species. Furthermore, the isolated antibody is expressed by a cell from a different species or does not occur in nature. The term human antibody includes all antibodies that have one or more variable and constant regions derived from human immunoglobulin sequences. A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. A chimeric antibody refers to an antibody that contains one or more regions from one antibody and one or more regions from one or more other antibodies. In addition, fragments of antibodies can be readily prepared. Thus, as described herein are provided antibodies and fragments thereof against PBD-PSCs.

As used herein, the term "treatment" refers to an intervention made in response to a disease, disorder or physiological condition manifested by a subject, particularly a subject suffering from an age-related disorder or a disorder exhibition degenerative tissue or cellular effects. Such disorders can include, but are not limited to, skin disorders, hair loss and hair disorders, diabetes, including Type 1 Diabetes, bone disorders and injury including osteoporosis, osteopenia, and/or bone fractures, infertility, malignant cancers, autoimmune disorders, macular degeneration, and other disorders involving loss of regeneration, among others described herein and known in the art. The aim of treatment may include, but is not limited to, one or more of the alleviation or prevention of symptoms, slowing or stopping the progression or worsening of a disease, disorder, or condition and the remission of the disease, disorder or condition. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments, treatments reduce, alleviate, or eradicate the symptom(s) of the disease(s).

As used herein, the term "prevention" refers to any activity that reduces the burden of the individual later expressing disease symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications.

As used herein, the term "improving" refers to a process or effect of treating or alleviating a disease, disorder, or condition as described herein. As used herein, the term "inhibiting" generally refers to preventing, blocking, stopping, or slowing progression in any manner, including partially or completely reversing.

As used herein, the term "reversing" means that the progress of a disease, disorder, or symptom of a disease or disorder is fully or partially improves the disease, disorder, or symptoms, or that restores health of a subject to a condition prior to onset of a disease, disorder, or symptom, in full or in part. For example, reversing can include partially restoration of health by an incremental amount, such as improvement by 1%, 2%, 3%, 4%, 5%, 10%, 20%, 25%, 50%, 75%, 80%, 90%, 95%, or 99%, or an amount within a range defined by any two of the aforementioned values, or a complete restoration of health.

The term "therapeutically effective amount" is used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being administered the therapy. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As used herein, the term "osteoporosis" refers to the condition characterized by reduced bone mass and disruption of bone architecture, resulting in increased bone fragility and increased fracture risk, and decreased calcification or density of bone. Osteoporosis is a thinning of the bones with reduction in bone mass due to depletion of calcium and bone protein. In osteoporotic patients, bone strength is abnormal, with a resulting increase in the risk of fracture. The fracture can be in the form of cracking (as in a hip fracture) or collapsing (as in a compression fracture of the spine). The spine, hips, and wrists are common areas of osteoporosis-induced bone fractures, although fractures also can occur in other skeletal areas. Unchecked osteoporosis can lead to changes in posture, physical abnormality and decreased mobility. Osteoporosis can be identified by bone mineral density measurements. As used herein, "osteopenia" refers to an imbalance between bone formation and bone resorption with the rate of resorption exceeding the rate of formation thereby negatively impacting the biological and structural integrity of the bone, resulting in decreased calcification or density of bone.

As used herein, the term "diabetes mellitus" refers to a disease caused by a relative or absolute lack of insulin leading to uncontrolled carbohydrate metabolism, commonly simplified to "diabetes," though diabetes mellitus should not be confused with diabetes insipidus. As used herein, "diabetes" refers to diabetes mellitus, unless otherwise indicated. A "diabetic condition" includes pre-diabetes and diabetes. Type 1 diabetes (sometimes referred to as "insulin-dependent diabetes" or "juvenile-onset diabetes") is an auto-immune disease characterized by destruction of the pancreatic 13 cells that leads to a total or near total lack of insulin. In type 2 diabetes (T2DM; sometimes referred to as "non-insulin-dependent diabetes" or "adult-onset diabetes"), the body does not respond to insulin, though it is present. As used herein, the term "metabolic condition" is used to refer to type 1 diabetes, type 2 diabetes, pre-diabetes, and diabetes complications.

Symptoms of diabetes include: excessive thirst (polydipsia); frequent urination (polyuria); extreme hunger or constant eating (polyphagia); unexplained weight loss; presence of glucose in the urine (glycosuria); tiredness or fatigue; changes in vision; numbness or tingling in the extremities (hands, feet); slow-healing wounds or sores; and abnormally high frequency of infection. Diabetes may be clinically diagnosed by a fasting plasma glucose (FPG) concentration of greater than or equal to 7.0 mmol/L (126 mg/dL), or a plasma glucose concentration of greater than or equal to 11.1 mmol/L (200 mg/dL) at about two hours after an oral glucose tolerance test (OGTT) with a 75 g load.

As used herein, the term "hair loss" refers to elimination of hair from scalps or loosening or thinning of hair. The expression "preventing hair loss" means preventing and inhibiting such hair loss, and the expression "promoting hair growth" means promoting formation of new hair or keeping the existing hair growing healthily.

"Skin damage" or "skin disorder" as described herein, can refer to damage to the skin that can be caused by aging, sun damage, cancer, skin disorder or skin diseases that can cause irritation of the skin. Without being limiting, the "skin diseases" and/or "skin disorders" can include rhytide, non-enzymatic glycosylation of the skin, sun damage, smoking damage, fibrosis of the skin, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea congloate, synovitis-acne-pustulosis-hyperostosis-osteomyelitis syndrome (SAPHO syndrome), steroid rosacea, tar acne, skin cancer, tropical acne, psoriasis, including plaque psoriasis, guttate psoriasis, inverse psoriasis, pustular psoriasis, erythrodermic psoriasis, nail psoriasis, and/or psoriatic arthritis, and/or combinations and/or variations thereof. In some embodiments described herein, a method of treating, inhibiting, preventing, or ameliorating a disease or disease condition a subject in need is provided. The subject can have a disease or disease condition affecting the skin as described herein.

"Hair and scalp disorders" are diseases that affect the hair and scalp and are also described herein. Diseases that affect hair and scalp can include but are not limited to: alopecia, androgenic alopecia, hirsutism, hair shaft disorders, inflammation, acromegaly, eczema, psoriasis, impetigo, atopic dermatitis, darier disease, and/or folliculitis. Common causes for scalp disorders can include but are not limited to: acromegaly, atopic dermatitis, darier disease, eczema, fragile X syndrome, impetigo, pachydermoperiostosis, psoriasis and/or Rosenthal-Kloepfer syndrome. In some embodiments described herein, a method of treating, inhibiting, preventing, or ameliorating a disease or disease condition in a subject in need is provided. The subject can have a disease affecting the skin and scalp. In some embodiments the subject suffers from alopecia, androgenic alopecia, hirsutism, hair shaft disorders, inflammation, acromegaly, eczema, psoriasis, impetigo, atopic dermatitis, darier disease, and/or folliculitis. In some embodiments, the subject suffers from acromegaly, atopic dermatitis, darier disease, eczema, fragile X syndrome, impetigo, pachydermoperiostosis, psoriasis and/or Rosenthal-Kloepfer syndrome. In some embodiments, the protocol includes administering a formulation to the subject in need. In some embodiments, the formulation is within a hair cream, a hair gel, a scalp lotion, a shampoo, conditioner, hair spray or a hair mousse.

"Nail diseases" are disorders or diseases that affect the nail, nail bed or cuticle region and are also described herein. Diseases that affect the nail and surrounding skin area such as the cuticle can lead to infection or inflammation that could require medical assistance. Diseases that infect the nail, nail bed and/or cuticle can include but are not limited to: onychia, onchyocryptosis, onychodystophy, onychogryposis, onycholysis, onychomadesis, onychomycosis, tinea unguium, onychophosis, onychoptosis, onchorrhexis, paronychia, Koilonychia, subungual hematoma, onychomatricoma, nail pemphigus, erythronychia and/or melanonychia. In some embodiments described herein, a method of treating, inhibiting, preventing, or ameliorating a disease or disease condition a subject in need is provided. The subject can have a disease or disease condition affecting the nails, nail bed and/or cuticles. In some embodiments the subject suffers from alopecia, androgenic alopecia, hirsutism, hair shaft disorders, inflammation, acromegaly, eczema, psoriasis, impetigo, atopic dermatitis, darier disease, and/or folliculitis. In some embodiments, the subject suffers from onychia, onchyocryptosis, onychodystophy, onychogryposis, onycholysis, onychomadesis, onychomycosis, tinea unguium, onychophosis, onychoptosis, onchorrhexis, paronychia, Koilonychia, subungual hematoma, onychomatricoma, nail pemphigus, erythronychia and/or melanonychia. In some embodiments, the treating, inhibiting, preventing, or ameliorating includes administering a formulation to the subject in need. In some embodiments, the formulation is within a skin cream, a lotion, a cuticle cream or a nail polish.

"Autoimmune disorders" or "autoimmune diseases" as used herein describes diseases caused by an immune response against the body's own cells or tissues. Autoimmune disorders result in destruction of one or more types of body tissues, abnormal growth of an organ or organs, or changes in organ function or functions. The disorders may affect only one organ or tissue type or may affect multiple organs and tissue types. In addition, a person may experience one or more autoimmune disorders at the same time. Organs and tissues commonly affected by autoimmune disorders include blood components such as red blood cells, blood vessels, connective tissues, endocrine glands such as the thyroid or pancreas, muscles, joints, and/or skin.

Autoimmune disorders are often categorized into two general types: (1) systemic autoimmune diseases (e.g., disorders that damage many organs or tissues), and (2) localized autoimmune diseases (e.g., disorders that damage only a single organ or tissue). However, the effect of localized autoimmune diseases can be systemic by indirectly affecting other body organs and systems. Systemic autoimmune diseases include without limitation: rheumatoid arthritis, which can affect joints, and possibly lung and skin; lupus, including systemic lupus erythematosus (SLE), which can affect skin, joints, kidneys, heart, brain, and/or red blood cells, as well as other tissues and organs; scleroderma, which can affect skin, intestine, and/or lungs; Sjogren's syndrome, which can affect salivary glands, tear glands, and/or joints; Goodpasture's syndrome, which can affect lungs and/or kidneys; Wegener's granulomatosis, which can affect sinuses, lungs, and/or kidneys; polymyalgia rheumatica, which can affect large muscle groups, and/or temporal arteritis/giant cell arteritis, which can affect arteries of the head and/or neck. Localized autoimmune diseases include without limitation: Type 1 Diabetes Mellitus, which affects pancreas islets; Hashimoto's thyroiditis and/or Graves' disease, which affect the thyroid; celiac disease, Crohn's diseases, and/or ulcerative colitis, which affect the gastrointestinal tract; multiple sclerosis (MS) and Guillain-Barre syndrome, which affect the central nervous system; Addison's disease, which affects the adrenal glands; primary biliary sclerosis, sclerosing cholangitis, and/or autoimmune hepatitis, which affect the liver; and Raynaud's phenomenon, which can affect the fingers, toes, nose, ears. Additional examples of autoimmune disorders include: pernicious anemia; Addison's disease; dermatomyositis; myasthenia gravis (MG); Reiter's syndrome; Pemphigus vulgaris; scleroderma and/or CREST syndrome; autoimmune hemolytic anemia; autoimmune thrombocytopenic purpura; ankylosing spondylitis; vasculitis; and/or amyotrophic lateral sclerosis (Lou Gehrig's disease).

Symptoms of autoimmune disorders can vary widely depending on the type of disease. Commonly observed symptoms or disease states include: fatigue, dizziness, malaise, and/or fever. Other symptoms or disease states that may be observed in one or more autoimmune disorders include: chills, weight loss, skin rashes, vasculitis, polyarthralgia, patchy hair loss, oral and/or nasal sores, lymph-node enlargement, gastric problems, generalized pain, which may be located in the joints in the case of arthritis, enlarged glands, such as the thyroid in the case of Grave's disease, heart palpitations, dermal blisters and/or lesions, muscle weakness. In some embodiments, the treating, inhibiting, preventing or ameliorating includes administering a formulation to the subject to prevent, treat, or ameliorate an autoimmune disorder. In some embodiments, the treating, inhibiting, preventing, or ameliorating includes administering a formulation for the treatment of a symptom of the autoimmune disorder.

"Age-related disorder" or "age-related disease" as used herein, refers to disorders or diseases, wherein aging is a major risk factor. Age-related diseases or disorders include, for example, abnormal proliferative diseases, cancer, degenerative diseases, neuron degenerating disease (Alzheimer's disease, Parkinson's disease, stroke), loss of memory, loss of neuromuscular coordination, decreased longevity, reduced heart function, reduced circulatory function, reduced lung function, atherosclerosis, hypertension, osteoarthritis, osteoporosis, sarcopenia, loss of bone marrow, rheumatoid arthritis, arthrosis, degraded immune function, diabetes, glucose intolerance, insulin resistance, function decreasing disorders, declines in testosterone, estrogen, growth hormone, IGF-I, reduced energy production, sarcopenia (loss of muscle), cardiovascular diseases (heart failure, myocardial infarction), loss of bone marrow, degraded immune function, idiopathic pulmonary fibrosis, age-related macular degeneration, hypertension, mitochondrial dysfunction, telomere dysfunction, Huntington's disease, skin aging, cataract, multiple sclerosis, Sjogren's syndrome, obesity, grey hair, and/or hearing loss.

"Macular degeneration" as used herein refers to deterioration of the central portion of the retina, the macula, which can result in blurred vision or loss of vision in the center of the visual field. Macular degeneration can be characterized as age-related macular degeneration (AMD), and can include dry macular degeneration or wet macular degeneration (also referred to as neovascular or exudative macular degeneration). In some embodiments, the treating, inhibiting, preventing, or ameliorating macular degeneration includes administering a formulation to the subject to prevent, treat, inhibit, or ameliorate macular degeneration. In some embodiments, the formulation may be administered intravenously. In some embodiments, intravenous administration is beneficial as a therapy for other diseases in addition to the treatment of macular degeneration. In some embodiments, the formulation may be administered into the eye by intravitreal, sub-orbital, retrobulbar, intraocular, subconjunctival, or other ocular injection. In some embodiments, the treating, inhibiting, preventing, or ameliorating includes administering a formulation for the treatment of a symptom of macular degeneration. For administration in or around the eye, the formulation is administered in an amount of 5, 10, 20, 30, 40, 50, 60, 70, 80, 90, or 100 µL or an amount within a range defined by any two of the aforementioned volumes. For administration in or around the eye, the formulation is concentrated, such that for each administration, an amount of PBD-PSCs is 1,000, 5,000, 10,000, 50,000, 100,000, 500,000, 1,000,000, 2,000,000, 3,000,000, 4,000,000, 5,000,000, 6,000,000, 7,000,000, 8,000,000, 9,000,000, 10,000,000, 50,000,000, or 100,000,000 cells/µL or an amount that is within a range defined by any two of the aforementioned amounts of cells per µL is administered or provided to a subject in need.

As used herein, the term "subject" is an animal, such as a vertebrate, including a mammal. The term "mammal" is defined as an individual belonging to the class Mammalia and includes, without limitation, humans, domestic and farm animals, and zoo, sports, or pet animals, such as sheep, dogs, horses, cats or cows. In some embodiments, the subject is mouse or rat. In some embodiments, the subject is human. A "subject" includes any animal that exhibits a symptom, or is at risk for exhibiting a symptom, of one or more disorder described herein. Suitable subjects (patients) include laboratory animals (such as mouse, rat, rabbit, or guinea pig), farm animals, and domestic animals or pets (such as a cat or dog). Non-human primates and/or, preferably, human patients, are included.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients, which is suitable for the selected mode of application such as oral application or injection, and administered in the form of a conventional pharmaceutical preparation, such as solid such as tablets, granules, powders, capsules, and/or liquid such as solution, emulsion, or suspension. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, or immunoglobulins; hydrophilic polymers such as polyvinylpyrrolidone, amino acids, or carbohydrates including glucose, mannose, or dextrins, chelating agents such as EDTA, sugar alcohols such as mannitol or sorbitol, salt-forming counter ions such as sodium, and nonionic surfactants such as Tween™, polyethylene glycol (PEG), and/or Pluronics™. Auxiliary, stabilizer, emulsifier, lubricant, binder, pH adjustor controller, or isotonic agent and other conventional additives may also be added to the carriers.

The pharmaceutically acceptable or appropriate carrier may include other compounds known to be beneficial to an impaired situation of the GI tract, (e.g., antioxidants, such as Vitamin C, Vitamin E, Selenium or Zinc); or a food composition. The food composition can be, but is not limited to, milk, yogurt, curd, cheese, fermented milks, milk based fermented products, ice-creams, fermented cereal based products, milk based powders, infant formulae, tablets, liquid bacterial suspensions, dried oral supplement, or wet oral supplement.

Stem Cells

"Stem cells", as used herein, refers to cells which under suitable conditions are capable of differentiating into other cell types having a particular, specialized function (e.g., "fully differentiated" cells) while under other suitable conditions are capable of self-renewing and remaining in an undifferentiated multipotent or pluripotent state as detailed below. A "cell" as used herein refers to a single cell as well as to a population of (e.g., more than one) cells. The population may be a pure population comprising one cell type. Alternatively, the population may comprise more than one cell type. The stem cells are preferably, PBD-PSCs obtained from, for example, peripheral blood, adipose tissue, bone marrow, female ovarian follicular fluid, and/or male seminal fluid.

"Peripheral blood derived pluripotent stem cells" (or "PBD-PSCs"), as used herein refers to a cell or a cell population characterized in that the cells are 2.5-4.5 μm in diameter, such as 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 μm in diameter, or an amount within a range defined by any two of the aforementioned values and are highly expressive of parathyroid hormone 1 receptor (PTH1R). PBD-PSCs are also referred to herein as PTH1R positive stem cells, PTH1R positive cells, or PTH1R positive PSCs. In some embodiments, the PBD-PSCs are referred to herein as parathyroid hormone (PTH) receptor-positive pluripotent stem cells. PBD-PSCs are positive for CD90 and CD133; positive/negative for CD29, CD34, CD105, and CD106; and negative for SSEA-3, CD200, and CD45. In some embodiments, the stem cells are expressive of SOX2 and OCT4. Although the name suggests that the stem cells are derived from peripheral blood, PBD-PSCs can be derived from other sources as well, where they may be found in abundance, including peripheral blood, adipose tissue, bone marrow, female ovarian follicular fluid, and/or male seminal fluid. In some embodiments, PBD-PSCs are present in a cell population. In some embodiments, the cell population includes additional stem cells and/or endothelial cells and/or other regenerative cells. In some embodiments, the PBD-PSCs are included in cell populations that have cells that are not regenerative cells, e.g., adipose cells, skin cells, bone cells, muscle cells, and/or cells from the female or male reproductive system, such as cells of the uterine wall or testis. In some embodiments, isolated PBD-PSCs are added back or mixed with a population of cells, which may include additional regenerative cells or may include non-regenerative cells e.g., adipose cells, skin cells, muscle cells, bone cells, or cells of the female or male reproductive system, such as uterine cells or cells of the testis.

The cells may be derived from a peripheral blood sample by centrifugation, filtration, lysing, and isolation techniques. Centrifugation can take place at 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 G, or at a centrifugal force that is within a range defined by any two of the aforementioned values. Centrifugation can include various cycles to isolate a desired component of peripheral blood. For example, a first centrifugation step may be used to isolate a plasma layer, performed at a low speed centrifugation, such as for example, 100, 200, 300, 400 or 500 G, or at a centrifugal force that is within a range defined by any two of the aforementioned values. The isolated plasma layer may then be subjected to higher speed centrifugation to isolate platelets, such as, for example, 800, 900, 1000, 1100, 1200 G or greater, or at a centrifugal force that is within a range defined by any two of the aforementioned values. The platelets precipitate, and the precipitate can be isolated and suspended. The resuspended platelets can be subjected to filtration to remove debris or unwanted material, for example, in a filter having pores of 0.1, 0.2, 0.3, 0.4, 0.5, 0.6, 0.7, 0.8, 0.9, 1.0, 2, 3, 4, or 5 μm pores, or a size within a range defined by any two of the aforementioned values. The platelet may then be subjected to lysis to obtain a platelet lysate, which may be further isolated or purified by centrifugation and/or filtration. Lysis can take place through various techniques, including, for example, reagent-based lysis, physical disruption (sonication). The PBD-PSCs may be isolated from the platelet lysate by contacting the platelet lysate by negative selection (for example, contacting the platelet lysate with an antibody, such as anti-CD45 antibody, to bind cells other than PBD-PSCs) or positive selection (for example, contacting the platelet lysate with an antibody, such as anti-PTH receptor antibody, to bind PBD-PSCs).

The most primitive germ cells in adult mammalian testis are the spermatogonial stem cells (SSCs); whereas primordial follicles (PFs) are considered the fundamental functional unit in ovary. However, this central dogma has recently been modified with the identification of PBD-PSCs in the adult mammalian gonads. These stem cells are more primitive to SSCs and are also implicated during postnatal ovarian neo-oogenesis and primordial follicle assembly. PBD-PSCs are pluripotent in nature and are characterized by nuclear Oct-4A, cell surface SSEA-4, and other pluripotent markers such as Nanog, Sox2, and/or TERT. PBD-PSCs are considered to be the descendants of epiblast stem cells and possibly the primordial germ cells that persist into adulthood and undergo asymmetric cell division to replenish the gonadal germ cells throughout life. The role of PBD-PSCs during infertility, endometrial repair, superovulation, and pathogenesis of various reproductive diseases like PCOS, endometriosis, cancer is addressed herein. Some embodiments provided herein relate to new avenues for research to better understand various reproductive processes and cancers. In some embodiments, the PBD-PSCs are relevant for regenerative medicine, translational research, and clinical applications in human reproduction.

Existing dogma that a female is born with fixed number of eggs was challenged by the detection of stem cells in adult mammalian ovary. Data has accumulated in support of ovarian stem cells (OSCs) proliferation, maintenance in culture, formation of germ cell nests and differentiation into oocytes and primordial follicle assembly using different strategies.

Flow cytometry analysis identified >8 μm OSCs, which are DDX1 positive and are considered equivalent to spermatogonial stem cells (SSCs) in testis. Analysis of both ovarian and testicular smears obtained after enzymatic digestion has led to the identification of PBD-PSCs. As indicated above, PBD-PSCs and OSCs/SSCs differ from each other in their size and OCT-4 expression. PBD-PSCs express pluripotent markers including nuclear OCT-4 whereas OSCs/SSCs express cytoplasmic OCT-4 indicating a differentiated state. PBD-PSCs can be studied by flow cytometry as small sized cells, which are LIN-/CD45-/Sca-1+. PBD-PSCs make up 0.02±0.008, 0.03±0.017 and 0.08±0.03% of total cells in normal, chemoablated and after FSH treatment to chemoablated mouse ovary respectively.

Spinning or centrifugation of cells obtained after enzymatic digestion of ovarian tissue at a speed of 1000 G (rather than 1200 rpm) throughout processing allows reliable detection of the PBD-PSCs by flow cytometry. Accordingly, in some procedures, PBD-PSCs are prepared by a method, wherein ovarian tissue is enzymatically digested or mechanically sheared so as to liberate the PBD-PSCs and said PBD-PSCs are isolated by centrifugation at 900, 950, 975, or 1000 G or at a centrifugal force that is within a range defined by any two of the aforementioned values.

"Parathyroid hormone type 1 receptor" (or "PTH1R") is a protein expressed on PBD-PSCs that acts as a receptor for parathyroid hormone (PTH) and for parathyroid hormone related protein (PTHrP). PTH and PTHrP act as chemoattractants to PBD-PSCs, and are therefore useful for the targeting of PBD-PSCs to a specific, desired region within an organism.

"Cell culture" or "cultured cell", as used herein, refer to cells or tissues that are maintained, cultured, cultivated or grown in an artificial, in vitro environment e.g., in a media in a vessel. Included within this term are continuous cell lines (e.g. with an immortal phenotype), primary cell cultures, finite cell lines (e.g., non-transformed cells), and any other cell population maintained in vitro. In this connection, a primary cell is a cell, which is directly obtained from a tissue or organ of an animal, including a human, in the absence of culture. Typically, though not necessarily, a primary cell is capable of undergoing ten or fewer passages in vitro before senescence and/or cessation of proliferation.

"Undifferentiated", as used herein, refers to cultured cells when a substantial proportion (at least 20%, and possibly over 50% or 80%) of the cells and their derivatives in the population display morphological characteristics of undifferentiated cells, distinguishing them from differentiated cells of embryo or adult origin. Cells are recognized as proliferating in an undifferentiated state when they go through at least 1 population doubling during a cultivation period of at least 3 weeks, while retaining at least about 50%, or the same proportion of cells bearing characteristic markers or morphological characteristics of undifferentiated cells after said cultivation period.

"Cell suspension" as used herein, refers to a culture of cells in which the majority of the cells freely float in the medium, typically a culture medium (system), and the cells floating as single cells, as cell clusters and/or as cell aggregates. In other words, the cells survive and propagate in the medium without being attached to a solid or semi solid substrate. "Adherent cells" as used herein refers to a cell or cell population that adheres to a substrate or surface.

"Culture system" as used herein, refers to culture conditions for supporting the maintenance and propagation of PBD-PSCs. The term denotes a combination of elements, which can include a basic medium (a cell culture medium usually comprising a defined base solution, which includes salts, sugars and amino acids) and a serum replacement supplement. The culture system may further comprise other elements such as, without being limited thereto, an extracellular matrix (ECM) component, additional serum or serum replacements, a culture (nutrient) medium and other exogenously added factors, which together provide suitable conditions that support PBD-PSC growth, cell culture maintenance, cell differentiation, or expression of various molecules. In the relevant context, the term "culture system" also encompasses the cells cultured therein.

As used herein, the PBD-PSC culture system includes stem cells cultured in the presence of a protein, such as an extracellular matrix protein, a cytokine, a growth factor, or an antigen. Specific examples include, an epidermal growth factor (EGF), a platelet derived growth factor (PDGF), a fibroblast growth factor (FGF and bFGF), a transforming growth factor (TGF-α and TGF-β 1, 2, & 3), a vascular endothelial growth factor (VEGF), a hepatocyte growth factor (HGF), a keratinocyte growth factor (KGF), a nerve growth factor (NGF), erythropoietin (EPO), an insulin-like growth factors (IGF-I and IGF-II), an interleukin cytokine (IL-1α,IL-1β, IL-2, IL-3, IL-4, IL-5, IL-6, IL-7, IL-8, IL-9, IL-10, IL-11, IL-12, IL-13), an interferon (IFN-α, IFN-β, and IFN-γ), a tumor necrosis factor (TNFα and TNF-β), a colony stimulating factor (GM-CSF and M-CSF), insulin, parathyroid hormone, fibronectin, vitronectin, tenascin, thrombospondin, gelatin, fibrillin, merosin, anchorin, chondronectin, link protein, bone sialoprotein, osteocalcin, osteopontin, epinectin, hyaluronectin, undulin, epiligrin, kalinin, collagenase, collagen, elastin, laminin, agrin, nidogen, and/or entactin or variations and/or combinations thereof. In some embodiments, the PBD-PSCs are cultured with retinoic acid and/or with one or more of a derivative of retinoic acid, or other small molecule.

"Gene products" as used herein refers to the product of a gene that is transfected into a cell or population of cells. The gene that is transfected can encode, for example, a protein, such as an extracellular matrix protein, a cytokine, a growth factor, or an antigen. Specific examples include, an epidermal growth factor (EGF), a platelet derived growth factor (PDGF), a fibroblast growth factor (FGF and bFGF), a transforming growth factor (TGF-α and TGF-β 1, 2, & 3), a vascular endothelial growth factor (VEGF), a hepatocyte growth factor (HGF), a keratinocyte growth factor (KGF), a nerve growth factor (NGF), erythropoietin (EPO), an insulin-like growth factors (IGF-I and IGF-II), an interleukin cytokine (IL-1α,IL-1β, IL-2, IL-3, IL-4, IL-5, IL-6, IL-7, IL-8, IL-9, IL-10, IL-11, IL-12, IL-13), an interferon (IFN-α, IFN-β, and IFN-γ), a tumor necrosis factor (TNFα and TNF-β), a colony stimulating factor (GM-CSF and M-CSF), insulin, parathyroid hormone, fibronectin, vitronectin, tenascin, thrombospondin, gelatin, fibrillin, merosin, anchorin, chondronectin, link protein, bone sialoprotein, osteocalcin, osteopontin, epinectin, hyaluronectin, undulin, epiligrin, kalinin, collagenase, collagen, elastin, laminin, agrin, nidogen, and/or entactin or variations and/or combinations thereof.

In some embodiments, the PBD-PSCs are transfected with human telomerase reverse transcriptase (hTERT) gene. The term "human telomerase catalytic subunit" or "hTERT" as used herein refers to a polypeptide sequence possessing telomerase catalytic activity. The hTERT gene is a nucleic acid that encodes hTERT. hTERT is a catalytic subunit of the enzyme telomerase and a critical element for telomerase activity. Expression of hTERT is not usually activated in normal cells, although other components of telomerase are expressed. In addition, hTERT has various telomere-independent functions, including enhancement of cellular proliferation, DNA damage response through change in chromatin structure, and inhibition of apoptosis by upregulation of BCL2 expression. These functions are independent of each other. hTERT synthesizes a TTAGGG tag on the end of telomeres to prevent cell death due to chromosomal shortening. In some embodiments, an isolated population of PTH receptor-positive pluripotent cells are transfected with an hTERT gene, thereby generating hTERT transfected PTH receptor-positive pluripotent stem cells. In some embodiments, the hTERT transfected PTH receptor-positive pluripotent stem cells are administered to a subject in a therapeutically effective amount. Telomere shortening is associated with ageing and telomerase malfunction is often associated with disease.

The term "vector" as used herein refers to a vehicle containing a polynucleotide sequence of interest, for example, the hTERT gene, wherein the polynucleotide sequence of interest encodes a polypeptide. The polynucleotide sequence of interest may be operably linked to a promoter, allowing the sequence to be expressed in a host cell into which the vector is introduced. Examples of vectors include plasmids, cosmids, bacmids, and viral vectors. Categories of viral vectors include bacteriophage (e.g., lambda phage, or M13 phage), retrovirus (including lentivirus), adenovirus, adeno-associated virus, herpesvirus (e.g., herpes simplex virus), poxvirus, baculovirus, papillomavirus, and/or papovavirus (e.g., SV40). In a preferred embodiment, the vector is a lentivirus such as human immunodeficiency virus (HIV). A vector may contain a variety of elements for controlling expression of the polynucleotide sequence of interest, including promoter sequences, transcription initiation sequences, enhancer sequences, selectable elements, and/or reporter genes. In addition, the vector may contain an origin of replication. A vector may also include materials to aid in its entry into the cell, including but not limited to a viral particle, a liposome, or a protein coating.

The terms "introduced," "introduced," "introducing," and "introduction" as used herein refer to the entry of a vector or vectors into a host cell. A vector may be introduced into the host cell by non-viral transfection methods or by viral transduction. Non-viral transfection methods include but are not limited to DEAE-Dextran-mediated, calcium-phosphate mediated, cationic lipid-mediated transfection, electroporation, nucleofection, lipofection, microinjection, ballistic introduction, and/or scrape loading.

As used herein, "transfect," "transfection," or "transfecting" refer to the delivery or transfer and uptake of nucleic acids into cells. Transfection can be viral or non-viral transfection. In some embodiments, the hTERT gene is non-virally transfected into the isolated population of PTH receptor positive pluripotent cells. Non-viral transfection can include, for example, chemical-based transfection, non-chemical-based transfection, and/or particle-based transfection. For example, electroporation, sonoporation, optical transfection, protoplast fusion, impalefection, hydrodynamic delivery, gene gun therapy, magnetofection, particle bombardment, viral transduction, and/or nucleofection.

Chemical-based transfection can be divided into several kinds: for example, using calcium phosphate precipitation, cyclodextrin, polymers, liposomes, or nanoparticles.

One of the simplest methods uses calcium phosphate. HEPES-buffered saline solution (HeBS) containing phosphate ions is combined with a calcium chloride solution containing the DNA to be transfected. When the two are combined, a fine precipitate of the positively charged calcium and the negatively charged phosphate forms, binding the nucleic acid species to be transfected on its surface. The suspension of the precipitate is then added to the cells to be transfected. The cells take up some of the precipitate, and with it, the nucleic acid species.

Other methods use highly branched organic compounds, such as dendrimers, to bind the DNA and get it into the cell. Another method is the inclusion of the nucleic acid species to be transfected in liposomes, which can fuse with the cell membrane, releasing the nucleic acid species into the cell. Transfection may sometimes be increased using cationic liposomes (or mixtures). Another method involves the use of cationic polymers such as DEAE-dextran or polyethylenimine. The negatively charged peptide species binds to the polycation and the complex is taken up by the cell via endocytosis.

With regard to non-chemical methods, electroporation (gene electrotransfer) is a popular method, where transient increase in the permeability of cell membrane is achieved when the cells are exposed to short pulses of an intense electric field. Cell squeezing is a more modern method which enables delivery of molecules into cells by a gentle squeezing of the cell membrane. It is a high throughput vector-free microfluidic platform for intracellular delivery. Sonoporation uses high-intensity ultrasound to induce pore formation in cell membranes. This pore formation is attributed mainly to the cavitation of gas bubbles interacting with nearby cell membranes. Optical transfection is a method whereby a small (~1 μm diameter) hole is transiently generated in the plasma membrane of a cell using a highly focused laser.

Protoplast fusion is a technique in which transformed bacterial cells are treated with lysozyme in order to remove the cell wall. Following this, fusogenic agents (e.g. Sendai virus, PEG, or electroporation) are used in order to fuse the protoplast carrying the gene of interest with the target recipient cell. A major disadvantage of this method is that bacterial components are non-specifically introduced into the target cell, as well.

Impalefection is a method of introducing nucleic acid species bound to a surface of a nanofiber that is inserted into a cell. This approach can also be implemented with arrays of nanofibers that are introduced into large numbers of cells and intact tissue.

In relation to particle-based methods, one direct approach to transfection is the gene gun, where the nucleic acid species is coupled to a nanoparticle of an inert solid (commonly gold) which is then "shot" directly into the target cell's nucleus.

Magnetofection, or magnet assisted transfection, which uses magnetic force to deliver DNA into target cells. Nucleic acids are first associated with magnetic nanoparticles. Then, application of magnetic force drives the nucleic acid particle complexes towards and into the target cells, where the cargo is released.

Another particle-based method of transfection is particle bombardment. The nucleic acid species is delivered through membrane penetration at a high velocity, usually connected to microprojectiles.

Based on the physical method of electroporation, nucleofection uses a combination of electrical parameters with cell-type specific reagents. The substrate is transferred directly into the cell nucleus and the cytoplasm. "Cell marker", as used herein, refers to is any phenotypic feature of a cell that can be used to characterize it or discriminate it from other cell types. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the cell type of interest. The markers can also be identified by a biochemical or enzyme assay that depends on the function of the gene product. Associated with each marker is the gene that encodes the transcript, and the events that lead to marker expression. A marker is said to be preferentially expressed in an undifferentiated or differentiated cell population, if it is expressed at a level that is at least 5 times higher (in terms of total gene product measured in an antibody or PCR assay) or 5 times more frequently (in terms of positive cells in the population). Markers that are expressed 10, 100, or 10,000 times higher or more frequently are increasingly more preferred.

Figure 6:
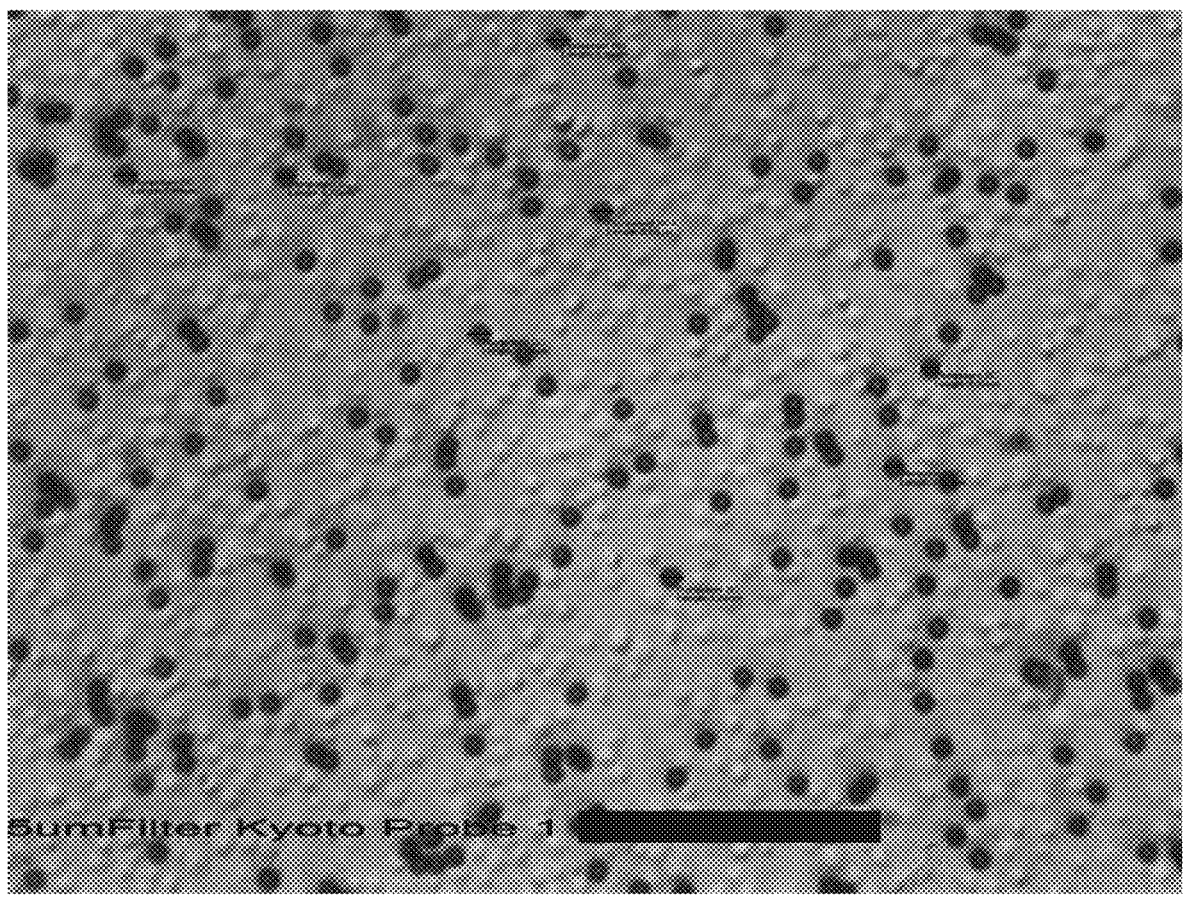
FIG. 6 depicts a micrograph of the PBD-PSCs described herein. The stem cells are 2.5-4.5 μm in diameter and carry the pluripotent stem cell marker Kyoto probe 1.
Figure 7:
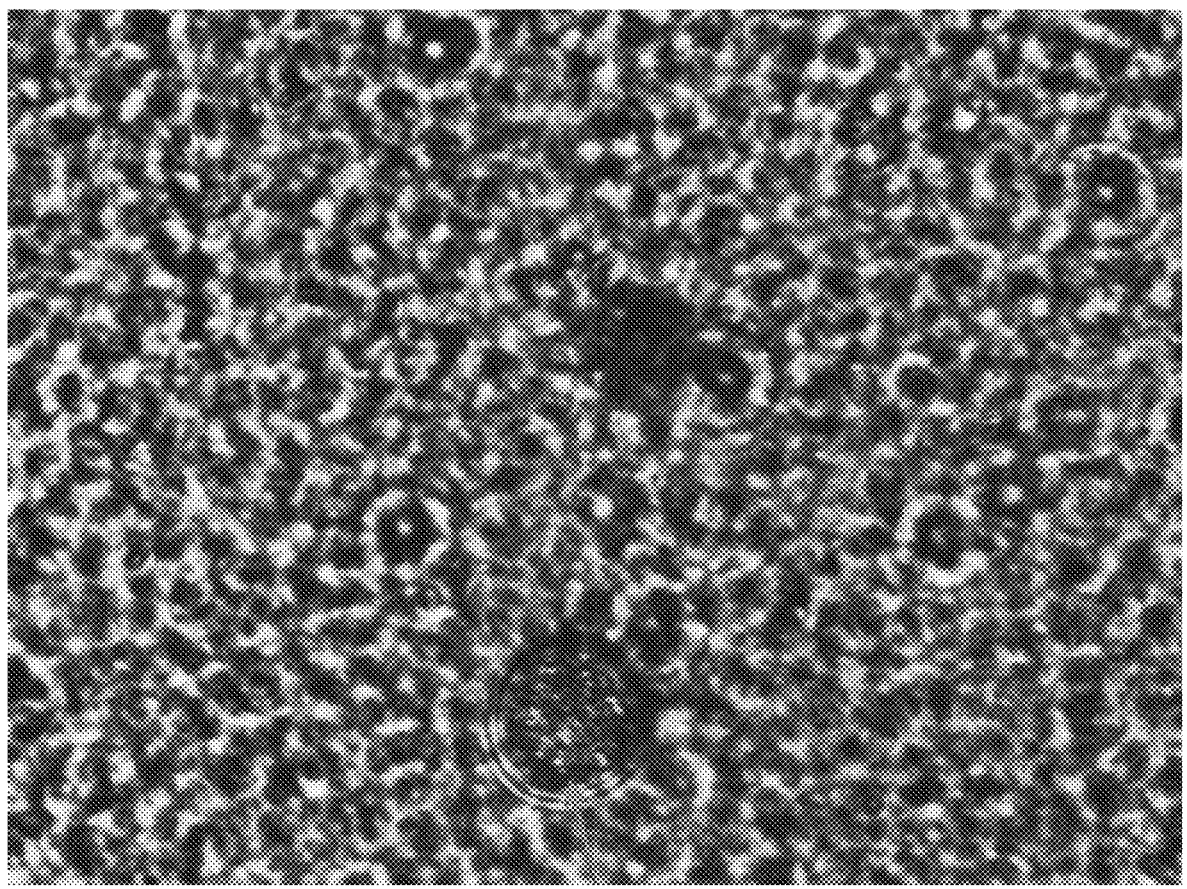
FIG. 7 is a micrograph showing that the PBD-PSCs form embryoid-like bodies when cultured, providing evidence that these cells are very primitive and potent stem cells.
Figure 8:
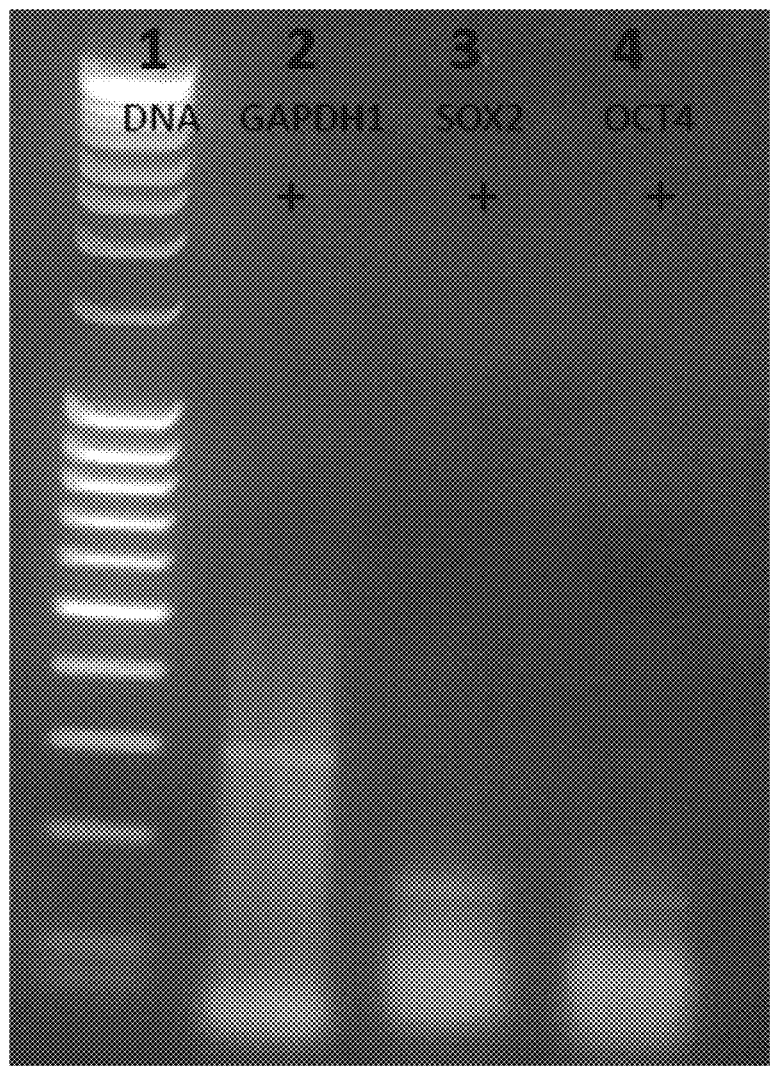
FIG. 8 shows the gene expression of PBD-PSCs, using conventional Rt-PCR for stem cell marker detection. Lane 1 is the DNA ladder, lane 2 is a control GAPDH1, lane 3 shows detection of Sox2, and lane 4 shows detection of Oct4.

In some embodiments a stem cell population is provided, wherein the stem cell population comprises PBD-PSCs. As shown in FIG. 6, the PBD-PSCs are 2.5-4.5 μm in diameter, such as 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 μm in diameter, or an amount within a range defined by any two of the aforementioned values. In addition, the cells are characterized in that they are expressive of PTH1R. The PBD-PSCs form embryoid-like bodies when cultured, as shown in FIG. 7, and are capable of differentiation into ectoderm, mesoderm, and endoderm when cultured. In some embodiments, the cells are expressive of classical CD markers. PBD-PSCs are positive for CD90 and CD133; positive/negative for CD29, CD34, CD105, and CD106; and negative for SSEA-3, CD200, and CD45. In addition, as shown in FIG. 8, the PBD-PSCs are expressive of Sox2 and Oct4. Furthermore, the PBD-PSCs are positive for SSEA-4 and CXCR-4. The PBD-PSCs are +/− for Lin Cocktail, Sca-1, and Lgr5.

Figure 9:
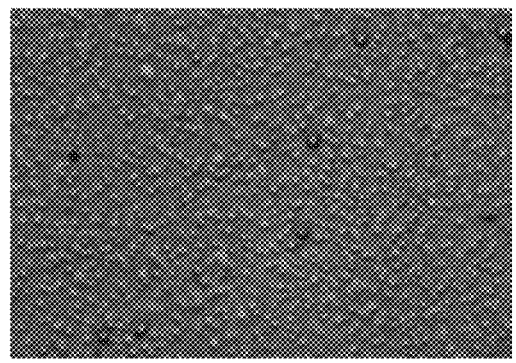
FIG. 9 shows micrographs of the PBD-PSCs from different animal sources; equine, canine, and camel.
Figure 9:
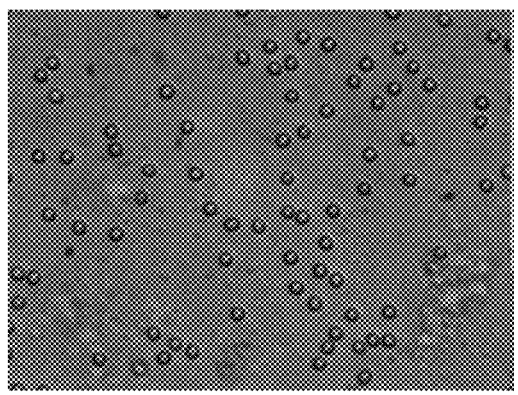
Figure 9:
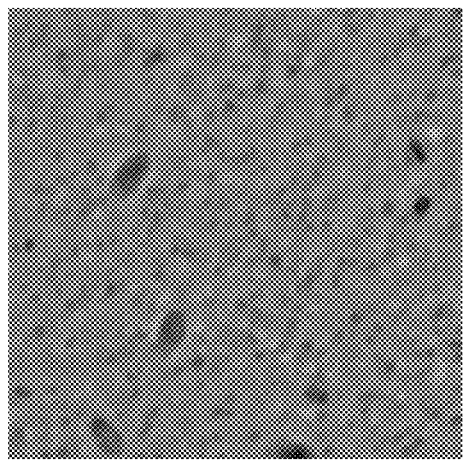

PBD-PSCs are found in a variety of animal populations in addition to human, including for example, equine, canine, and camel, as shown in FIG. 9. Furthermore, PBD-PSCs can optionally be cultured with one or more peptide, such as an ECM protein, a cytokine, a growth factor, or an antigen.

In some embodiments, an antibody against PBD-PSCs is provided. In some embodiments, the antibody is a monoclonal or polyclonal antibody. In some embodiments, the antibody is a humanized antibody. An "isolated antibody" is an antibody that is not associated with naturally-associated components, including other naturally-associated antibodies, that accompany it in its native state and is free of other proteins from the same species. Furthermore, the isolated antibody is expressed by a cell from a different species or does not occur in nature. The term human antibody includes all antibodies that have one or more variable and constant regions derived from human immunoglobulin sequences. A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species.

Methods of Isolating PBD-PSCs

Some embodiments are related to methods of isolating PBD-PSCs from a sample of a subject. The subject can be a human, or other mammal, such as a domestic animal, companion animal, or farm animal. In some embodiments, the subject is a horse, dog, cat, or camel. In some embodiments, the sample is peripheral blood, adipose tissue, bone marrow, ovarian follicular fluid, or seminal fluid. In some embodiments, the sample is contacted with an antibody to the PBD-PSC. In some embodiments, the antibody is an anti-PTH1R antibody. In some embodiments, the antibody is associated with a magnetic bead to assist in the isolation and separation of the antibody from the sample. In such cases, a magnetic field is applied to the sample, and the magnetic bead, associated with the antibody-PBD-PSC complex is separated from the sample mixture. In some embodiments, the sample is washed with a separation buffer, and the PBD-PSCs are isolated. In some embodiments, avidin or streptavidin and biotin are used to attach the magnetic bead to the antibody.

In some embodiments, the PBD-PSCs are isolated extracorporeally. By one such approach, the whole blood or plasma from a subject is obtained and introduced into an extracorporeal system comprising a membrane, support, or bead, preferably a porous membrane, configured to capture the PBD-PSCs e.g., a membrane, bead, or support having the anti-PTH1R antibody or a binding portion thereof affixed or immobilized to said membrane, support or bead. The anti-PTH1R antibody or a binding portion thereof affixed or immobilized to said membrane, support or bead can be incorporated into a cartridge, which is configured for introduction or assembly into a dialysis or blood recirculation device. In some embodiments, a centrifugal or gravity force or pressure is applied to the membrane, thereby causing the whole blood to pass through the membrane, support or bead but retaining the PBD-PSCs, which are captured by the membrane, support or bead. In some embodiments, the pass-through blood is reinfused into the subject. In some embodiments, the isolated PBD-PSCs are prepared for subsequent reinfusion or administration to the individual.

In some embodiments, the quantity of PBD-PSCs isolated from a sample of a subject is 1,000, 5,000, 10,000, 50,000, 100,000, 500,000, 1,000,000, 2,000,000, 3,000,000, 4,000,000, 5,000,000, 6,000,000, 7,000,000, 8,000,000, 9,000,000, 10,000,000, 50,000,000, or 100,000,000 cells/mL of sample (peripheral blood, tissue homogenate, etc.), or an amount that is within a range defined by any two of the aforementioned quantities.

Methods of Using PBD-PSCs

Aspects of the present invention concern the first medical use of PBD-PSCs. Accordingly, some embodiments relate to PBD-PSCs for use as a medicament. Some embodiments provided herein relate to the use of PBD-PSCs for the treatment or amelioration of infertility, skin disorders, hair loss, malignant carcinomas, bone disorders, neurological disorders, and/or autoimmune disorders. In these methods, the PBD-PSCs and/or a cell population comprising the PBD-PSCs are administered or provided to a selected or identified subject e.g., a subject selected or identified for receiving a therapeutic that treats or ameliorates infertility, a skin disorder, hair loss, a malignant carcinoma, a bone disorder, neurological disorders, and/or autoimmune disorders. The selection and/or identification of such a subject in need can be accomplished by clinical evaluation and/or diagnostic test.

In some embodiments, isolated PBD-PSCs are administered to a subject who suffers from infertility e.g., a subject selected and/or identified as being one in need of an infertility treatment or a therapeutic that ameliorates infertility. In some embodiments, the selected or identified subject has previously undertaken in vitro fertilization and/or intracytoplasmic sperm injection (IVF/ICSI), but has been unsuccessful. In some embodiments, the selected or identified subject does not suffer from polycystic ovary syndrome (PCOS). In some embodiments, the isolated PBD-PSCs or a cell population comprising PBD-PSCs are administered to said subject by intra-arterial injection into the uterine artery. In some embodiments, the PBD-PSCs are administered intravenously. In some embodiments, the PBD-PSC therapy increases endometrial thickness, endometrial receptivity, oocyte count, oocyte quality, ovarian function, or estradiol quantity or combinations thereof.

In some embodiments, isolated PBD-PSCs or a cell population comprising PBD-PSCs are administered to a subject who has been selected or identified as one that suffers from a skin disorder e.g., a subject selected and/or identified as being one in need of an skin disorder treatment or a therapeutic that ameliorates a skin disorder. In some embodiments, the subject is identified or selected as being one that suffers from a skin disorder such as skin aging that has resulted in wrinkles, loss of elasticity, or loss of dermal radiance. In some embodiments, the subject has been identified or selected as being one that suffers from loss of dermal collagen and/or loss of dermal elastin or that has or desires to remove fine lines and/or wrinkles. In some embodiments, the PBD-PSCs are administered topically via a cream or lotion. In some embodiments, the PBD-PSCs are administered subcutaneously or transdermally. In some embodiments, the PBD-PSC therapy increases the dermal collagen and elastin, and reduces fine lines, reduces wrinkles, increases radiance, or increases dermal tightness or combinations thereof.

In some embodiments, isolated PBD-PSCs or a cell population comprising PBD-PSCs are administered to a subject who has been selected or identified as one that suffers from a bone disorder e.g., a subject selected and/or identified as being one in need of a bone disorder treatment or a therapeutic that ameliorates a bone disorder. In some embodiments, the bone disorder is a bone injury, a bone fracture, a spinous fracture, osteopenia, or osteoporosis or combinations thereof. In some embodiments, the composition is administered parenterally, subcutaneously, intravenously, or intra-arterially to the identified or selected subject. In some embodiments, the administration of PBD-PSCs results in increased bone density, repaired bone damage, or combinations thereof.

In some embodiments, isolated PBD-PSCs or a cell population comprising PBD-PSCs are administered to a subject who has been selected or identified as one that suffers from a neurological disorder e.g., a subject selected and/or identified as being one in need of a treatment for a neurological disorder or a therapeutic that ameliorates a neurological disorder. In some embodiments, the neurological disorder is cerebellar ataxia. In some embodiments, the PBD-PSC is administered subcutaneously, intravenously, or intra-arterially to the subject. In some embodiments, the administration of PBD-PSCs results in an improvement of the neurological disorder.

In some embodiments, isolated PBD-PSCs or a cell population comprising PBD-PSCs are administered to a subject who has been selected or identified as one that suffers from a metastatic carcinoma or other malignancy e.g., a subject selected and/or identified as being one in need of a treatment for a malignancy or metastatic carcinoma or a therapeutic that ameliorates a malignancy or metastatic carcinoma. In some embodiments, the metastatic carcinoma is pulmonary metastases. In some embodiments, the PBD-PSC is administered subcutaneously, intravenously, or intra-arterially to the subject. In some embodiments, the administration of PBD-PSCs results in an improvement of the malignancy or metastatic carcinoma.

In some embodiments, isolated PBD-PSCs or a cell population comprising PBD-PSCs are administered to a subject who has been selected or identified as one that suffers from an autoimmune disorder, or who exhibits symptoms of an autoimmune disorder. In some embodiments, the autoimmune disorder is one or more disorder as identified or described herein. In some embodiments, the PBD-PSC is administered subcutaneously, intravenously, or intra-arterially to the subject. In some embodiments, the administration of PBD-PSCs results in an improvement of the neurological disorder.

In some embodiments, PBD-PSCs are isolated from a donor and transplanted to a recipient who is in need of treatment with PBD-PSCs. In some embodiments, the donor is a young subject. In some embodiments, the recipient is an older subject in need. In some embodiments, the recipient may be suffering from a disorder as described herein. In some embodiments, the recipient may be suffering from aging effects. In some embodiments, the donor cells may or may not match with the tissue or blood of the recipient cells, but the recipient is capable of treatment without consequence of an unmatched donor. FIGS. 13-19 generally depict the use of donor cells for providing anti-aging effects for a recipient.

In some embodiments, isolated PTH receptor-positive pluripotent stem cells are transfected with an effective amount of a gene. In some embodiments, the gene is an hTERT gene that encodes hTERT. In some embodiments, hTERT is transfected into the cells non-virally, as disclosed herein. In some embodiments, hTERT transfected cells are administered in a therapeutically effective amount to a subject. In some embodiments, the subject suffers from an age-related disorder, as described herein, such as, for example, abnormal proliferative diseases, cancer, degenerative diseases, neuron degenerating disease (Alzheimer's disease, Parkinson's disease, stroke), loss of memory, loss of neuromuscular coordination, decreased longevity, reduced heart function, reduced circulatory function, reduced lung function, atherosclerosis, hypertension, osteoarthritis, osteoporosis, sarcopenia, loss of bone marrow, rheumatoid arthritis, arthrosis, degraded immune function, diabetes, glucose intolerance, insulin resistance, function decreasing disorders, declines in testosterone, estrogen, growth hormone, IGF-I, reduced energy production, sarcopenia (loss of muscle), cardiovascular diseases (heart failure, myocardial infarction), loss of bone marrow, degraded immune function, idiopathic pulmonary fibrosis, age-related macular degeneration, hypertension, mitochondrial dysfunction, telomere dysfunction, Huntington's disease, skin aging, cataract, multiple sclerosis, Sjogren's syndrome, obesity, grey hair, or hearing loss.

In some embodiments, the therapeutically effective amount is an amount sufficient to treat, reverse, inhibit, or improve one or more of the aforementioned age-related disorders. In some embodiments, the therapeutically effective amount is an amount sufficient to reduce telomere shortening, increase cellular self-renewal, increase life-span, reduce fine lines or wrinkles, reducing aging in a cell or in a subject, or recover telomerase activity in a cell. In some embodiments, the hTERT transfected PTH receptor-positive stem cells are administered in an amount of 10,000 cells/mL to 10,000,000 cells/mL, such as 10,000, 50,000, 100,000, 500,000, 1,000,000, 5,000,000, or 10,000,000 cells/mL, or an amount within a range defined by any two of the aforementioned values. In some embodiments, the hTERT transfected PTH receptor-positive stem cells are administered once weekly, once monthly, or once annually to a subject in a dose amount as described herein. In some embodiments, the hTERT transfected PTH receptor-positive stem cells are administered topically via a cream or lotion. In some embodiments, the hTERT transfected PTH receptor-positive stem cells are administered parenterally.

In some embodiments, a composition comprising the isolated stem cells described herein, including the hTERT transfected stem cells is provided. The composition may be formulated for topical or parenteral administration, and may include appropriate pharmaceutically acceptable carriers for the mode of administration, as described herein. In some embodiments, the compositions or methods provided herein are related to increasing lifespan, inhibiting or delaying the aging process, and/or treating, preventing, or delaying, an age-related disease or disorder.

Accordingly, in some embodiments, the PBD-PSC composition, including the hTERT transfected stem cell composition, made in accordance with the teachings set forth herein, comprises purified PBD-PSCs, or hTERT transfected stem cells. In some embodiments, the preparation further comprises a pharmaceutically acceptable carrier, a protein, such as an extracellular matrix protein, a cytokine, a growth factor, or an antigen. In some embodiments, the aforementioned preparations are useful for the treatment, prevention, or amelioration or inhibition of a skin disorder such as any one or more of the following disorders: rhytide, non-enzymatic glycosylation of the skin, sun damage, smoking damage, fibrosis of the skin, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne, psoriasis, including plaque psoriasis, guttate psoriasis, inverse psoriasis, pustular psoriasis, erythrodermic psoriasis, nail psoriasis, and/or psoriatic arthritis, and/or combinations and/or variations thereof.

Figure 13:
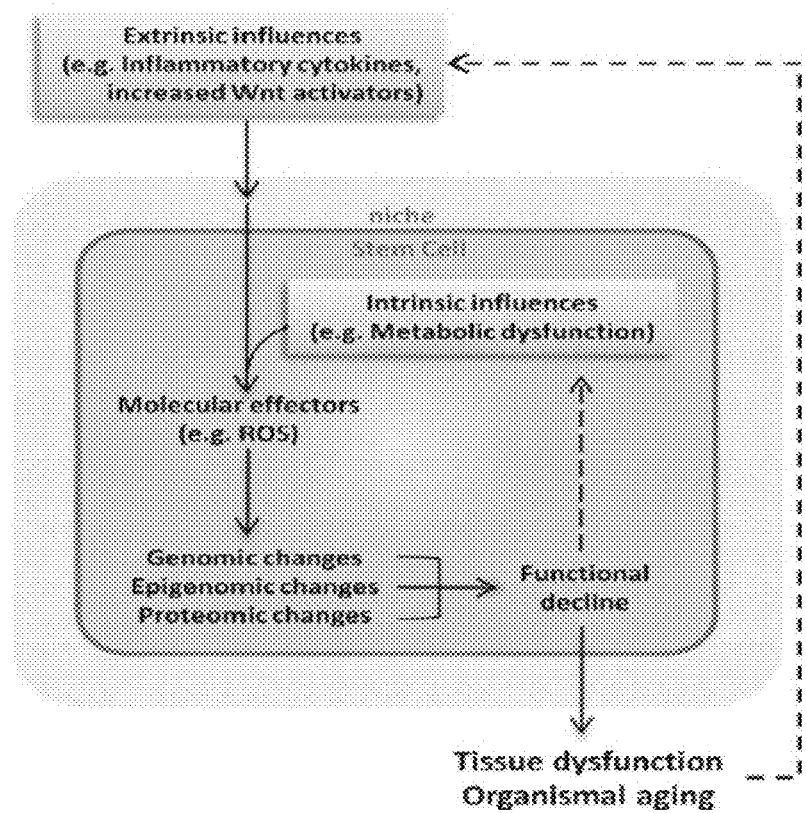
FIG. 13 illustrates the processes involved in organismal aging. Extrinsic influences act together with intrinsic influences causing genomic, epigenomic, and proteomic changes that result in functional decline. This in turn leads to tissue dysfunction and organismal aging.

FIG. 13 is a schematic diagram that depicts the general functional decline in stem cells as a result of aging. Numerous influences work in concert to result in functional decline, including, for example, extrinsic and intrinsic influences. Extrinsic influences can include, for example, inflammatory cytokines or increased Wnt activators. Intrinsic influences include metabolic dysfunction. These influences work with molecular effectors, such as reactive oxygen species to result in genomic, epigenomic, and/or proteomic changes, resulting in a functional decline of stem cells, which further exacerbates the negative intrinsic influences. Furthermore, the functional decline results in tissue dysfunction and organismal aging, which further exacerbates the extrinsic influences, resulting in aging effects.

Figure 14:
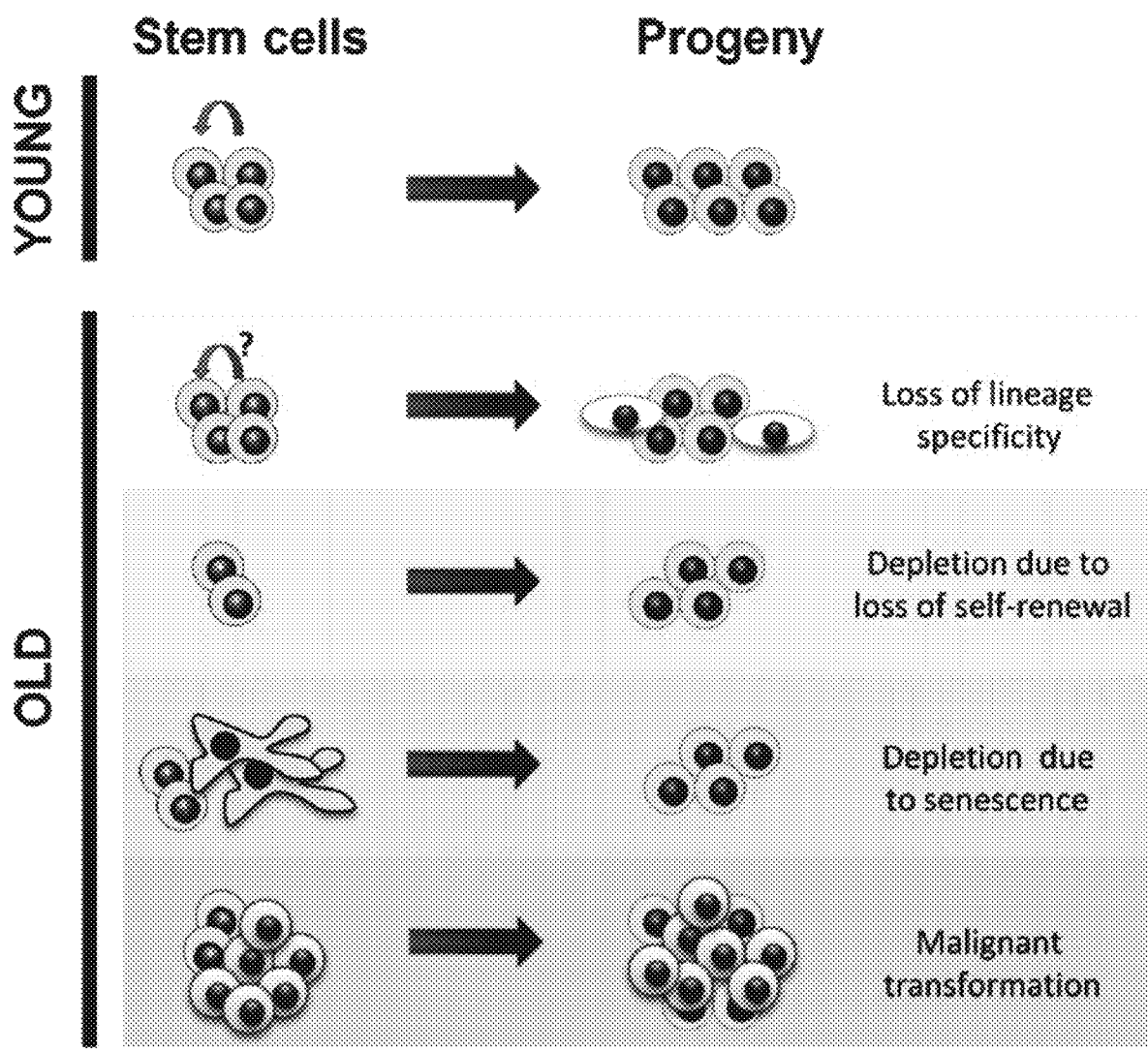
FIG. 14 shows the typical progression of stem cells. Young stem cells are capable of producing healthy progeny. However, as stem cells age, the resulting progeny declines in function due to loss of lineage specificity, depletion due to loss of self-renewal, depletion due to senescence, and malignant transformation.
Figure 15:
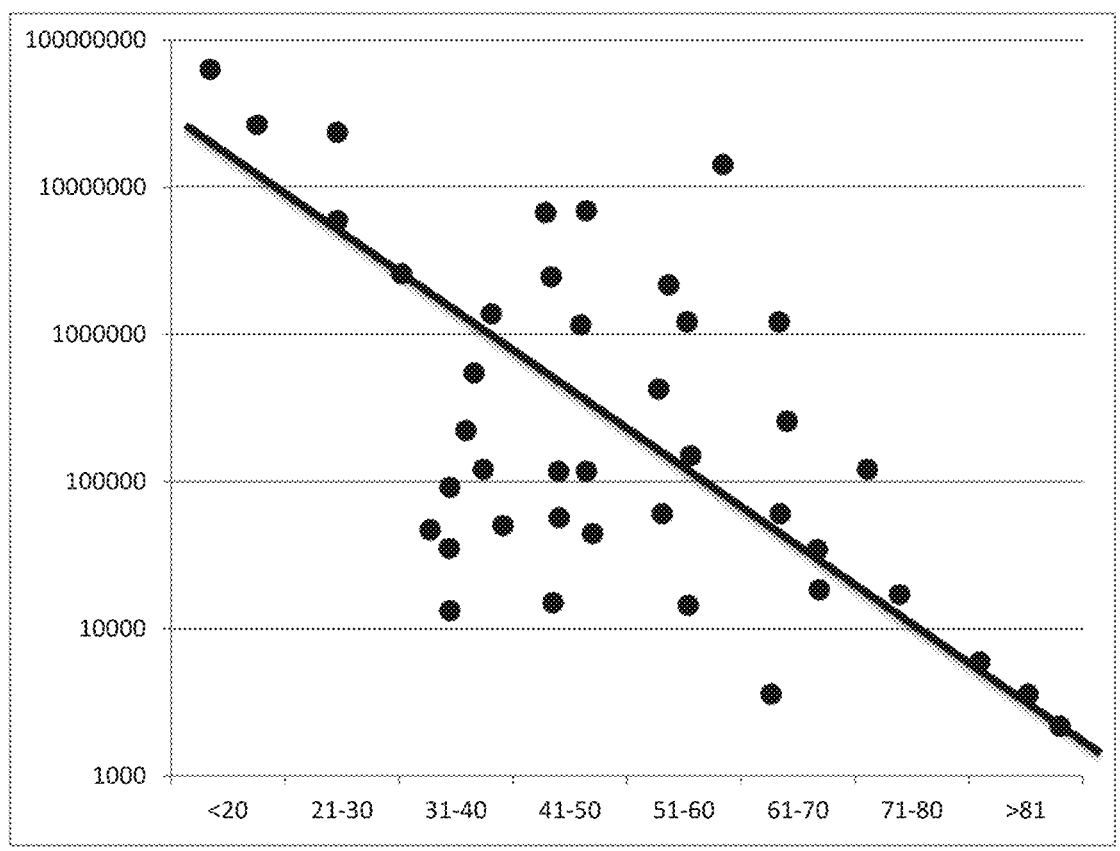
FIG. 15 illustrates the negative correlation between the PTHR-positive stem cells per mL of plasma (y-axis) by age of subject (x-axis).
Figure 16:
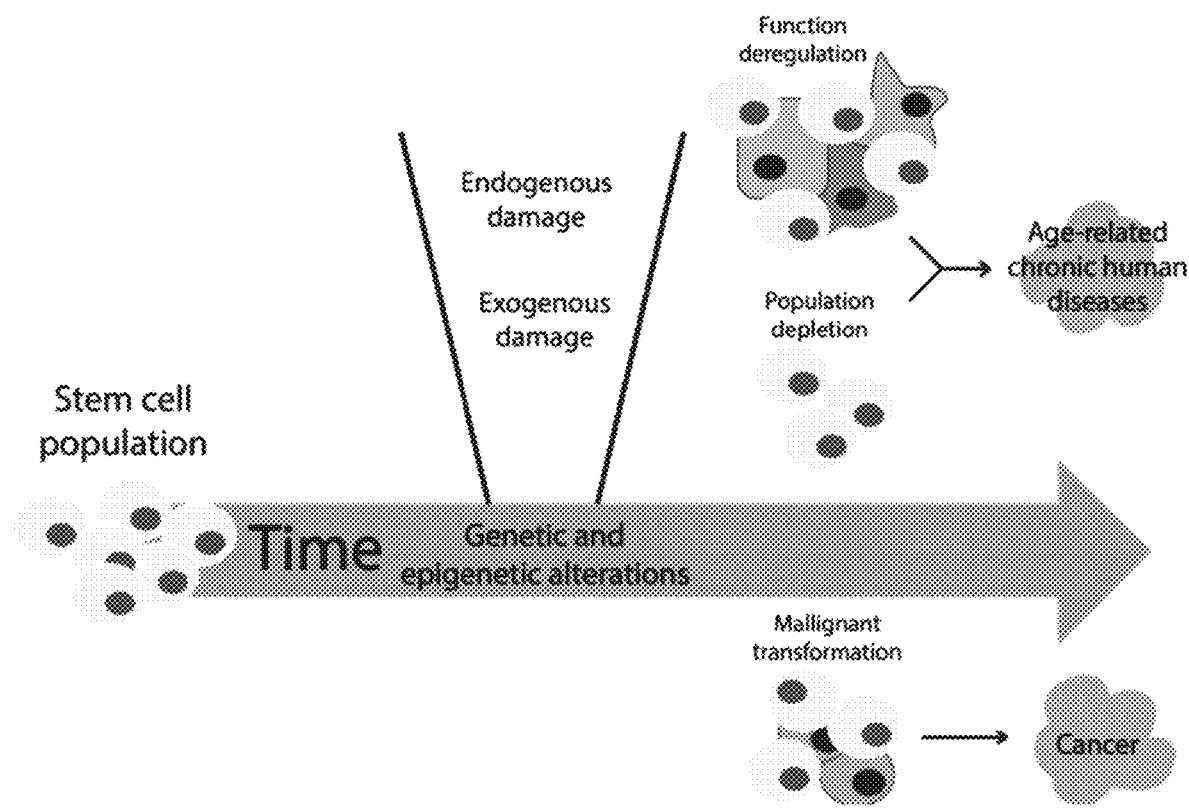
FIG. 16 illustrates the genetic and epigenetic alterations that occur over time to any given stem cell population within an organism.
Figure 17:
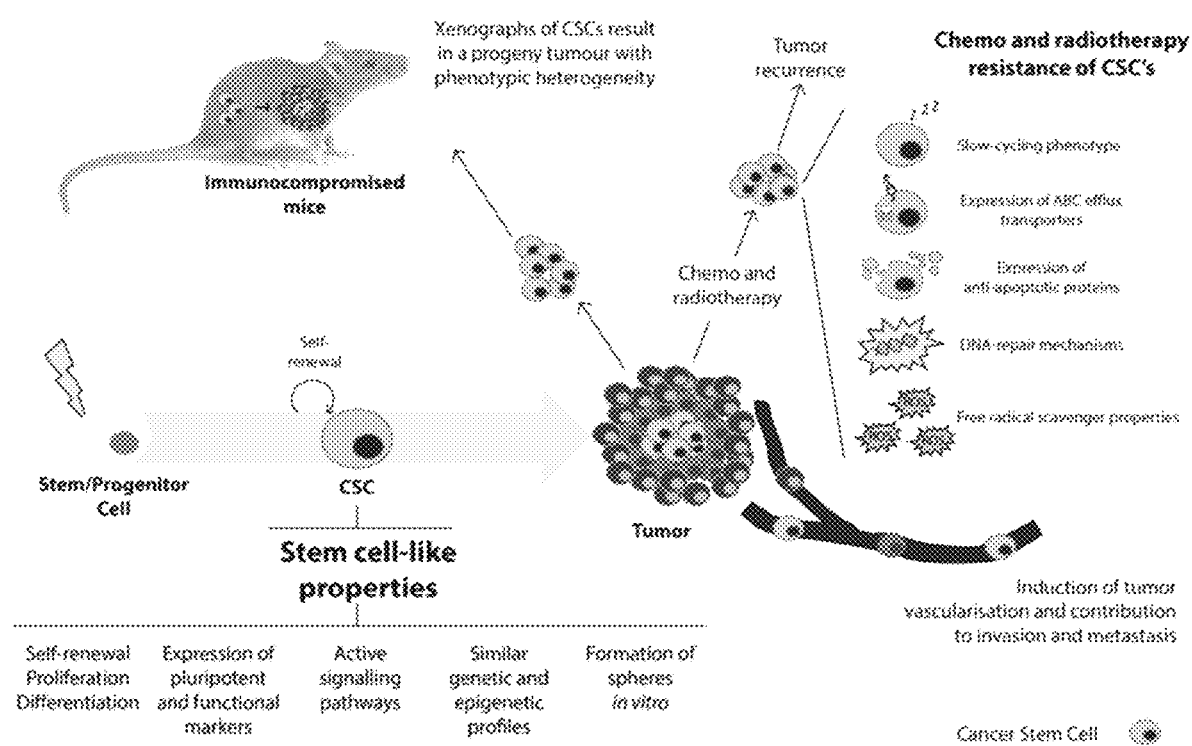
FIG. 17 illustrates the properties of cancer stem cells (CSCs), including the chemo and radiotherapy resistance of CSCs.
Figure 18:
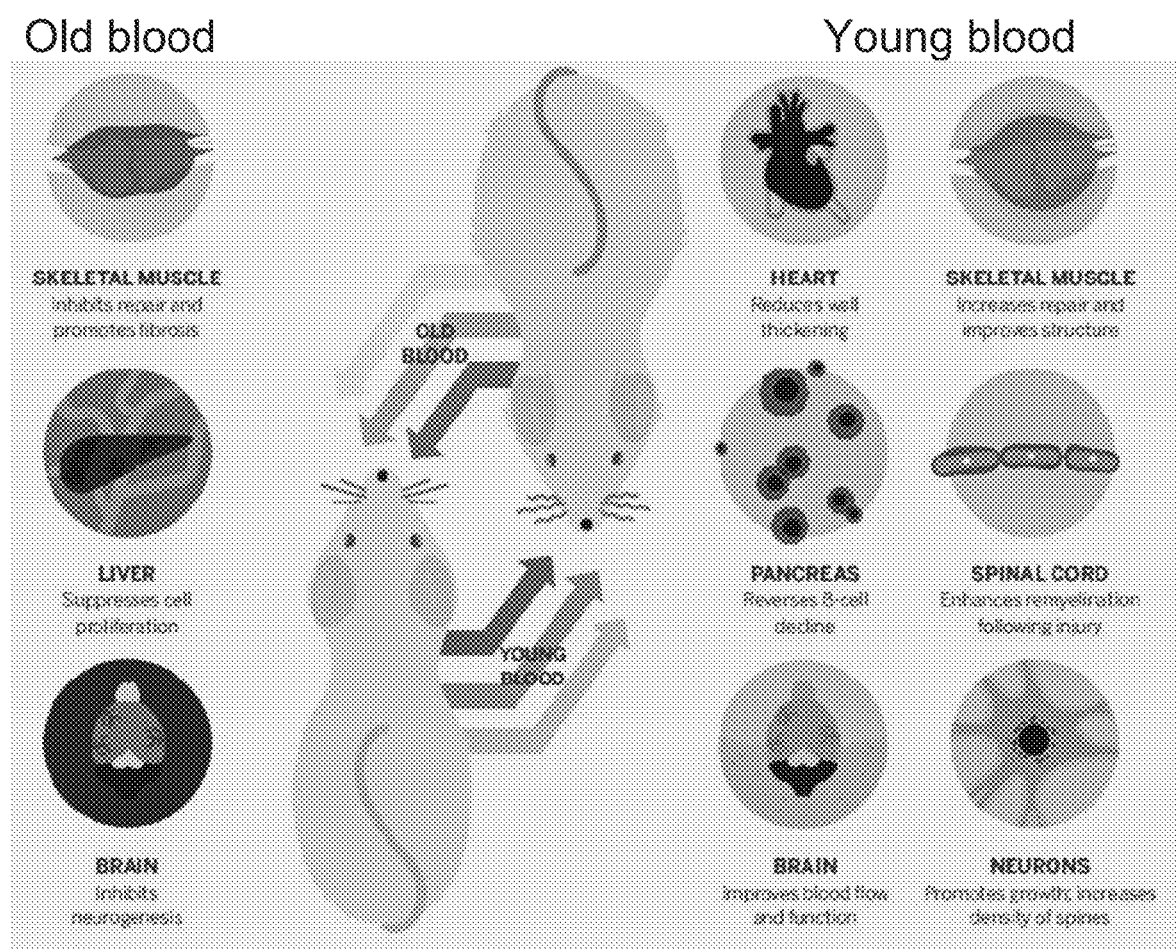
FIG. 18 illustrates the factors in young blood versus old blood for the ability to activate stem cells and rejuvenate organs in cells in old mice. Factors in old blood appear to inhibit regenerative capacity in young mice.
Figure 19:
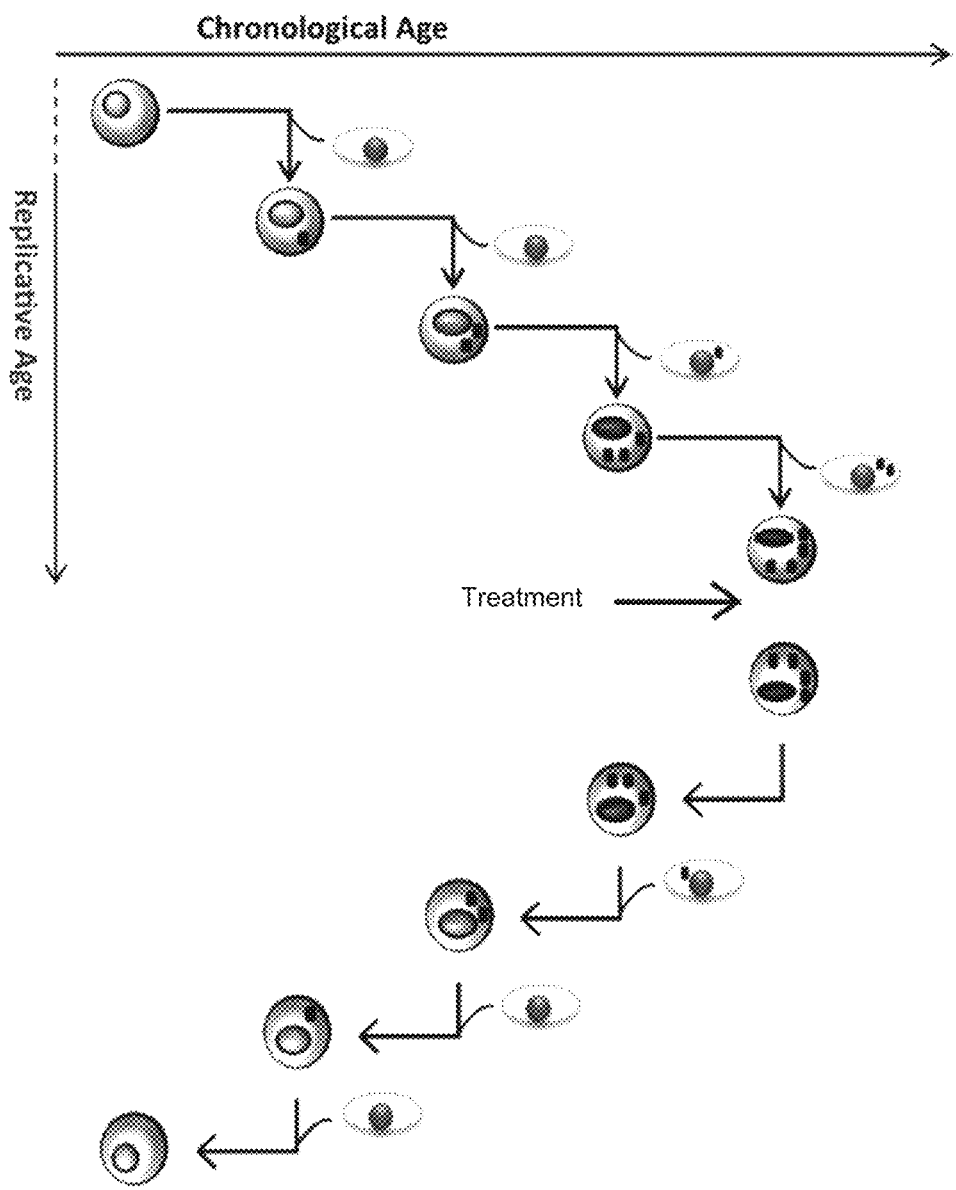
FIG. 19 shows that over time and over the course of replication, stem cells show increased effects of aging. However, the aging effects experienced by stem cells over chronological and replicative life span can be reversed by the treatments described herein.

FIG. 14 shows the progeny of stem cells from a perspective of young stem cells that experience fewer negative influences as well as old stem cells, which experience greater numbers of intrinsic and extrinsic influences, resulting in aging effects. FIG. 15 shows the strong trend towards negative correlation of the quantity of PBD-PSCs with patients' age.

The invention is generally disclosed herein using affirmative language to describe the numerous embodiments. The invention also includes embodiments in which subject matter is excluded, in full or in part, such as substances or materials, method steps and conditions, protocols, or procedures. Thus, even though the invention is generally not expressed herein in terms of what the invention does not include aspects that are not expressly excluded in the invention are nevertheless disclosed herein.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

Example 1

Preparation of Antibodies Against PBD-PSCs

The following example demonstrates a method for the development of monoclonal antibodies (mAb) against PBD-PSC.

Figure 10:
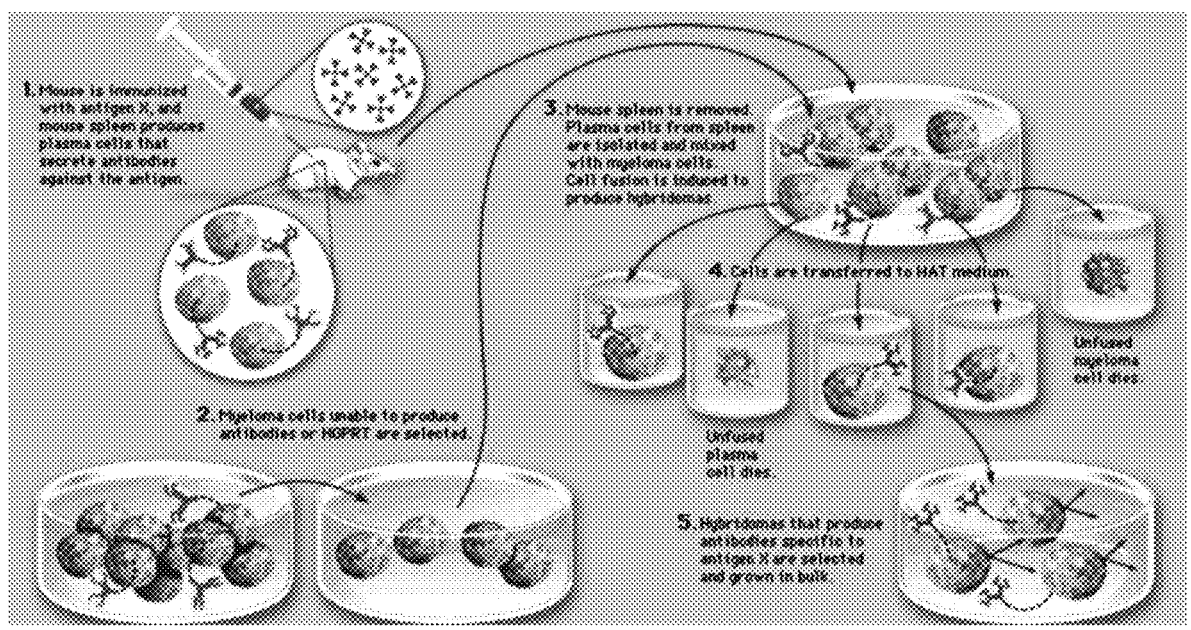
FIG. 10 illustrates the method of developing unique monoclonal antibodies that target a unique marker to the PBD-PSCs. The monoclonal antibody can be used to select the specific pluripotent stem cells for diagnostic and treatment purposes.

FIG. 10 provides the general procedure for the development of monoclonal antibodies against PBD-PSCs. In step 1, a mouse is immunized with the PBD-PSC by injecting the mouse with the stem cells. The mouse spleen produces plasma cells that secrete antibodies against the stem cells. In step 2, the myeloma cells unable to produce antibodies are selected. In step 3, the mouse spleen is removed, and plasma cells from the spleen are isolated and mixed with the myeloma cells. Cell fusion is induced to produce hybridomas. In step 4, cells are transferred to hypoxanthin-aminopterin-thymidine (HAT) medium. The unfused plasma cells and unfused myeloma cells die. Finally, in step 5, hybridomas that produce antibodies specific to the pluripotent stem cells are selected and grown in bulk.

Example 2

Isolation of PBD-PSCs from Blood or Tissue Source

The following example demonstrates a method for the isolation of PBD-PSCs.

Figure 11:
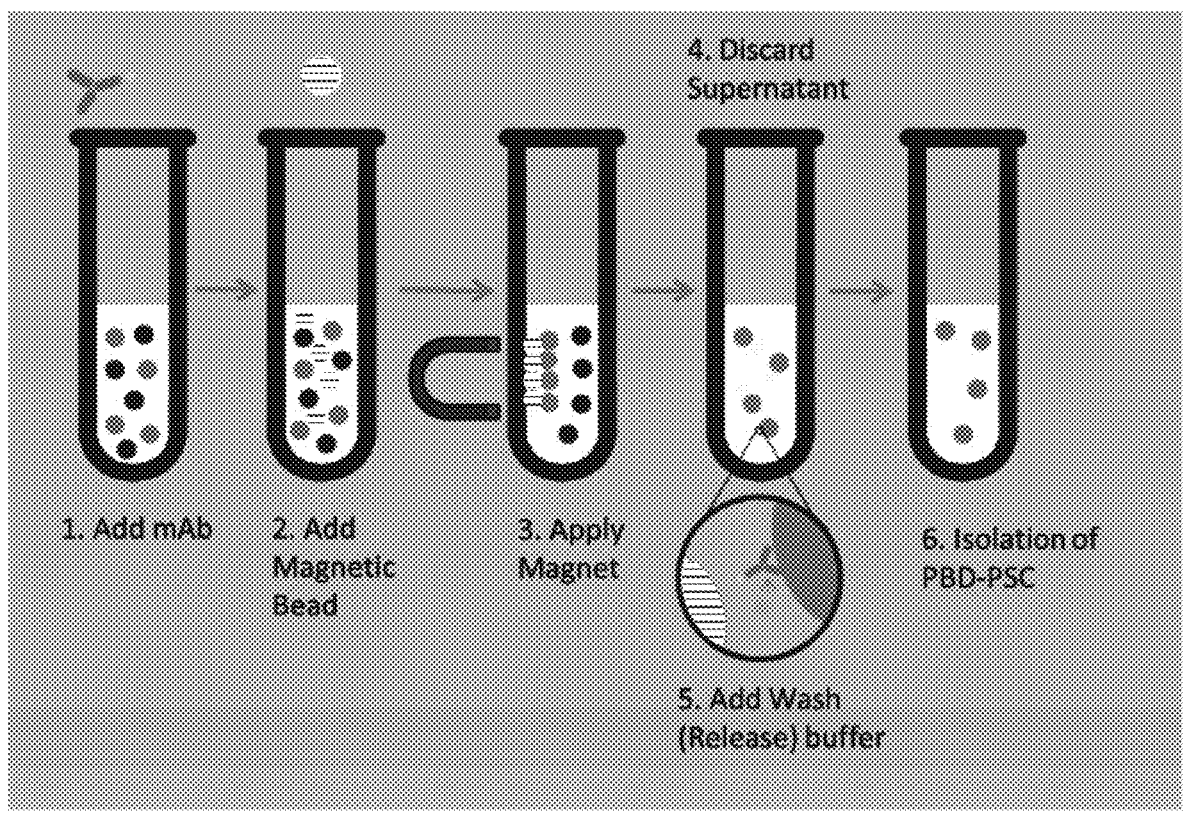
FIG. 11 illustrates one embodiment for the process for the isolation of the PBD-PSCs. The sample containing stem cells (tissue homogenate, peripheral blood, or other stem cell sources as described herein) is contacted with monoclonal antibodies developed as shown in FIG. 10. Magnetic beads are added to the mixture, and a magnetic field is applied. A wash buffer is introduced, and the PBD-PSCs are isolated.

A sample is obtained from a subject. The sample can include peripheral blood, adipose tissue, bone marrow, ovarian follicular fluid, or seminal plasma, or combinations thereof. As shown in FIG. 11, the sample is mixed with a mAb against the PBD-PSC. The monoclonal antibody can be, for example, an antibody against PTH1R. In some embodiments, magnetic beads can be included for the separation of the mAb-PBD-PSC complex. In some embodiments, avidin or streptavidin and biotin are used to attach the magnetic beads to the antibody. In this case, a magnetic field is applied, and the sample is washed to remove unbound supernatant. The PBD-PSC is released from the mAb with a wash buffer, and the cells are isolated.

Example 3

Isolation of PBD-PSCs from Peripheral Blood

The following example demonstrates a method for the isolation of PBD-PSCs from peripheral blood using an extracorporeal system.

Figure 12:
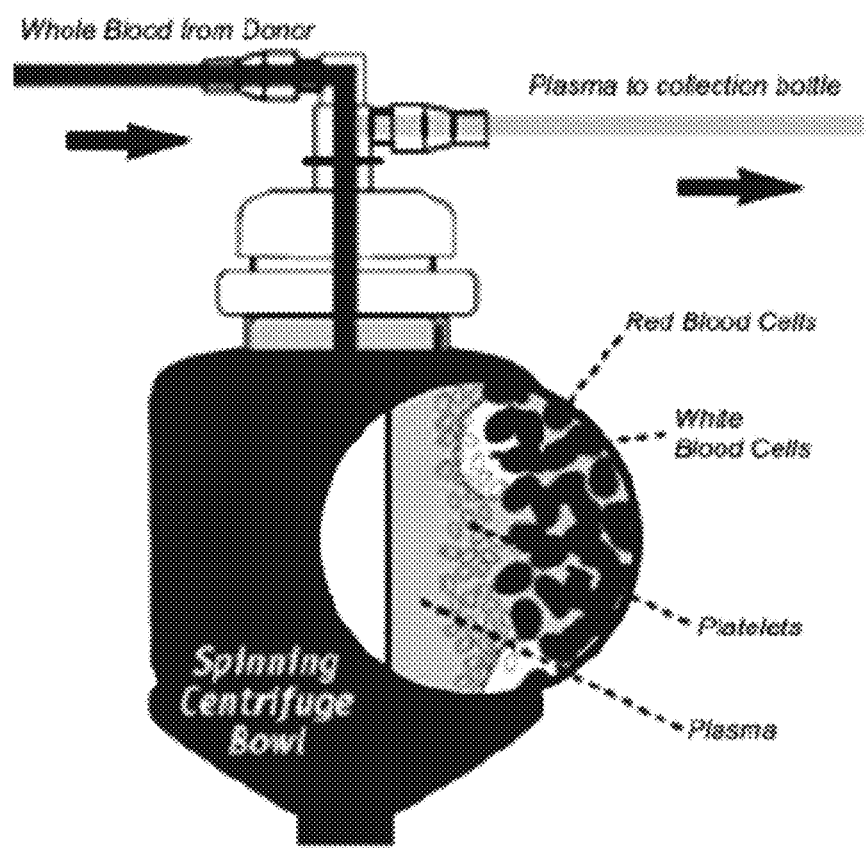
FIG. 12 illustrates a method for isolating the PBD-PSCs in an extracorporeal system. Peripheral blood from a subject is passed through an extracorporeal membrane, preferably a porous membrane, configured to capture the PBD-PSCs. A centrifugal or gravity force is applied to the peripheral blood, such that the PBD-PSCs are captured and collected. Optionally, after the PBD-PSCs are removed from the peripheral blood, the pass-through blood is reinfused into the subject.

A subject, or donor, is connected to an extracorporeal device. The whole blood is drawn from the donor, and directed to an extracorporeal device, as depicted in FIG. 12. The device comprises a porous membrane through which the blood passes. The blood can pass through the membrane by way of centrifugal or gravity force, whereas the PBD-PSCs are isolated or captured on the membrane. In this way, PBD-PSCs are isolated from the whole blood. The pass-through blood may be reinfused into the individual. The PBD-PSCs are isolated in quantities of from 1,000, to 100,000,000 cells/mL sample. In some embodiments, the isolated PBD-PSCs are prepared for subsequent reinfusion or administration to the individual.

Example 4

Growth of PBD-PSCs on a Nanofiber Matrix

The following example demonstrates a method for growing PBD-PSCs on a nanofiber matrix.

Figure 20A:
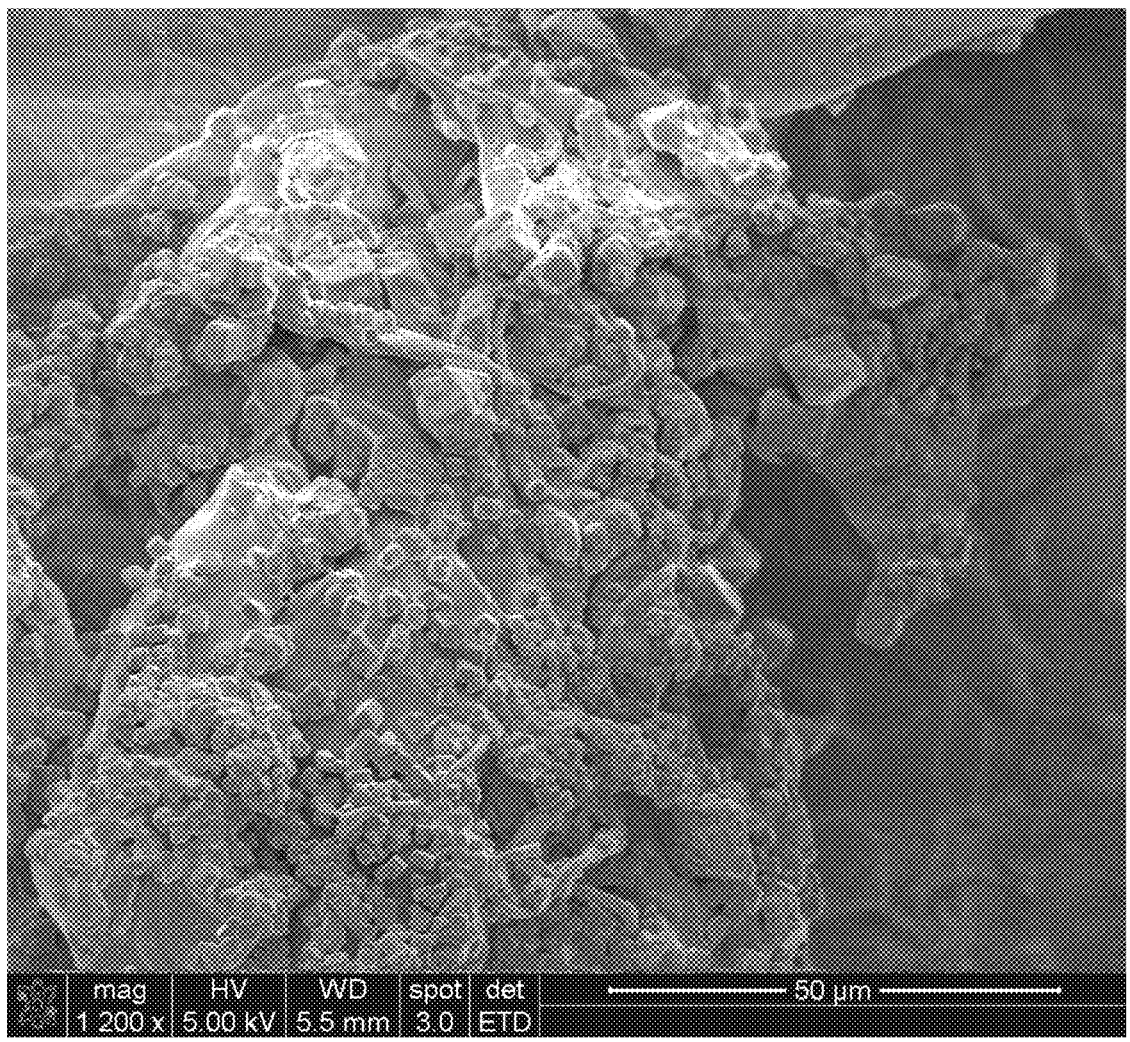
FIGS. 20A-20D depict electron micrographs of PBD-PSCs obtained from a healthy male, grown on a nanofiber matrix. The micrographs show the PBD-PSCs on the matrix over time, at time points of 0 minutes (FIG. 20A), 5 minutes (FIG. 20B), 30 minutes (FIG. 20C), and 120 minutes (FIG. 20D).
Figure 20B:
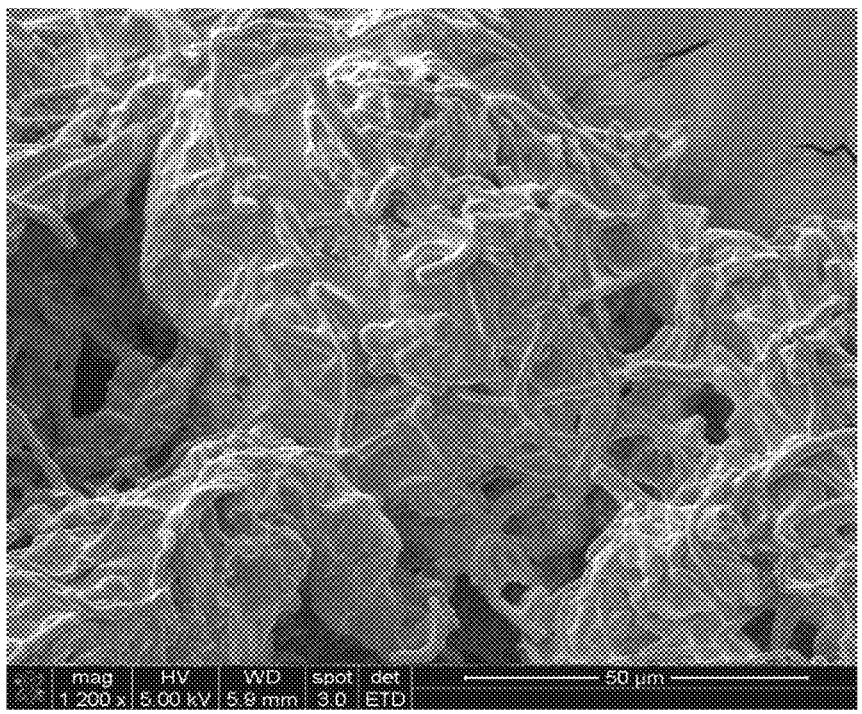
Figure 20B:
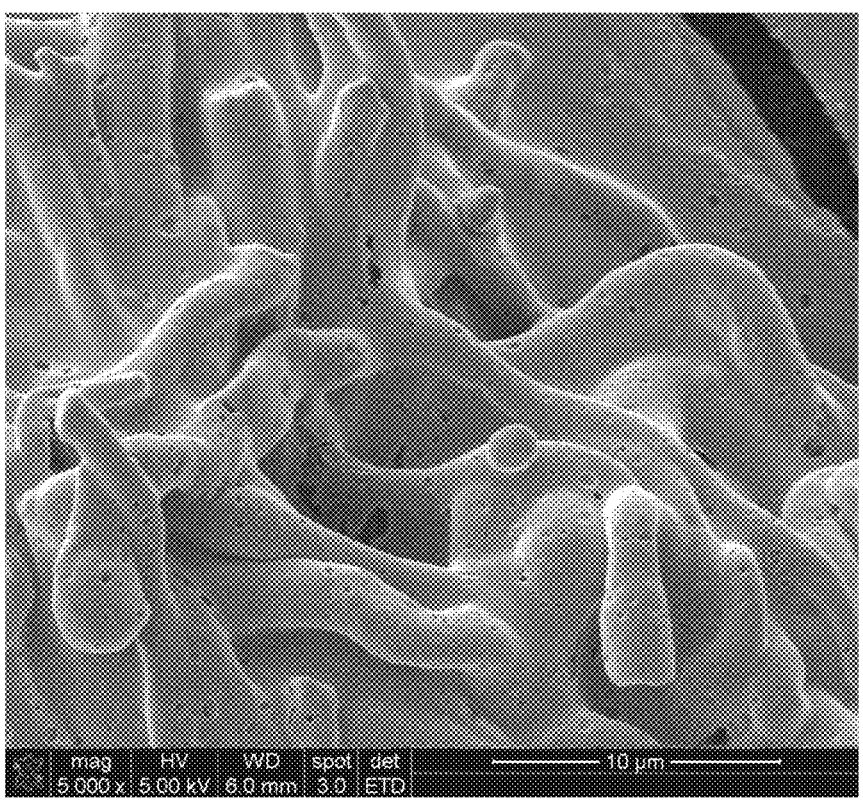
Figure 20C:
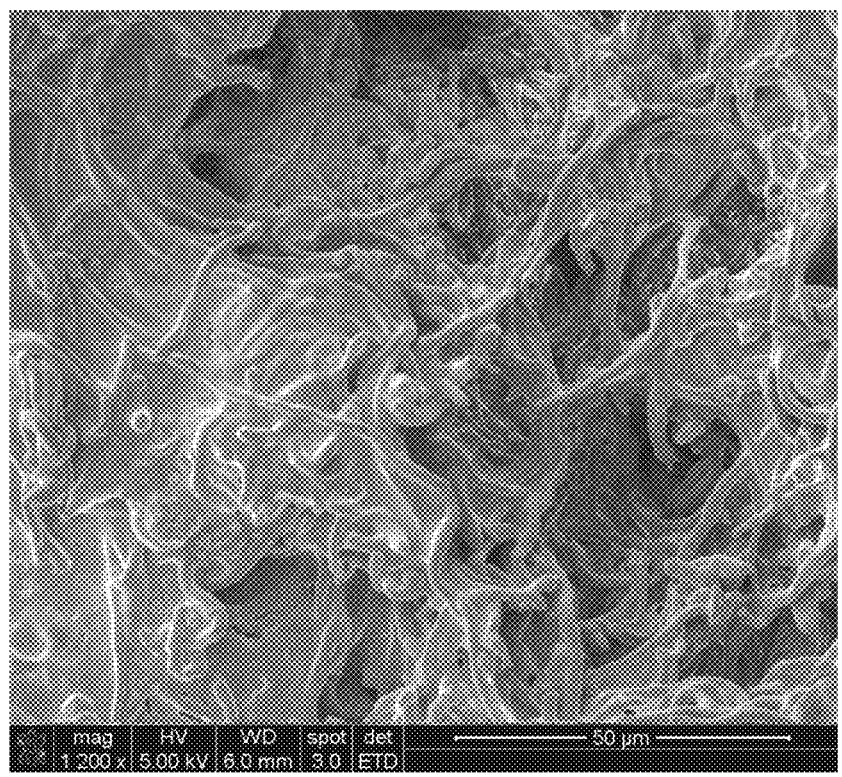
Figure 20C:
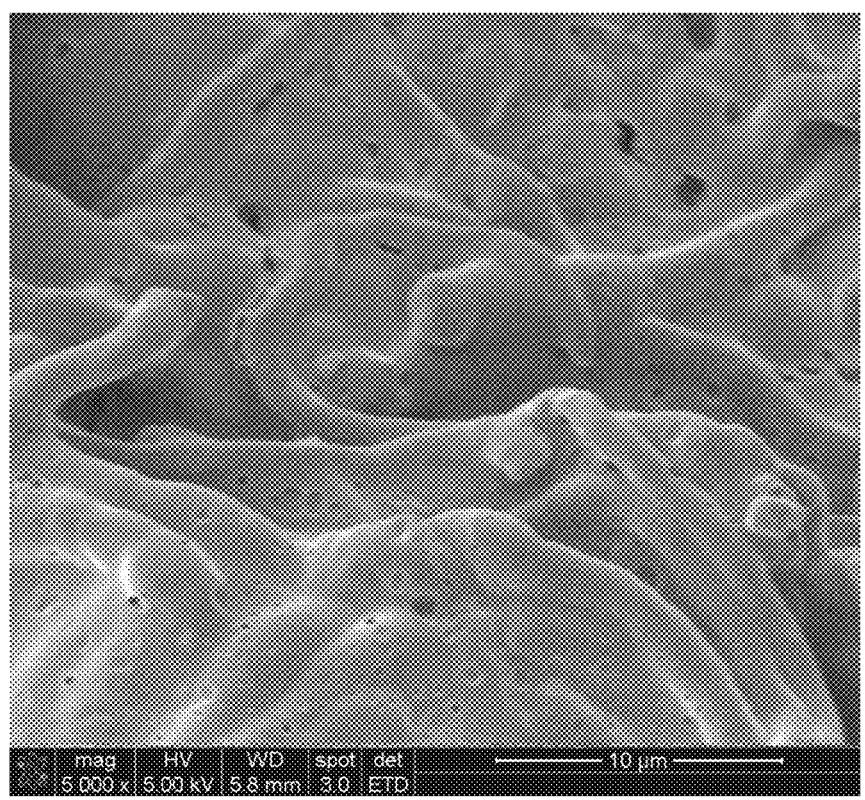
Figure 20D:
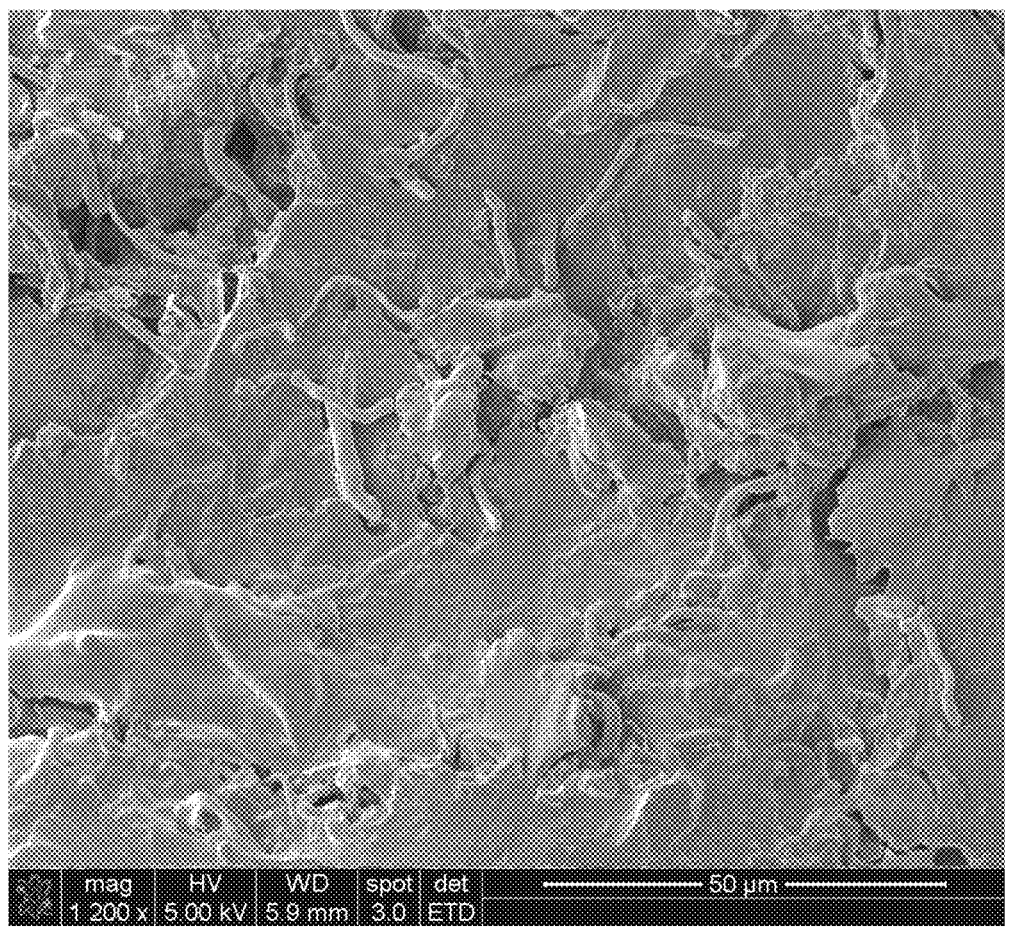

PBD-PSCs were isolated from a 55 year old healthy male and grown on a nanofiber matrix. Electron micrographs of the nanofiber matrix having PBD-PSCs grown thereon are shown in FIG. 20A (0 min), FIG. 20B (5 min; top, 1200× magnification; bottom, 5000×magnification), FIG. 20C (30 min; top, 1200×magnification; bottom, 5000×magnification), and FIG. 20D (120 min). The PBD-PSCs bind and lay down on the matrix within 5-30 minutes.

The nanofiber matrix was prepared from electrospun polycaprolactone (PCL) fibers, ranging in thickness from 200-700 μm. The fibers were broken down into powder by use of laser. The combinatorial use of this matrix may include injection into joints and bones (such as fractures and dentistry applications) or for placement on a wound.

Example 5

Skin Treatment Using PBD-PSCs

The following example demonstrates a method of treating skin to improve collagen and elastin using a PBD-PSC preparation.

Figure 21:
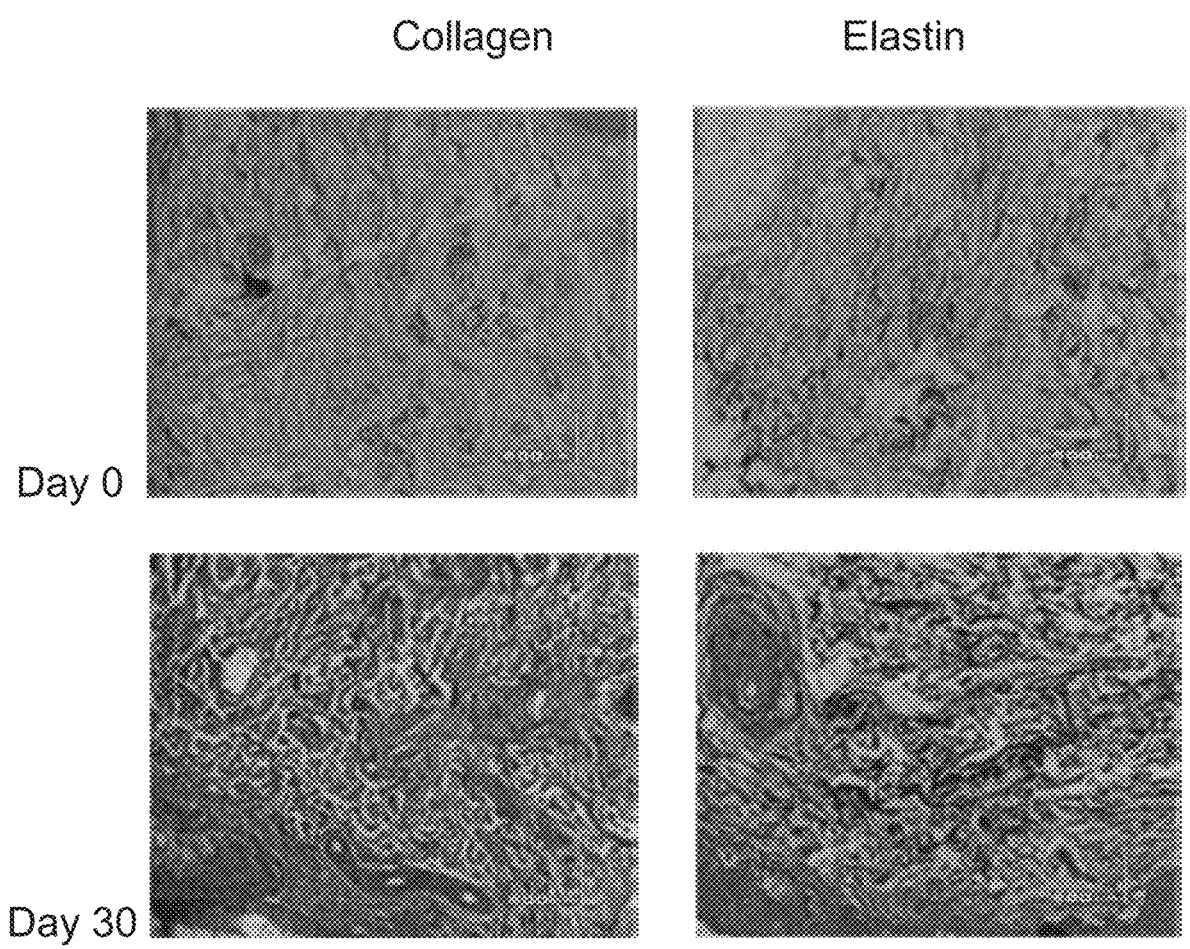
FIG. 21 shows an exemplary treatment of skin using a PBD-PSC preparation as a mesotherapy agent to counter premature skin aging by increasing the presence of dermal collagen and elastin. Skin measurements of collagen and elastin were taken prior to treatment at day 0 and 30 days following treatment.

A PBD-PSC preparation was used to address the problem of aging skin. Autologous PBD-PSC was obtained from the subject and used as a mesotherapy agent to counter premature skin aging by increasing dermal collagen and elastin. As shown in FIG. 21, the amount of both collagen and elastin increased from pre-treatment (day 0) to 30 days post-treatment. In addition, as shown in Table 1, cosmetic measures of skin aging improved following treatment.

TABLE 1

Cosmetic Effect of PBD-PSCs for the Treatment of Aging Skin

| | % Patients Improved (n = 30) | |
|---|---|---|
| | 4 weeks (No/Sl/Mo/Ma) | 8 weeks (No/Sl/Mo/Ma) |
| Fine Lines | 0/23/77/0 | 0/0/80/20 |
| Radiance | 0/30/70/0 | 0/0/83/17 |
| Tightness | 0/43/57/0 | 0/0/83/17 |

These results demonstrate that a PBD-PSC preparation is useful for improving the effects of aging skin by increasing the dermal collagen and elastin, thereby reducing fine lines, and increasing radiance and tightness.

Example 6

Hair Regrowth Using PBD-PSCs

The following example demonstrates a method of treating hair loss, or improving hair growth using a PBD-PSC preparation.

Figure 22:
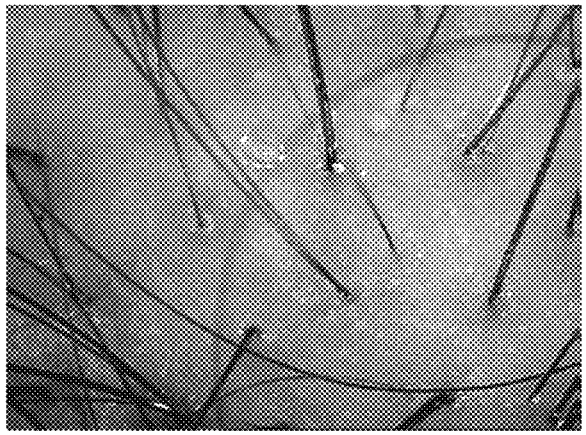
FIG. 22 shows an exemplary treatment of hair follicles and scalp using a PBD-PSC preparation so as to induce hair regrowth, and the figure depicts follicle growth prior to treatment and 10 weeks following treatment.
Figure 22:
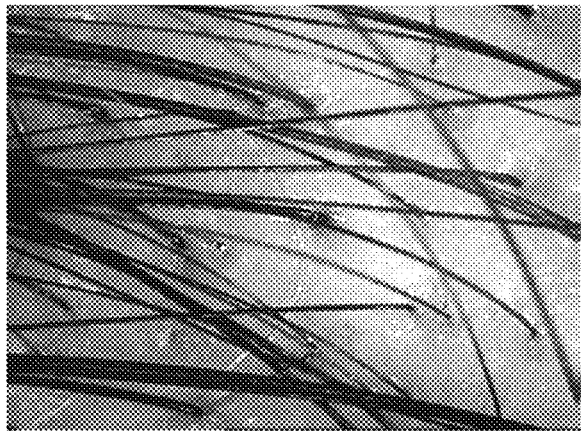

An autologous preparation of PBD-PSC was provided to a subject suffering from hair loss. As shown in FIG. 22, 10 weeks following the treatment with the PBD-PSC preparation, hair growth increased significantly. This result demonstrates the effectiveness of PBD-PSC preparations for use in improving hair growth. The PBD-PSC preparation comprises purified or isolated PBD-PSCs, and further comprises a pharmaceutically acceptable carrier. The preparation may further comprise a protein, growth factor, or other agent.

Example 7

PBD-PSCs for the Treatment of Bone Fractures

The following example demonstrates that PBD-PSCs are useful for treating bone fractures.

Figure 23A:
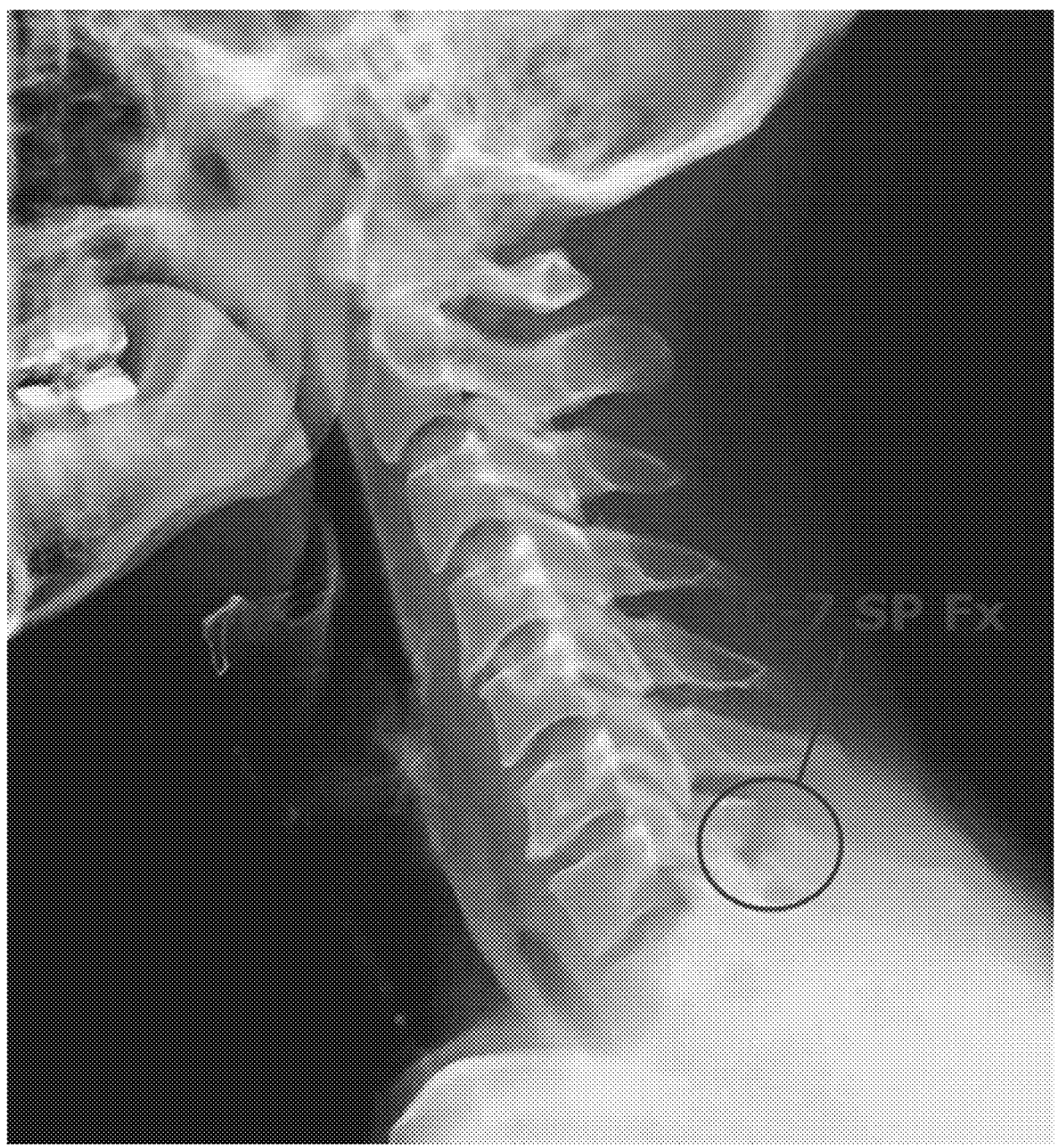
FIGS. 23A-23C show images following treatment of a spinous process of a spinous process fracture using an embodiment of a PBD-PSC treatment method.
Figure 23B:
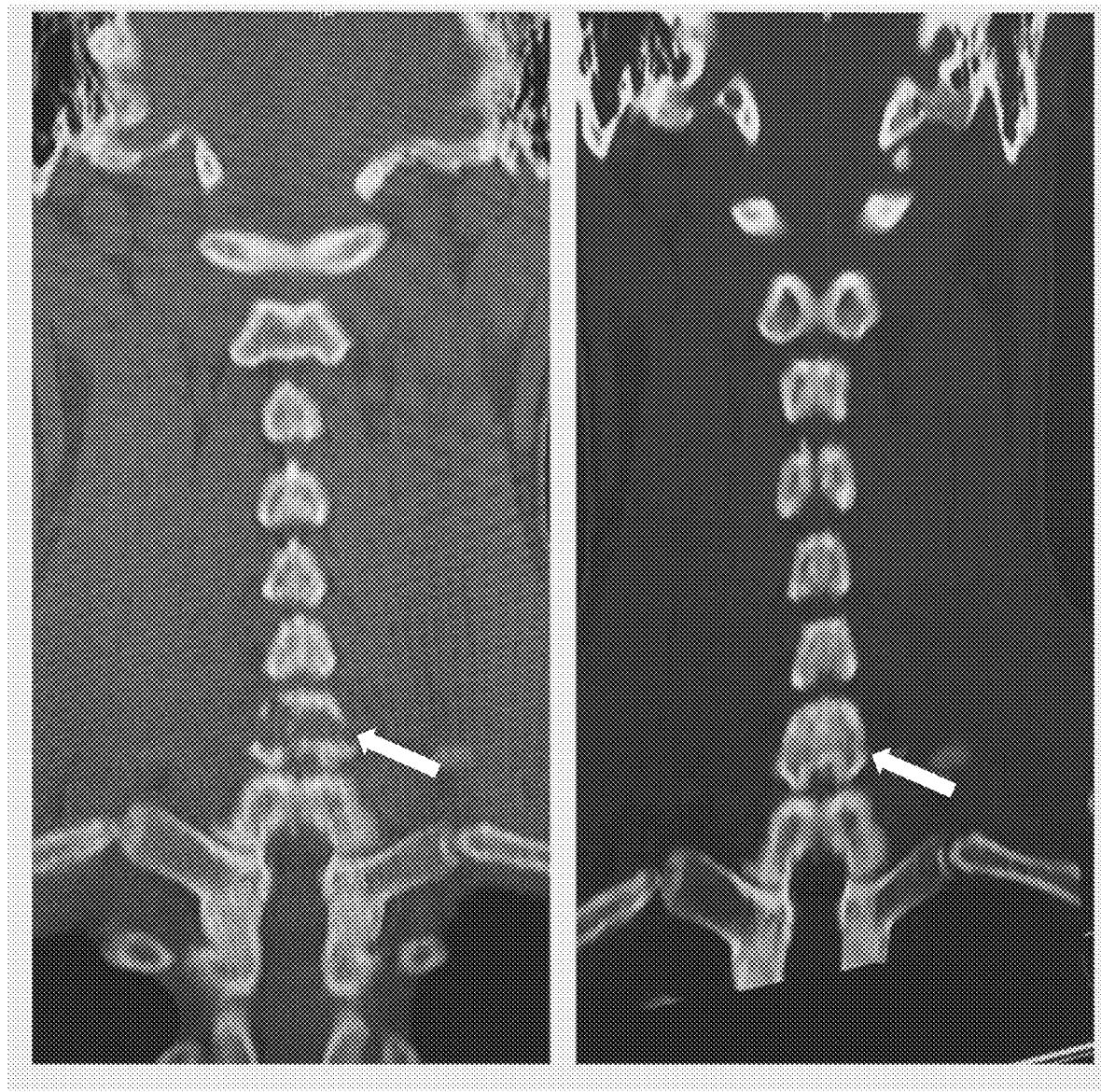
Figure 23C:
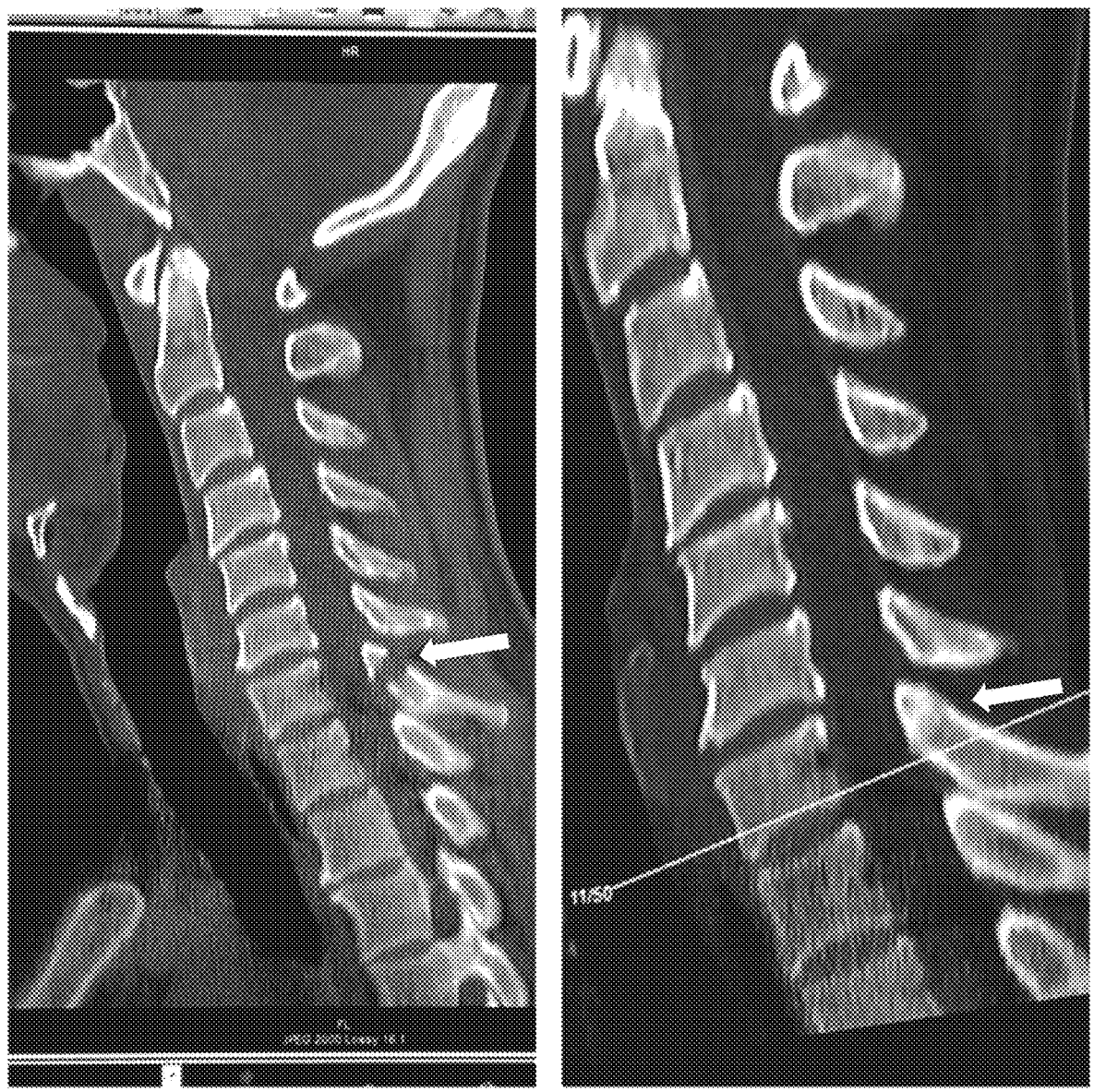
Figure 24:
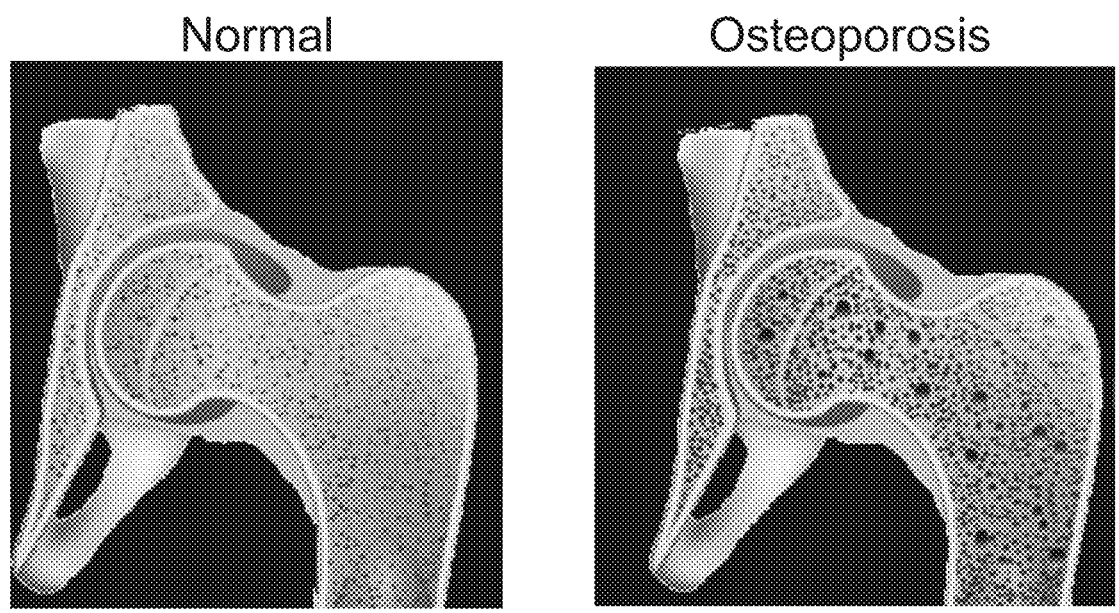
FIG. 24 depicts the effects of osteoporosis. The left image depicts a cutaway view of a normal, healthy bone. The right image depicts a cutaway view of a bone with osteoporosis, showing increased porosity and decreased bone density.

FIGS. 23A-23C depict an image of a bone fracture. The subject is a 50 year old patient with a non-healing C-7 spinous process fracture. The fracture was treated with a formulation comprising PBD-PSCs 9 months following the injury. The PBD-PSCs were injected intravenously and locally in the vicinity of the bone fracture.

FIG. 23B depicts a CT scan of a coronal cervical spine fracture. The left image shows the fracture prior to treatment. The subject was treated with a PBD-PSC preparation, as described above with intravenous and local injections. Four months following treatment (right image), the fracture was completely healed. FIG. 23C depicts a CT scan of a sagittal cervical spine fracture. The left image shows the fracture prior to treatment. Four months following treatment (right image), the fracture was completely healed.

Example 8

PBD-PSCs for the Treatment of Osteoporosis

The following example demonstrates that PBD-PSCs are useful for treating osteoporosis.

PBD-PSC preparations are useful for the treatment of osteoporosis. Osteoporosis commonly occurs among the elderly due to greater than normal bone loss. In this example, an elderly female subject showed progressive post-menopausal bone loss, as shown in Table 2.

TABLE 2

Osteoporosis Bone Loss and Treatment with PBD-PSCs

| | 79 months pre-treatment | 49 months pre-treatment | 0 months pre-treatment | Treatment | 86 months post-treatment |
|---|---|---|---|---|---|
| Lumbar | 0.908 | 0.834 | 0.792 | | 0.800 |
| Femur | 0.767 | 0.672 | 0.629 | | 0.695 |

All measurements in bone mineral density (g/cm$^2$)

The subject was treated with a formulation comprising PBD-PSCs. Following treatment, the bone loss halted in both the lumbar and femur. In fact, as shown in the table, the bone density not only halted, but increased at 86 months following treatment with PBD-PSCs. These data demonstrate the usefulness of PBD-PSCs for the treatment of osteoporosis by improving bone density.

Example 9

PBD-PSCs for the Improvement in Osteoporosis

The following example demonstrates an improvement in osteoporosis in a 65 year old subject with administration of PBD-PSCs.

Figure 25:
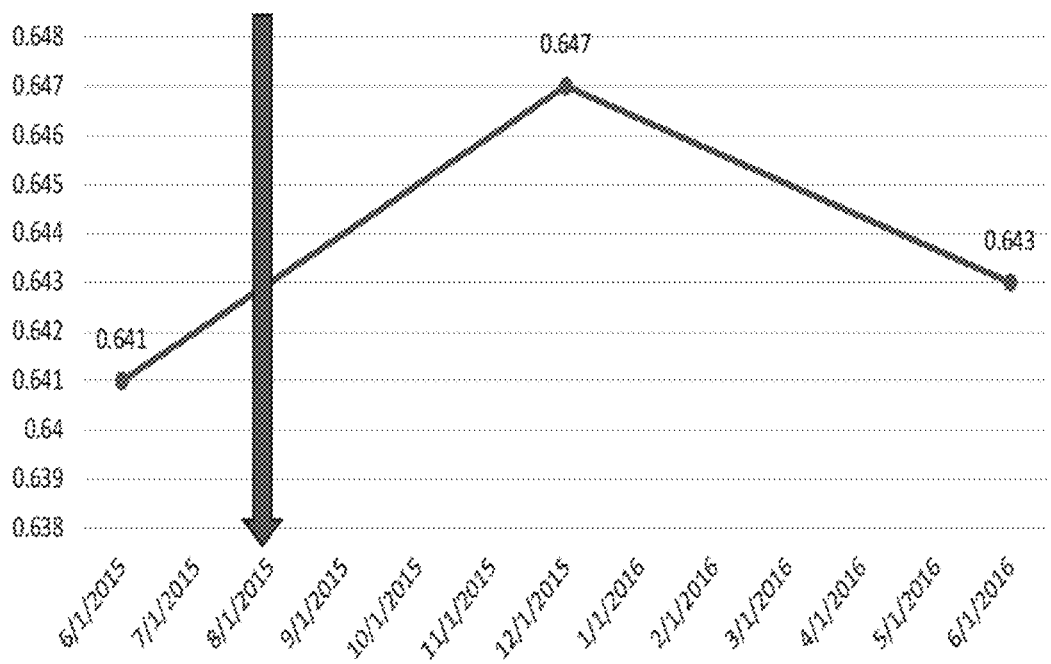
FIG. 25 depicts the bone density of a subject suffering from severe osteoporosis. The top panel shows the change in bone density in the lumbar spine following a single infusion of PBD-PSCs. The bottom panel shows the change in bone density in the left hip following a single infusion of PBD-PSCs. The y-axis represents bone density in $g/cm^2$, and the x-axis represents time.
Figure 25:
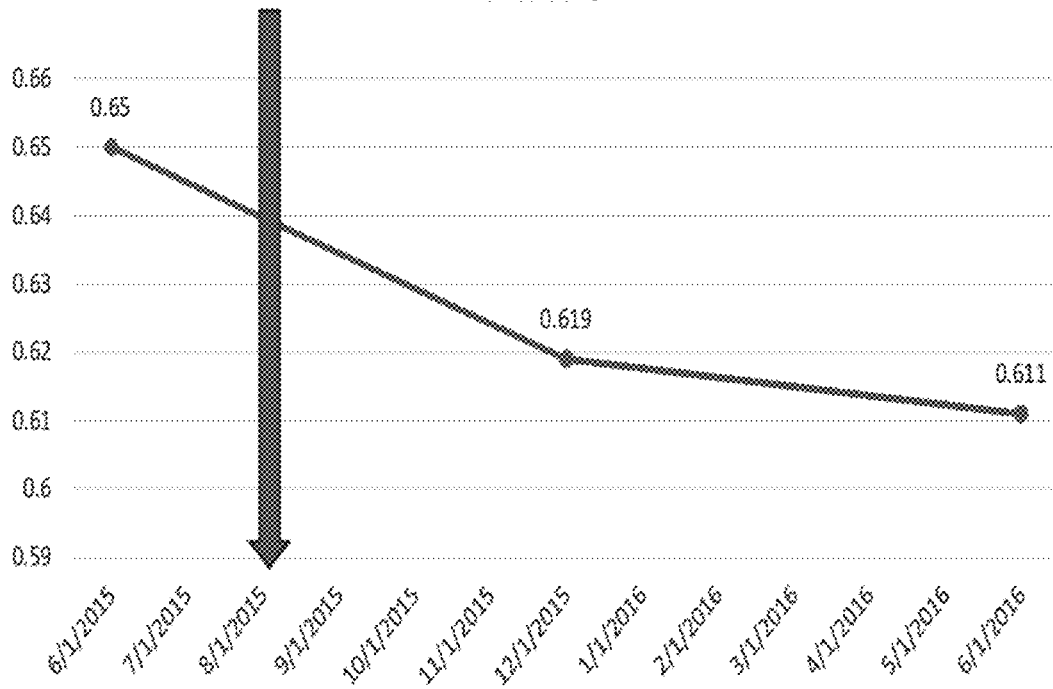

A 65 year old female patient with severe osteoporosis of the lumbar spine and left hip showed a slight improvement in bone density of the lumbar spine following a single infusion of PBD-PSCs. As shown in FIG. 25, the lumbar bone density improved from 0.641 to 0.647 (1.6%) g/cm$^2$. The benefit of the PBD-PSC infusion diminished slightly at nine months post-infusion (0.643 g/cm$^2$), indicating that a repeat infusion at 6 month intervals may sustain or build on the benefit of the initial infusion. The left hip bone density dropped following the PBD-PSC infusion from 0.650 to 0.619 (−4.77%) g/cm$^2$. However, the bone density subsequently slowed in its loss to 0.611 (−1.3%) g/cm$^2$, indicating that the infusion arrested the sharp decline in bone density in the left hip.

Example 10

PBD-PSCs for the Treatment of Osteopenia

The following example demonstrates that PBD-PSCs are useful for treating osteopenia.

Figure 26:
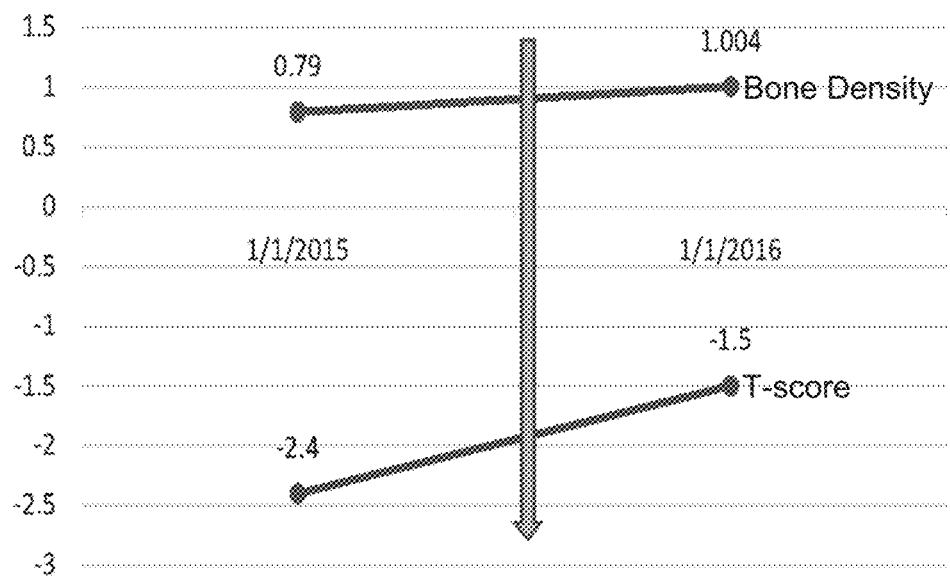
FIG. 26 depicts the change in bone density and the T-score of a subject with osteopenia. The top panel shows the change in bone density and T-score in the lumbar spine following a single PBD-PSC therapy. The bottom panel shows the change in bone density and T-score in the left hip following a single PBD-PSC therapy.
Figure 26:
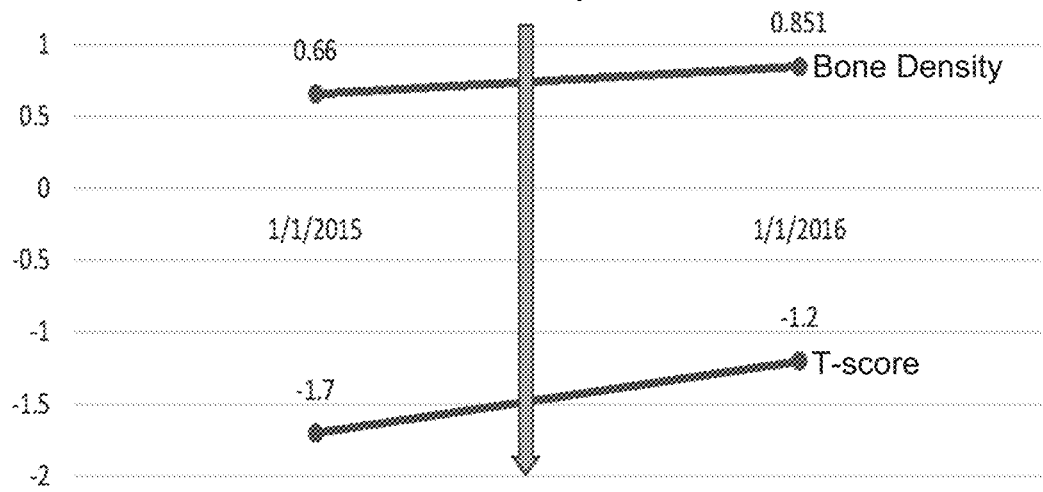

PBD-PSC preparations are useful for the treatment of osteopenia. Osteopenia is a condition in which bone mineral density is lower than normal, with a T-score between −1.0 and −2.5. In this example, a 75 year old female subject with osteopenia of the lumbar spine and left hip showed significant improvement in bone mineral density T-scores following a single PDB-PSC therapy. As shown in FIG. 26, the T-score in the lumbar spine (top graph) increased from −2.4 to −1.5 (a 37.5% improvement) with a concomitant increase in bone density from 0.79 g/cm$^2$ to 1.004 g/cm$^2$. The T-score in the left hip (bottom graph) increased from −1.7 to −1.2 (a 29.4% improvement), with a concomitant increase in bone density from 0.66 g/cm$^2$ to 0.851 g/cm$^2$.

Example 11

PBD-PSCs for the Improvement of Fertility

The following example demonstrates that PBD-PSCs are useful for improving fertility.

Figure 27:
FIG. 27 shows an exemplary treatment of endometrial thinning using a PBD-PSC intrauterine arterial injection. The pre-treatment image depicts high levels of endometrial thinning, whereas the post-treatment image shows that the thinning has largely dissipated.
Figure 27:
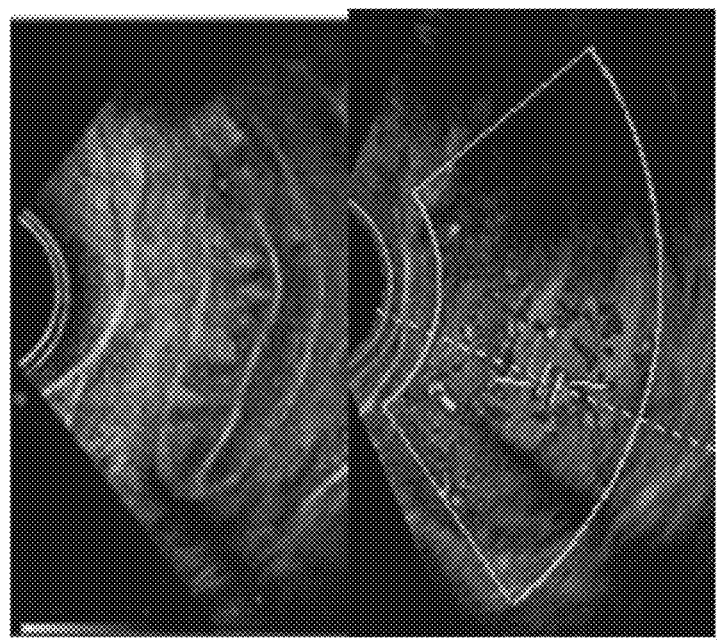

To determine whether PBD-PSCs are useful for improving fertility, an autologous preparation of PBD-PSCs was prepared. The preparation was intra-arterially injected into the uterine artery of a subject having extensive endometrial thinning. As shown in FIG. 27, following treatment with the PBD-PSCs, the endometrial thinning significantly improved. Thus, PBD-PSCs are useful for improving endometrial thinning.

To determine whether PBD-PSC therapy is useful for improving fertility, a PBD-PSC therapy was used in subjects who previously had experienced infertility. Women who previously attempted in vitro fertilization/intracytoplasmic sperm injection (IVF/ICSI), and who did not have polycystic ovary syndrome (PCOS) and with at least four repeated IVF/ICSI failures were treated with PBD-PSC intravenous therapy. Table 3 summarizes the results of the PBD-PSC therapy.

TABLE 3

Intravenous PBD-PSC Therapy for Improving Fertility

| Outcome | PBD-PSC Treatment | Previous Outcome |
|---|---|---|
| Stimulated Cycles | 33 | 198 |
| Dominant Follicle Diameter (mm$^2$) | 19.6 + 0.2 | 18.6 + 0.2 |
| No. of Follicles > 12 mm in diameter | 12.6 + 1.8 | 10.8 + 0.9 |
| Estradiol (pg/mL) | 2418 + 276 | 1878 + 144 |
| Estradiol per > 12 mm follicle (pg/mm) | 252 + 18 | 208 + 10 |
| Endometrial thickness (mm) | 10.9 + 0.3 | 10.6 + 0.4 |
| Canceled Cycles | 0 | 18 |
| Oocyte retrieval (Cycles) | 33 | 180 |
| Embryo Transfer | 33 | 162 |
| Clinical Pregnancy (%) | 7 (21.2%) | 16 (8.0%) |
| Ongoing Pregnancy (%) | 5 (15.1%) | 2 (1.0%) |
| No. of Oocytes | 7.3 + 2.6 | 5.6 + 1.7 |
| No. of Fertilized Oocytes | 5.4 + 1.1 | 3.7 + 0.9 |
| No. of Embryos | 3.3 + 1.0 | 1.8 + 0.6 |
| No. of Superior Embryos | 3.1 + 0.5 | 1.1 + 0.2 |

These results demonstrate that the PBD-PSC therapy improves a number of outcomes for women who previously experienced infertility with previous attempts with IVF/ICSI.

Furthermore, in a study involving 226 subjects, women who attempted IVF alone experienced lower successful IVF outcomes (41.3%) than those who combined PBD-PSC therapy with IVF (81.6%), as shown in Table 4.

TABLE 4

IVF/ICSI Outcomes in Women with or without PBD-PSC Therapy

| Treatment | Successful Outcome |
| --- | --- |
| WF | 41.3% |
| WF + Lymphocyte immunotherapy | 62.4% |
| WF + Lymphocyte immunotherapy— PBD-PSC | 81.6% |

In addition, an intrauterine artery PBD-PSC injection for endometrial thinning in 17 infertile women with previous implantation failure show increased endometrial thickness and improved fertility outcomes, as shown in Table 5. The average endometrial thickness in the 17 women prior to treatment was 4.67 mm, and the average thickness following treatment was 7.75 mm (increase of 3.08 mm; 66% increase).

TABLE 5

Intravenous PBD-PSC Therapy for Increased Endometrial Thickness

| Patient | Endometrial Thickness (mm) | | Conceived |
| --- | --- | --- | --- |
| | Before | After | |
| Fk250971 | 4.7 | 6.6 | No |
| JK231173 | 5.9 | 12.5 | Yes |
| IR270674 | 3.4 | 7.3 | No |
| CT261270 | 4.3 | 9.2 | Yes |
| DF180671 | 3.3 | 9.7 | Yes |
| MB240882 | 5.2 | 7.3 | No |
| MH230573 | 5.7 | 8.5 | No |
| CF191174 | 5.6 | 6.7 | No |
| VP050872 | 5.6 | 6.6 | Yes |
| RK310176 | 4.7 | 9.4 | Yes |
| HS250973 | 4.9 | 8.3 | No |
| JB251172 | 4.2 | 8 | Yes |
| BL240968 | 5.4 | 6 | No |
| KT290677 | 3.9 | 5.8 | No |
| KL281174 | 4.3 | 6.6 | No |
| MA130364 | 3.3 | 6.2 | Yes |
| KR090278 | 5 | 7 | No |

Taken together, these results demonstrate the statistically significant effects of PBD-PSC therapy for the improvement of fertility. Specifically, the therapy resulted in a detectable improvement in ovarian function, oocyte number and quality, endometrial thickness, and endometrial receptivity.

Example 12

PBD-PSCs for the Treatment of Neurological Disorders

The following example demonstrates that PBD-PSCs are useful in the treatment of neurological disorders.

To determine whether PBD-PSC therapy is effective for treating neurological disorders, autologous stem cells were isolated from a subject suffering with progressive cerebellar ataxia. Cerebellar ataxia can occur as a result of many diseases and presents with symptoms of an inability to coordinate balance, gait, extremity and eye movement. Lesions to the cerebellum can cause dyssynergia, dysmetria, dysdiadochokinesia, dysarthria, and ataxia of stance and gait. Deficits are observed with movements on the same side of the body as the lesion (ipsilateral). Clinicians often use visual observation of people performing motor tasks in order to look for signs of ataxia. There are many causes of cerebellar ataxia including, among others, autoimmunity to Purkinje cells or other neural cells in the cerebellum, SNC vasculitis, multiple sclerosis, infections, bleeding infarction, tumors, direct injury, toxins (e.g., alcohol), and genetic disorders. After differentiation diagnosis, the current subject was thought to have alcohol-induced cerebellar ataxia. The subject had stopped drinking alcohol since being diagnosed. The subject was suffering from progressive to severe inability to coordinate balance and would have on average close to five falls a day. Prior intensive rehabilitation programs had failed to stop the progression and months of buspirone had little to no positive effect.

After informed consent was given, the patient agreed to autologous administration of PBD-PSC therapy. Peripheral blood was taken and over a 24 hour period, PBD-PSCs were isolated by using magnetic antibody positive selection of PTH1R, CD90, and CD133 and negative selection of CD45. The cells where then primed 18 hours with retinoic acid with the patient's own platelet rich lysate and plasma. The cells were administered by intravenous administration over a 45 minute period.

After seven days, the patient noticed an improvement in her condition by a decrease in her inability to coordinate balance, and had no fall during the eighth day. After an eight week period, the patient had experienced only one fall. No side effects from the therapy were observed. This example shows the effectiveness of PBD-PSC therapy for the treatment of cerebellar ataxia.

Example 13

PBD-PSCs for the Treatment of Malignancy

The following example demonstrates that PBD-PSCs are useful in the treatment of malignancy.

A 50 year old patient with refractory metastatic renal-cell carcinoma in the lung, who had a suitable familiar donor received infusions of PBD-PSC allograft from a blood type identical sibling. The patient received three infusions of donor pluripotent stem cells every month for three months.

Figure 28:
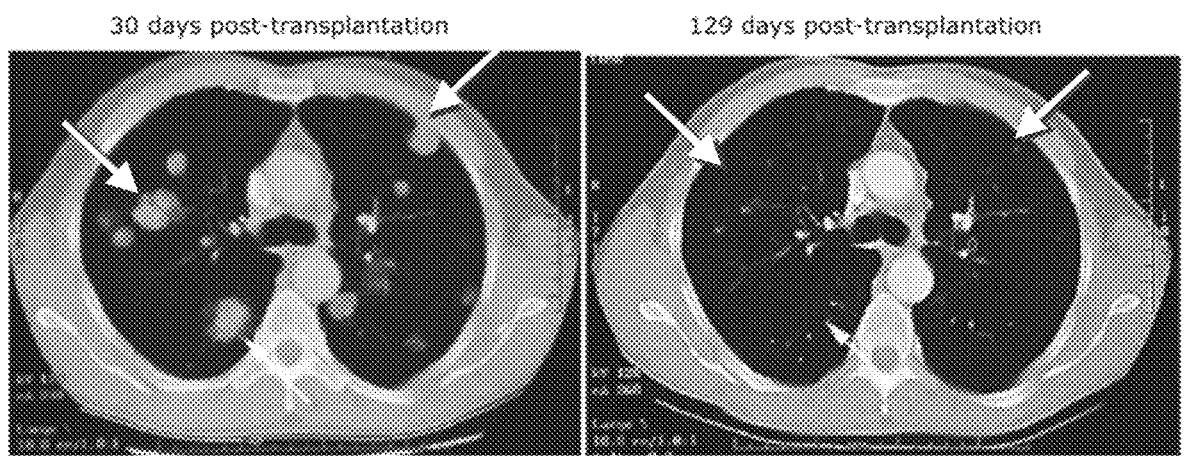
FIG. 28 shows an exemplary treatment of pulmonary metastases using PBD-PSC. The figure shows a CT image of the pulmonary metastases at 30 days (left) and 129 days (right) following transplantation of a PBD-PSC allograft, and shows a complete remission of metastases at 129 days after transplantation.

As shown in FIG. 28, 30 days following the transplantation, pulmonary metastases (arrows) are readily visible. At 129 days following transplantation, the pulmonary metastases are largely dissipated. The patient has had a complete response, has remained in remission, and has experienced a complete regression of the metastases.

This example demonstrates the effectiveness of PBD-PSC therapy for inducing sustained regression of metastatic renal-cell carcinoma in patients who have had no response to conventional immunotherapy.

Example 14

PBD-PSCs for the Treatment of Type 1 Diabetes

The following example demonstrates that PBD-PSCs are useful in the treatment of Type 1 diabetes.

A 17 year old male subject and a 16 year old female subject suffering from Type 1 diabetes were given two infusions of PBD-PSCs, injected into the pancreatic artery. The first infusion was given at week 1, and the second infusion was given at week 13.

Figure 29:
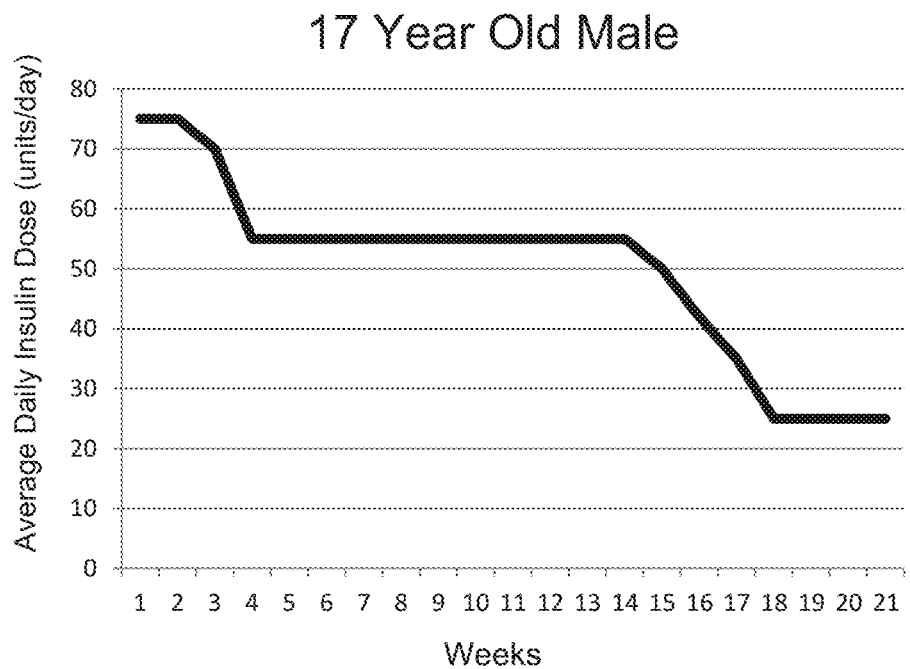
FIG. 29 depicts a decrease in the average insulin usage following doses of PBD-PSCs. Two doses of PBD-PSCs were administered to two subjects, a 17 year old male and a 16 year old female, at weeks 1 and 13. A decrease in the average daily insulin usage is observed following the PBD-PSC therapy.
Figure 29:
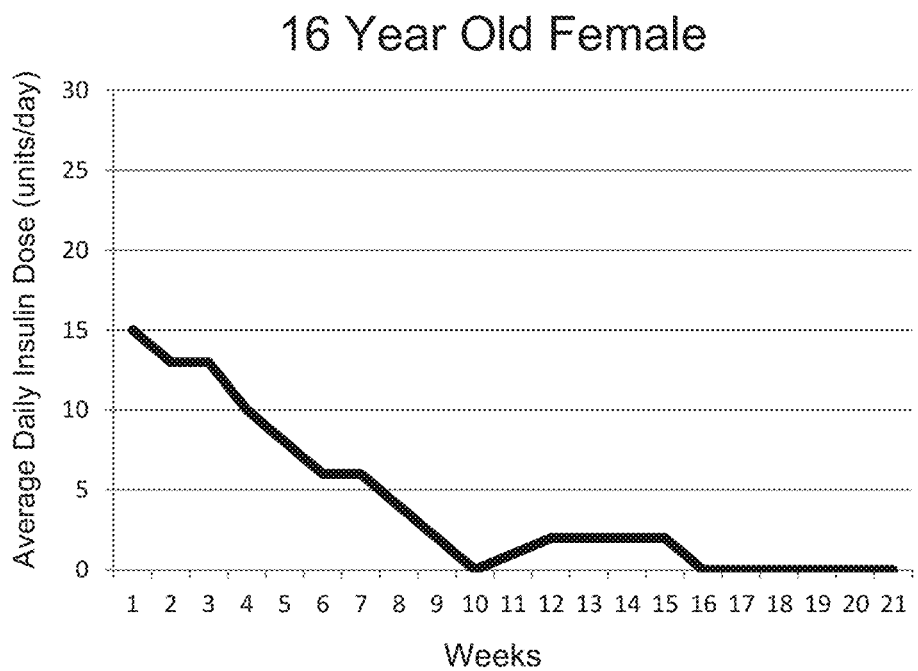

FIG. 29 shows the average daily insulin usage over time in weekly intervals. As shown in FIG. 29, the average daily insulin usage dropped following the initial PBD-PSC infusion, and again following the second PBD-PSC infusion.

This example demonstrates the effectiveness of PBD-PSC therapy for decreasing the average daily usage of insulin in subjects suffering from Type 1 diabetes.

Example 15

PBD-PSCs for the Treatment of Macular Degeneration

The following example demonstrates that PBD-PSCs are useful in the treatment of macular degeneration.

Two hundred mL of peripheral blood was removed from a 71 year old female patient suffering with dry macular degeneration using typical venipuncture. Sodium citrate was used as the anticoagulant. The patient's visual acuity test score before treatment was 20/200 in one eye and 20/500 in the other eye. The subject was legally blind and not able to drive a car. The PBD-PSCs were isolated using a combination of centrifugation (in swinging bucket rotor centrifuge) and filtration. The blood was first centrifuged for 10 minutes at 300 g. The plasma layer was removed and was centrifuged for another 10 minutes at 800 g. The plasma supernatant was centrifuged again at 1100 g for 10 minutes. The cell layer at the bottom was removed and placed in 5 mL of sterile saline and resuspended. The solution of suspended cells was then filtered through a 5 μm filter. Twenty five μL of the supernatant (which still contains platelets) was taken and subjected to ultrasonication and 40-60 megahertz ultrasound for 20 minutes to lyse the platelets. The platelet lysate was then subjected to centrifugation for 2,500 g for 15 minutes to remove debris. The platelet rich lysate was further filtered through a 0.22 μm filter for removal of debris. The platelet lysate was then added to the cells that had been suspended in saline and placed in a sterile culture plate of which the bottom of the plate had been coated with anti-human CD45 antibody. The plate was then placed into a refrigerated incubator at 4° C. with 5% $CO_2$ for 24 hours. The fluid was removed after 24 hours, and subjected to another 5 μm filtration. The filtrate (approx. 30 mL) was then injected intravenously into the patient over a 10 minute period. Analysis of the filtrate showed a total of approximately 9 million cells per mL of which the median size of the cells was 4.3 μm in diameter. Flow cytometry analysis showed more than 90% of the cells were CD133 positive and PTH-receptor positive. Less than 1% of cells were CD45 positive.

The patient exhibited a visual acuity score three months following administration of her platelet lysate activated-PBD-PSC cells of 20/40 in one eye and 20/50 in the other eye. The subject was no longer legally blind and was given new optics. The subject can now drive a car and live her daily life unassisted. After six months of administration of her own PBD-PSCs her improvement in visual acuity was sustained.

Example 16

Transfecting PTH Receptor-Positive Stem Cells with hTERT

The following example demonstrates transfection of parathyroid hormone receptor-positive stem cells with human telomerase reverse transcriptase.

An isolated population of PTH receptor-positive stem cells was obtained, as described in Example 2 or 3. The hTERT gene was introduced into a vector, and the vector including the hTERT gene was transfected into the isolated population of PTH receptor-positive stem cells using a non-viral transfection method, such as by chemical-based transfection, non-chemical-based transfection, and/or particle-based transfection. The hTERT transfected PTH receptor-positive stem cells are administered to a subject to treat, reverse, inhibit, or improve an age-related disorder.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g.,"a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of treating an age-related disorder in a mammalian subject in need thereof comprising:
    isolating a population of parathyroid hormone (PTH) receptor-positive pluripotent stem cells from peripheral blood of the subject, wherein the isolated population of PTH receptor-positive pluripotent stem cells express parathyroid hormone type 1 receptor (PTH1R), and the cell population is positive for CD90 and CD133; positive/negative for CD29, CD34, CD105, and CD106; and negative for SSEA-3, CD200, and CD45, wherein the isolating of PTH receptor-positive stem cells comprises:
        contacting the peripheral blood sample from the subject with an extracorporeal device; and
        capturing the PTH receptor-positive pluripotent stem cells on a porous membrane of the extracorporeal device, wherein capturing comprises applying centrifugal force to the extracorporeal device, or wherein the porous membrane comprises an antibody or portion thereof that specifically binds to the PTH receptor-positive pluripotent stem cells;
    transfecting said isolated population of PTH receptor-positive pluripotent stem cells with a human telomerase reverse transcriptase (hTERT) gene to generate hTERT transfected PTH receptor-positive pluripotent stem cells; and
    administering the hTERT transfected PTH receptor-positive pluripotent stem cells to said subject in a therapeutically effective amount and via a route sufficient to engraft at least a fraction of the hTERT transfected PTH receptor-positive pluripotent stem cells into the tissue to be treated.

2. The method of claim 1, wherein said administering reduces telomere shortening, increases cellular self-renewal, increases lifespan, reduces fine lines or wrinkles, or reduces aging in said subject.

3. The method of claim 1, wherein said age-related disorder is osteoporosis, arthrosis, glucose intolerance, insulin resistance, reduced heart, circulatory, or lung function, cardiovascular disease, a neurodegenerative disease, loss of memory, loss of neuromuscular coordination, or decrease of longevity.

4. The method of claim 1, wherein telomerase activity is recovered in cells of said subject.

5. The method of claim 1, wherein transfecting said population of PTH receptor-positive stem cells comprises non-viral transfection.

6. The method of claim 1, wherein transfecting said population of PTH receptor-positive stem cells comprises chemical-based transfection, particle-based transfection, or electroporation.

7. The method of claim 1, wherein the hTERT transfected PTH receptor-positive pluripotent stem cells are administered to the subject once weekly, once monthly, or once annually.

8. The method of claim 1, wherein the porous membrane comprises a monoclonal antibody or portion thereof.

9. The method of claim 1, wherein the administering comprises topical or parenteral administration.

10. The method of claim 1, wherein the hTERT transfected PTH receptor-positive pluripotent stem cells are administered to the subject in a quantity of about 10,000, 50,000, 100,000, 500,000, 1,000,000, 5,000,000, or 10,000,000 cells/mL.

* * * * *